(12) United States Patent
Drescher et al.

(10) Patent No.: US 7,834,048 B2
(45) Date of Patent: Nov. 16, 2010

(54) AZABICYCLOHEPTYL COMPOUNDS SUITABLE FOR TREATING DISORDERS THAT RESPOND TO MODULATION OF THE DOPAMINE D3 RECEPTOR

(75) Inventors: Karla Drescher, Dossenheim (DE); Andreas Haupt, Schwetzingen (DE); Liliane Unger, Ludwigshafen (DE); Sean C. Turner, Mannheim (GB); Wilfried Braje, Mannheim (DE); Roland Grandel, Dossenheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 420 days.

(21) Appl. No.: 11/665,421

(22) PCT Filed: Oct. 14, 2005

(86) PCT No.: PCT/EP2005/011089

§ 371 (c)(1),
(2), (4) Date: Feb. 7, 2008

(87) PCT Pub. No.: WO2006/040176

PCT Pub. Date: Apr. 20, 2006

(65) Prior Publication Data

US 2009/0048326 A1 Feb. 19, 2009

Related U.S. Application Data

(60) Provisional application No. 60/618,754, filed on Oct. 14, 2004.

(51) Int. Cl.
*A61K 31/403* (2006.01)
*C07D 209/52* (2006.01)

(52) U.S. Cl. .................. 514/414; 514/412; 548/452; 548/465

(58) Field of Classification Search ............. 514/414, 514/412; 548/452, 465
See application file for complete search history.

(56) References Cited

U.S. PATENT DOCUMENTS

| | | | | |
|---|---|---|---|---|
| 5,475,105 | A | * | 12/1995 | Steiner et al. .................. 544/48 |
| 5,521,209 | A | * | 5/1996 | Steiner et al. ............... 514/112 |
| 5,708,018 | A | | 1/1998 | Haadsma-Svensson et al. |
| 5,753,690 | A | * | 5/1998 | Steiner et al. ............... 514/411 |
| 6,028,073 | A | * | 2/2000 | Steiner et al. .......... 514/259.41 |
| 6,423,717 | B1 | | 7/2002 | Bromidge et al. |
| 2004/0152724 | A1 | | 8/2004 | Dart et al. |

FOREIGN PATENT DOCUMENTS

| | | |
|---|---|---|
| WO | WO 95/04713 | 2/1995 |
| WO | WO 96/23760 | 8/1996 |
| WO | WO 97/45403 | 12/1997 |
| WO | WO 97/45503 | 12/1997 |
| WO | WO 98/27081 | 6/1998 |
| WO | WO 99/58499 | 11/1999 |

OTHER PUBLICATIONS

Schafer et al. Drug Discovery Today 2008, 13 (21/22), 913-916.*
Horig et al. Journal of Translational Medicine 2004, 2(44).*
J.C. Schwartz et al., The Dopamine D, Receptor as a Target for Antipsychotics, in Novel Antipsychotic Drugs, H.Y. Meltzer, Ed. Raven Press, New York, 1992, pp. 135-144.
M. Dooley et al., Drugs and Aging 1998, 12, 495-514.

(Continued)

*Primary Examiner*—Rebecca L Anderson
*Assistant Examiner*—Jason M Nolan
(74) *Attorney, Agent, or Firm*—Lisa V. Mueller; Polsinelli Shughart PC

(57) ABSTRACT

The present invention relates to a compound of the formula (I)

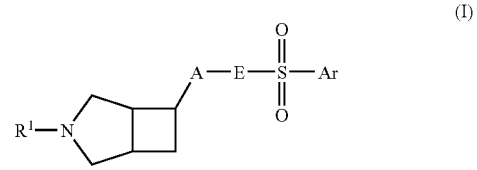

wherein
$R^1$ is H, $C_1$-$C_6$-alkyl which may be substituted by $C_3$-$C_6$-cycloalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl;
A is phenylene, pyridylene, pyrimidylene, pyrazinylene, pyridazinylene or thiophenylene, which can be substituted by one or more substituents selected from halogen, methyl, methoxy and $CF_3$;
E is $NR^5$ or $CH_2$, wherein $R^5$ is H or $C_1$-$C_3$-alkyl;
Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$, where $R^8$ is H, $C_1$-$C_4$-alkyl, fluorinated $C_1$-$C_4$-alkyl, $C_1$-$C_4$-alkylcarbonyl or fluorinated $C_1$-$C_4$-alkylcarbonyl, and where the cyclic radical Ar may carry 1, 2 or 3 substituents $R^a$; wherein the variable $R^a$ has the meanings given in the claims and in the description;
and physiologically tolerated acid addition salts thereof.

The invention also relates to the use of a compound of the formula I or a pharmaceutically acceptable salt thereof for preparing a pharmaceutical composition for the treatment of a medical disorder susceptible to treatment with a dopamine D3 receptor ligand.

19 Claims, No Drawings

OTHER PUBLICATIONS

J. N. Joyce, Pharmacology and Therapeutics 2001, 90, pp. 231-259 "The Dopamine $D_3$ Receptor as a Therapeutic Target for Antipsychotic and Antiparkinsonian Drugs".

P. Sokoloff et al., Localization and Function of the $D_3$ Dopamine Receptor, Arzneim. Frosch./Drug Res. 42(1), 224 (1992).

P. Sokoloff et al., Molecular Cloning and Characterization of a Novel Dopamine Receptor ($D_3$) as a Target for Neuroleptics, Nature, 347, 146 (1990).

Joyce, J.N. Dopamine D3 receptor as a therapeutic target for antipsychotic and antiparkinsonian drugs. Pharmacology and Therapeutics, 2001; 90:231-59.

Laszy, J., et al. Dopamine D3 receptor antagonists improve the learning performance in memory-impaired rats. Psychopharmacology, 2005; 179:567-75.

Heidbreder, C.A., et al. The role of central dopamine D3 receptors in drug addiction: a review of pharmacological evidence. Brain Research Reviews, 2005; 49:77-105.

Rogoz, Z., et al. Anxiolytic-like effects of preferential dopamine D3 receptor agonists in an animal model. Polish Journal of Pharmacology, 2003; 55:449-54.

Muhlbauer, B., et al. Dopamine D3 receptors in the rat kidney: role in physiology and pathophysiology. Acta Physiologica Scandinavica, 2000;168(1):219-23.

Benoit, S.C., et al. Altered feeding responses in mice with targeted disruption of the dopamine-3 receptor gene. Behavioral Neuroscience, 2000; 117(1):46-54.

\* cited by examiner

AZABICYCLOHEPTYL COMPOUNDS SUITABLE FOR TREATING DISORDERS THAT RESPOND TO MODULATION OF THE DOPAMINE D3 RECEPTOR

BACKGROUND OF THE INVENTION

The present invention relates to novel azabicycloheptyl compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the $D_1$ and $D_2$ receptors. More recently, a third subtype was found, namely the $D_3$ receptor which appears to mediate some effects of antipsychotics and antiparkinsonians (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

Compounds having an affinity for the dopamine $D_3$ receptor have been described in the prior art on various occasions, e.g. in WO 95/04713, WO 96/23760, WO 97/45503, WO98/27081 and WO 99/58499. Some of these compounds possess moderate affinities and or selectivities for the dopamine $D_3$ receptor. They have therefore been proposed as being suitable for treating diseases of the central nervous system. Some of the compounds described in these publications possess a pyrrolidinylphenyl structure. Unfortunately their affinity and selectivity towards the $D_3$ receptor or their pharmacological profile are not satisfactory. Consequently there is an ongoing need to provide new compounds, which either have an high affinity and an improved selectivity. The compounds should also have good pharmacological profile, e.g. a high brain plasma ratio, a high bioavailability, good metabolic stability, or a decreased inhibition of the mitochondrial respiration.

SUMMARY OF THE INVENTION

The invention is based on the object of providing compounds which act as highly selective dopamine $D_3$ receptor ligands. This object is surprisingly achieved by means of compounds of the formula I

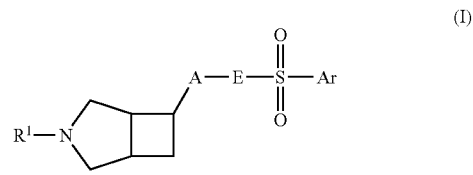

wherein $R^1$ is H, $C_1$-$C_6$-alkyl which may be substituted by $C_3$-$C_6$-cycloalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl;

A is phenylene, pyridylene, pyrimidylene, pyrazinylene, pyridazinylene or thiophenylene, which can be substituted by one or more substituents selected from halogen, methyl, methoxy and $CF_3$;

E is $NR^5$ or $CH_2$, wherein $R^5$ is H or $C_1$-$C_3$-alkyl;

Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$, where $R^8$ is H, $C_1$-$C_4$-alkyl, fluorinated $C_1$-$C_4$-alkyl, $C_1$-$C_4$-alkylcarbonyl or fluorinated $C_1$-$C_4$-alkylcarbonyl, and where the cyclic radical Ar may carry 1, 2 or 3 substituents $R^a$;

$R^a$ is halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, NH—C(O)—$NR^6R^7$, $NR^6R^7$, $NR^6R^7$—$C_1$-$C_6$-alkylene, O—$NR^6R^7$, where $R^6$ and $R^7$ are, independently of each other, H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring, phenylsulfonyl, benzyloxy, phenoxy, phenyl, or a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the 5 last-mentioned radicals may carry 1, 2, 3 or 4 substituents selected from hydroxy and the radicals $R^a$;

and physiologically tolerated acid addition salts thereof.

The present invention therefore relates to compounds of the general formula I and to their physiologically tolerated acid addition salts.

The present invention also relates to a pharmaceutical composition which comprises at least one compound of the formula I and/or at least one physiologically tolerated acid addition salt of I, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, poly-substituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

Particularly, the compounds of formula I can be in either the endo- or exo-configuration. Therefore, following isomers may occur: (1R,5S,6R)-6-(A-E-$SO_2$—Ar)-3-$R^1$-3-azabicyclo[3.2.0]heptane, (1S,5R,6S)-6-(A-E-$SO_2$—Ar)-3-$R^1$-3-aza-bicyclo[3.2.0]heptane, (1S,5R,6R)-6-(A-E-$SO_2$—Ar)-3-$R^1$-3-aza-bicyclo[3.2.0]heptane, and (1R,5S,6S)-6-(A-E-$SO_2$—Ar)-3-$R^1$-3-aza-bicyclo[3.2.0]heptane.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The pre-fix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_4$ Alkyl is a straight-chain or branched alkyl group having from 1 to 4 carbon atoms. Examples of an alkyl group are methyl, ethyl, n-propyl, iso-propyl, n-butyl, 2-butyl, iso-butyl or tert-butyl. $C_1$-$C_2$ Alkyl is methyl or ethyl, $C_1$-$C_3$ alkyl is additionally n-propyl or isopropyl.

$C_1$-$C_6$ Alkyl is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated $C_1$-$C_6$ alkyl is a straight-chain or branched alkyl group having from 1 to 6, especially 1 to 4 carbon atoms, in particular 1 to 3 carbon atoms, wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like. Fluorinated methyl is $CH_2F$, $CHF_2$ or $CF_3$.

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl, 1-methyl-1-ethylpropyl.

Fluorinated branched $C_3$-$C_6$ alkyl is alkyl having 3 to 6 carbon atoms at least one being a secondary or tertiary carbon atom wherein at least one, e.g. 1, 2, 3, 4 or all of the hydrogen atoms are replaced by a fluorine atom.

$C_1$-$C_6$ Alkoxy is a straight-chain or branched alkyl group having from 1 to 6, in particular 1 to 4 carbon atoms, which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Fluorinated $C_1$-$C_6$ alkoxy is a straight-chain or branched alkoxy group having from 1 to 6, in particular 1 to 4 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy and the like.

$C_1$-$C_6$-Hydroxyalkyl is an alkyl radical having from 1 to 6 carbon atoms as defined above, wherein one hydrogen atom is replaced by hydroxy. Examples comprise hydroxymethyl, 2-hydroxyethyl, 1-hydroxyethyl, 3-hydroxypropyl, 2-hydroxypropyl, 1-methyl-1-hydroxyethyl and the like.

$C_1$-$C_6$-Hydroxyalkoxy is an alkoxy radical having from 1 to 6, preferably from 2 to 4 carbon atoms as defined above, wherein one hydrogen atom is replaced by hydroxy. Examples comprise 2-hydroxyethyl, 3-hydroxypropyl, 2-hydroxypropyl, 1-methyl-2-hydroxyethyl and the like.

$C_1$-$C_6$-Alkoxy-$C_1$-$C_4$-alkyl is an alkyl radical having from 1 to 4 carbon atoms as defined above, wherein one hydrogen atom is replaced by $C_1$-$C_6$ alkoxy. Examples comprise methoxymethyl, 2-methoxyethyl, 1-methoxyethyl, 3-methoxypropyl, 2-methoxypropyl, 1-methyl-1-methoxyethyl, ethoxymethyl, 2-ethoxyethyl, 1-ethoxyethyl, 3-ethoxypropyl, 2-ethoxypropyl, 1-methyl-1-ethoxyethyl and the like.

$C_1$-$C_6$-Alkoxy-$C_1$-$C_4$-alkoxy is an alkoxy radical having from 1 to 4 carbon atoms as defined above, wherein one hydrogen atom is replaced by $C_1$-$C_6$ alkoxy. Examples comprise methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

$C_1$-$C_6$-Alkylcarbonyl is a radical of the formula R—C(O)—, wherein R is an alkyl radical having from 1 to 6 carbon atoms as defined above. Examples comprise acetyl, propionyl, n-butylryl, 2-methylpropionyl, pivalyl and the like.

$C_1$-$C_6$-Alkylcarbonylamino is a radical of the formula R—C(O)—NH—, wherein R is an alkyl radical having from 1 to 6 carbon atoms as defined above. Examples comprise acetamido, propionamido, n-butyramido, 2-methylpropionamido, 2,2-dimethylpropionamido and the like.

$C_1$-$C_6$ Alkylcarbonyloxy is a radical of the formula R—C(O)—O—, wherein R is an alkyl radical having from 1 to 6 carbon atoms as defined above. Examples comprise acetyloxy, propionyloxy, n-butyryloxy, 2-methylpropionyloxy, 2,2-dimethylpropionyloxy and the like.

$C_1$-$C_6$ Alkoxycarbonyl is a radical of the formula RO—C(O)—, wherein R is an alkyl radical having from 1 to 6 carbon atoms as defined above. Examples comprise methyloxycarbonyl, ethyloxycarbonyl, propyloxycarbonyl, isopropyloxycarbonyl and the like.

$C_1$-$C_6$ Alkylthio (also termed as $C_1$-$C_6$ alkylsulfanyl) is a radical of the formula R—S—, wherein R is an alkyl radical having from 1 to 6 carbon atoms as defined above. Examples comprise methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

$C_1$-$C_6$ Alkylsulfinyl is a radical of the formula R—S(O)—, wherein R is an alkyl radical having from 1 to 6 carbon atoms as defined above. Examples comprise methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$ Alkylsulfonyl is a radical of the formula R—S(O)$_2$—, wherein R is an alkyl radical having from 1 to 6 carbon atoms as defined above. Examples comprise methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

Fluorinated $C_1$-$C_6$ alkylcarbonyl is a radical of the formula R—C(O)—, wherein R is a fluorinated alkyl radical having from 1 to 6 carbon atoms as defined above. Examples comprise fluoroacetyl, difluoroacetyl, trifluoroacetyl, (R)-1-fluoroethylcarbonyl, (S)-1-fluoroethylcarbonyl, 2-fluoroethylcarbonyl, 1,1-difluoroethylcarbonyl, 2,2-difluoroethylcarbonyl, 2,2,2-trifluoroethylcarbonyl, (R)-1-fluoropropylcarbonyl, (S)-1-fluoropropylcarbonyl, 2-fluoropropylcarbonyl, 3-fluoropropylcarbonyl, 1,1-difluoropropylcarbonyl, 2,2-difluoropropylcarbonyl, 3,3-difluoropropylcarbonyl, 3,3,3-trifluoropropylcarbonyl, (R)-2-fluoro-1-methylethylcarbonyl, (S)-2-fluoro-1-methylethylcarbonyl, (R)-2,2-difluoro-1-methylethylcarbonyl, (S)-2,2-difluoro-1-methylethylcarbonyl, (R)-1,2-difluoro-1-methylethylcarbonyl, (S)-1,2-difluoro-1-methylethylcarbonyl, (R)-2,2,2-trifluoro-1-methylethylcarbonyl, (S)-2,2,2-trifluoro-1-methylethylcarbonyl, 2-fluoro-1-(fluoromethyl)ethylcarbonyl, 1-(difluoromethyl)-2,2-difluoroethylcarbonyl, (R)-1-fluorobutylcarbonyl, (S)-1-fluorobutylcarbonyl, 2-fluorobutylcarbonyl, 3-fluorobutylcarbonyl, 4-fluorobutylcarbonyl, 1,1-difluorobutylcarbonyl, 2,2-difluorobutylcarbonyl, 3,3-difluorobutylcarbonyl, 4,4-difluorobutylcarbonyl, 4,4,4-trifluorobutylcarbonyl, etc.

Fluorinated $C_1$-$C_6$ alkylcarbonylamino is a radical of the formula R—C(O)—NH—, wherein R is a fluorinated alkyl radical having from 1 to 6 carbon atoms as defined above. Examples comprise fluoroacetamido, difluoroacetamido, trifluoroacetamido, (R)-1-fluoroethylcarbonylamino, (S)-1-fluoroethylcarbonylamino, 2-fluoroethylcarbonylamino, 1,1-difluoroethylcarbonylamino, 2,2-difluoroethylcarbonylamino, 2,2,2-trifluoroethylcarbonylamino, (R)-1- fluoropropylcarbonylamino, (S)-1-fluoropropylcarbonylamino, 2-fluoropropylcarbonylamino, 3-fluoropropylcarbonylamino, 1,1-difluoropropylcarbonylamino, 2,2-difluoropropylcarbonylamino, 3,3-difluoropropylcarbonylamino, 3,3,3-trifluoropropylcarbonylamino, (R)-2-fluoro-1-methylethylcarbonylamino, (S)-2-fluoro-1-methylethylcarbonylamino, (R)-2,2-difluoro-1-methylethylcarbonylamino, (S)-2,2-difluoro-1-methylethylcarbonylamino, (R)-1,2-difluoro-1-methylethylcarbonylamino, (S)-1,2-difluoro-1-methylethylcarbonylamino, (R)-2,2,2-trifluoro-1-methylethylcarbonylamino, (S)-2,2,2-trifluoro-1-methylethylcarbonylamino, 2-fluoro-1-(fluoromethyl)ethylcarbonylamino, 1-(difluoromethyl)-2,2-difluoroethylcarbonylamino, (R)-1-fluorobutylcarbonylamino, (S)-1-fluorobutylcarbonylamino, 2-fluorobutylcarbonylamino, 3-fluorobutylcarbonylamino, 4-fluorobutylcarbonylamino, 1,1-difluorobutylcarbonylamino, 2,2-difluorobutylcarbonylamino, 3,3-difluorobutylcarbonylamino, 4,4-difluorobutylcarbonylamino, 4,4,4-trifluorobutylcarbonylamino, etc.

Fluorinated $C_1$-$C_6$ alkylcarbonyloxy is a radical of the formula R—C(O)—O—, wherein R is a fluorinated alkyl radical having from 1 to 6 carbon atoms as defined above fluoroacetyl, difluoroacetyl, trifluoroacetyl, (R)-1-fluoroethylcarbonyloxy, (S)-1-fluoroethylcarbonyloxy, 2-fluoroethylcarbonyloxy, 1,1-difluoroethylcarbonyloxy, 2,2-difluoroethylcarbonyloxy, 2,2,2-trifluoroethylcarbonyloxy, (R)-1-fluoropropylcarbonyloxy, (S)-1-fluoropropylcarbonyloxy, 2-fluoropropylcarbonyloxy, 3-fluoropropylcarbonyloxy, 1,1-difluoropropylcarbonyloxy, 2,2-difluoropropylcarbonyloxy, 3,3-difluoropropylcarbonyloxy, 3,3,3-trifluoropropylcarbonyloxy, (R)-2-fluoro-1-methylethylcarbonyloxy, (S)-2-fluoro-1-methylethylcarbonyloxy, (R)-2,2-difluoro-1-methylethylcarbonyloxy, (S)-2,2-difluoro-1-methylethylcarbonyloxy, (R)-1,2-difluoro-1-methylethylcarbonyloxy, (S)-1,2-difluoro-1-methylethylcarbonyloxy, (R)-2,2,2-trifluoro-1-methylethylcarbonyloxy, (S)-2,2,2-trifluoro-1-methylethylcarbonyloxy, 2-fluoro-1-(fluoromethyl)ethylcarbonyloxy, 1-(difluoromethyl)-2,2-difluoroethylcarbonyloxy, (R)-1-fluorobutylcarbonyloxy, (S)-1-fluorobutylcarbonyloxy, 2-fluorobutylcarbonyloxy, 3-fluorobutylcarbonyloxy, 4-fluorobutylcarbonyloxy, 1,1-difluorobutylcarbonyloxy, 2,2-difluorobutylcarbonyloxy, 3,3-difluorobutylcarbonyloxy, 4,4-difluorobutylcarbonyloxy, 4,4,4-trifluorobutylcarbonyloxy, etc.

Fuorinated $C_1$-$C_6$ alkylthio (also termed as fluorinated $C_1$-$C_6$-alkylsulfanyl) is a radical of the formula R—S—, wherein R is a fluorinated alkyl radical having from 1 to 6 carbon atoms as defined above. Examples comprise fluoromethylthio, difluoromethylthio, trifluoromethylthio, (R)-1-fluoroethylthio, (S)-1-fluoroethylthio, 2-fluoroethylthio, 1,1-difluoroethylthio, 2,2-difluoroethylthio, 2,2,2-trifluoroethylthio, (R)-1-fluoropropylthio, (S)-1-fluoropropylthio, 2-fluoropropylthio, 3-fluoropropylthio, 1,1-difluoropropylthio, 2,2-difluoropropylthio, 3,3-difluoropropylthio, 3,3,3-trifluoropropylthio, (R)-2-fluoro-1-methylethylthio, (S)-2-fluoro-1-methylethylthio, (R)-2,2-difluoro-1-methylethylthio, (S)-2,2-difluoro-1-methylethylthio, (R)-1,2-difluoro-1-methylethylthio, (S)-1,2-difluoro-1-methylethylthio, (R)-2,2,2-trifluoro-1-methylethylthio, (S)-2,2,2-trifluoro-1-methylethylthio, 2-fluoro-1-(fluoromethyl)ethylthio, 1-(difluoromethyl)-2,2-difluoroethylthio, (R)-1-fluorobutylthio, (S)-1-fluorobutylthio, 2-fluorobutylthio, 3-fluorobutylthio, 4-fluorobutylthio, 1,1-difluorobutylthio, 2,2-difluorobutylthio, 3,3-difluorobutylthio, 4,4-difluorobutylthio, 4,4,4-trifluorobutylthio, etc.

Fluorinated $C_1$-$C_6$ alkylsulfinyl is a radical of the formula R—S(O)—, wherein R is a fluorinated alkyl radical having from 1 to 6 carbon atoms as defined above. Examples comprise fluoromethylsulfinyl, difluoromethylsulfinyl, trifluoromethylsulfinyl, (R)-1-fluoroethylsulfinyl, (S)-1-fluoroethylsulfinyl, 2-fluoroethylsulfinyl, 1,1-difluoroethylsulfinyl, 2,2-difluoroethylsulfinyl, 2,2,2-trifluoroethylsulfinyl, (R)-1-fluoropropylsulfinyl, (S)-1-fluoropropylsulfinyl, 2-fluoropropylsulfinyl, 3-fluoropropylsulfinyl, 1,1-difluoropropylsulfinyl, 2,2-difluoropropylsulfinyl, 3,3-difluoropropylsulfinyl, 3,3,3-trifluoropropylsulfinyl, (R)-2-fluoro-1-methylethylsulfinyl, (S)-2-fluoro-1-methylethylsulfinyl, (R)-2,2-difluoro-1-methylethylsulfinyl, (S)-2,2-difluoro-1-methylethylsulfinyl, (R)-1,2-difluoro-1-methylethylsulfinyl, (S)-1,2-difluoro-1-methylethylsulfinyl, (R)-2,2,2-trifluoro-1-methylethylsulfinyl, (S)-2,2,2-trifluoro-1-methylethylsulfinyl, 2-fluoro-1-(fluoromethyl)ethylsulfinyl, 1-(difluoromethyl)-2,2-difluoroethylsulfinyl, (R)-1-fluorobutylsulfinyl, (S)-1-fluorobutylsulfinyl, 2-fluorobutylsulfinyl, 3-fluorobutylsulfinyl, 4-fluorobutylsulfinyl, 1,1-difluorobutylsulfinyl, 2,2-difluorobutylsulfinyl, 3,3-difluorobutylsulfinyl, 4,4-difluorobutylsulfinyl, 4,4,4-trifluorobutylsulfinyl, etc.

Fluorinated $C_1$-$C_6$ alkylsulfonyl is a radical of the formula R—S(O)$_2$—, wherein R is a fluorinated alkyl radical having from 1 to 6 carbon atoms as defined above. Examples comprise fluoromethylsulfonyl, difluoromethylsulfonyl, trifluoromethylsulfonyl, (R)-1-fluoroethylsulfonyl, (S)-1-fluoroethylsulfonyl, 2-fluoroethylsulfonyl, 1,1-difluoroethylsulfonyl, 2,2-difluoroethylsulfonyl, 2,2,2-trifluoroethylsulfonyl, (R)-1-fluoropropylsulfonyl, (S)-1-fluoropropylsulfonyl, 2-fluoropropylsulfonyl, 3-fluoropropylsulfonyl, 1,1-difluoropropylsulfonyl, 2,2-difluoropropylsulfonyl, 3,3-difluoropropylsulfonyl, 3,3,3-trifluoropropylsulfonyl, (R)-2-fluoro-1-methylethylsulfonyl, (S)-2-fluoro-1-methylethylsulfonyl, (R)-2,2-difluoro-1-methylethylsulfonyl, (S)-2,2-difluoro-1-methylethylsulfonyl, (R)-1,2-difluoro-1-methylethylsulfonyl, (S)-1,2-difluoro-1-methylethylsulfonyl, (R)-2,2,2-trifluoro-1-methylethylsulfonyl, (S)-2,2,2-trifluoro-1-methylethylsulfonyl, 2-fluoro-1-(fluoromethyl)ethylsulfonyl, 1-(difluoromethyl)-2,2-difluoroethylsulfonyl, (R)-1-fluorobutylsulfonyl, (S)-1-fluorobutylsulfonyl, 2-fluorobutylsulfonyl, 3-fluorobutylsulfonyl, 4-fluorobutylsulfonyl, 1,1-difluorobutylsulfonyl, 2,2-difluorobutylsulfonyl, 3,3-difluorobutylsulfonyl, 4,4-difluorobutylsulfonyl, 4,4,4-trifluorobutylsulfonyl, etc.

$C_3$-$C_6$ Cycloalkyl is a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methylprop-2-en-1-yl) and the like. $C_3$-$C_6$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl, 1-fluoro-2-propenyl and the like.

$C_1$-$C_6$-Alkylene is a hydrocarbon bridging group having 1, 2, 3, 4, 5 or 6 carbon atoms, like methylene, ethylene, 1,2- and 1,3-propylene, 1,4-butylene and the like.

3- to 7-membered heterocyclic radicals comprise saturated heterocyclic radicals, which generally have 3-, 4-, 5-, 6- or 7 ring-forming atoms (ring members), unsaturated non-aromatic heterocyclic radicals, which generally have 5-, 6- or 7 ring forming atoms, and heteroaromatic radicals, which generally have 5- or 6 ring forming atoms. The heterocylcic radicals may be bound via a carbon atom (C-bound) or an nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members. The heterocyclic radicals may also comprise 1 to 3 heteroatom-containing groups as ring members, like CO, SO and $SO_2$ Examples therefore are the below-mentioned oxo-containing heterocycles.

Examples of 3- to 7-membered, saturated heterocyclic radicals comprise 1- or 2-aziridinyl, 1-, 2- or 3-azetidinyl, 1-, 2- or 3-pyrrolidinyl, 2- or 3-oxopyrrolidinyl, 1-, 2-, 3- or 4-piperidinyl, 2-, 3- or 4-morpholinyl, 2-, 3- or 4-thiomorpholinyl, 1-oxo-thiomorpholinyl, 1,1-dioxothiomorpholinyl, 1-, 2- or 3-piperazinyl, 2-, 3-4- or 5-oxazolidinyl, 2-, 4- or 5-oxo-oxazolidinyl, 2-, 3-, 4- or 5-isoxazolidinyl, 2-oxiranyl, 2- or 3-oxetanyl, 2- or 3-oxolanyl, 2-, 3- or 4-oxanyl, 1,3-dioxolan-2- or 4-yl and the like, which may be unsubstituted or which may carry 1, 2 or 3 of the aforementioned radicals $R^a$ and/or hydroxy.

Unsaturated non-aromatic heterocyclic radicals are heterocyclic radicals which generally have 5-, 6- or 7 ring-forming atoms and which have 1 or 2 double bonds that do not form an aromatic π-electron system. Examples are 2,3-dihydropyrrolyl, 3,4-dihydropyrrolyl, 2,3-dihydrofuranyl, 3,4-dihydrofuranyl, 2,3-dihydrothiophenyl, 3,4-dihydrothiophenyl, 1,2-dihydropyridinyl, 2,3-Dihydropyridiynl, 3,4-dihydropyridinyl, 1,2,3,4-tetrahydropyridinyl, 2,3,4,5-tetrahydropyridinyl, and the like.

5- or 6-membered heteroaromatic radicals are heteroaromatic cyclic radicals, wherein the cyclic radical has 5 or 6 atoms which form the ring (ring members) and wherein generally 1, 2, 3 or 4 ring member atoms are selected from O, S and N, the other ring member atoms being carbon atoms. The heteroaromatic radicals may be bound via a carbon atom (C-bound) or an nitrogen atom (N-bound). Preferred heteroaromatic radicals comprise 1 nitrogen atom as ring member atom and optionally 1, 2 or 3 further heteroatoms as ring members, which are selected, independently of each other from O, S and N. Likewise preferred heteroaromatic radicals comprise 1 heteroatom as ring member, which is selected from O, S and N, and optionally 1, 2 or 3 further nitrogen atoms as ring members. Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furanyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadiazolyl, [1,3,4]-oxadiazolyl, 4- or 5-[1,2,3]-thiadiazolyl, [1,2,5]-thiadiazolyl, 3- or 5-[1,2,4]-thiadizolyl or [1,3,4]-thiadiazolyl, where the heteroaromatic radicals may be unsubstituted or may carry 1, 2 or 3 of the aforementioned radicals $R^a$ and/or hydroxy.

Examples of a phenyl ring fused to a saturated or unsaturated 5- or 6-membered carbocyclic or heterocyclic ring comprise indenyl, indanyl, naphthyl, 1,2- or 2,3-dihydronaphthyl, tetralin, benzofuranyl, 2,3-dihydrobenzofuranyl, benzothienyl, indolyl, indazolyl, benzimidazolyl, benzoxathiazolyl, benzoxadiazolyl; benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals $R^a$. This fused system may be bonded to the remainder of the molecule (more precisely to the sulfonyl group) via carbon atoms of the phenyl moiety or via ring atoms (C- or N-atoms) of the ring fused to phenyl.

If $R^6$ and $R^7$ form together with N a 4-, 5- or 6-membered ring, examples for this type of radical comprise, apart from the above-defined 5- or 6-membered heteroaromatic radicals containing at least one N atom as ring member, the N-atom further being bound to Ar (like in pyrrol-1-yl, pyrazol-1-yl, imidazol-1-yl, [1,2,3]-triazol-1-yl and the like), azetidinyl, azetinyl, pyrrolinyl, pyrrolidinyl, pyrazolinyl, pyrazolidinyl, imidazolinyl, imidazolidinyl, oxazolinyl, oxazolidinyl, piperidinyl, piperazinyl, morpholinyl and the like.

In a specific embodiment of the invention, in compound I Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S, and where the cyclic radical may carry 1, 2 or 3 substituents $R^a$ selected from the group consisting of halogen, $C_1$-$C_6$-alkyl, fluorinated $C_1$-$C_6$-alkyl, $NR^6R^7$, $NR^6R^7$—$C_1$-$C_6$-alkylene, where $R^6$ and $R^7$ are, independently of each other, H, $C_1$-$C_4$-alkyl or fluorinated $C_1$-$C_4$-alkyl or may form, together with N, a 4-, 5- or 6-membered saturated or unsaturated ring, $C_3$-$C_6$-cycloalkyl, fluorinated $C_3$-$C_6$-cycloalkyl, $C_1$-$C_6$-alkoxy, fluorinated $C_1$-$C_6$-alkoxy, CN, acetyl, carboxy and a saturated or unsaturated 5- or 6-membered heterocyclic ring comprising as ring members 1, 2 or 3 heteroatoms selected from N, O and S.

Preferably, the radical $R^1$ is selected from H, $C_1$-$C_4$-alkyl, $C_1$-$C_4$-alkyl which is substituted by $C_3$-$C_6$-cycloalkyl, fluorinated $C_1$-$C_4$-alkyl and $C_2$-$C_4$-alkenyl. More preference is given to H, propyl, cyclopropylmethylene, fluorinated methyl and allyl. In a particularly preferred embodiment, $R^1$ is n-propyl or allyl and especially n-propyl.

The group A is preferably phenylene, pyridylene or pyrimidylene. Moreover it is preferred that A is not substituted. In a more preferred embodiment, A is 1,4-phenylene, 1,2-phenylene, 2,5-pyridylene or 2,5-pyrimidylene. Particularly, A is 1,4-phenylene or 1,2-phenylene. Especially, A is 1,4-phenylene.

The group E is preferably $NR^5$, more preferably NH or $NCH_3$ and in particular NH.

Preferably, $R^6$ and $R^7$ are independently H, $C_1$-$C_4$-alkyl or $C_1$-$C_4$-alkoxy.

In case Ar is a 5- or 6-membered heteroaromatic radical, preferred radicals Ar are 2- or 3-thienyl, 2-, 3- or 4-pyridyl, 2-, 4- or 5-pyrimidinyl, 2-, 3- or 5-thiazolyl, 1,2,4-triazol-3-yl, 1,2,3-triazol-4-yl, 1,3,4-thiadiazol-2-yl, in particular 2-thienyl, 2-pyrimidinyl, 5-pyrimidinyl, 2-pyridinyl. The heteroaromatic radicals may be unsubstituted or may carry 1, 2 or 3 of the aforementioned radicals $R^a$. Preferred radicals are in this case halogen, $C_1$-$C_4$-alkyl, fluorinated $C_1$-$C_4$-alkyl, $C_1$-$C_4$-alkylcarbonylamino, nitro, phenoxy, phenylsulfonyl or a 3- to 7-membered heterocyclic ring as defined above, which is preferentially selected from 5- or 6-membered aromatic or non-aromatic heterocyclic rings containing 1 or 2 heteroatoms as ring members selected from O and N.

In case Ar is phenyl which is fused to a 5- or 6-membered heterocyclic or carbocyclic ring as described above and which is unsubstituted or which may carry 1, 2 or 3 radicals $R^a$ as given above, this fused system is preferably selected from indenyl, indanyl, naphthyl, tetralin, benzofuranyl, 2,3-dihydrobenzofuranyl, benzothienyl, indolyl, indazolyl, benzimidazolyl, benzoxazolyl, benzothiazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl and chromanyl, where the fused system may be unsubstituted or may carry 1, 2 or 3 of the aforementioned radicals $R^a$. Preferably, the fused system is selected from benzothienyl, benzoxazolyl, benzothiazolyl, benzoxadiazolyl, benzothiadiazolyl, benzoxazinyl, dihydrobenzoxazinyl, chinolinyl, isochinolinyl and tetrahydroisochinolinyl. Preferred substituents $R^a$ for this fused system are selected from halogen, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-alkylcarbonyl and fluorinated $C_1$-$C_4$-alkylcarbonyl. More preferred substituents $R^a$ for this fused system are selected from halogen, $C_1$-$C_4$-alkyl and fluorinated $C_1$-$C_4$-alkylcarbonyl.

In the aforementioned 5-membered heteroaromatic radicals, Ar preferably carries one radical $R^a$ in the 5-position (related to the 2-position of the $SO_2$-radical) and optionally one or two further radicals selected from halogen, in particular fluorine or chlorine.

Phenyl and the aforementioned 6-membered heteroaromatic radicals Ar preferably carry one radical $R^a$ in the 4-position (related to the 1-position of the $SO_2$-radical) and optionally one or two further radicals selected from halogen, in particular fluorine or bromine.

In one preferred embodiment of the invention Ar is phenyl that carries a radical $R^a$ in the 4-position of the phenyl ring and optionally 1 or 2 further radicals $R^b$, which are preferably selected from halogen, in particular from fluorine or chlorine. More preferably, Ar is phenyl that carries a radical $R^a$ in the 4-position of the phenyl ring and no further radical.

In another preferred embodiment of the invention Ar is 2-pyrimidinyl that carries a radical $R^a$ in the 5-position of the pyrimidine ring and optionally 1 or 2 further radicals $R^b$, which are preferably selected from halogen, in particular from fluorine or chlorine.

In another preferred embodiment of the invention Ar is 5-pyrimidinyl that carries a radical $R^a$ in the 2-position of the pyrimidine ring and optionally 1 or 2 further radicals $R^b$, which are preferably selected from halogen, in particular from fluorine or chlorine.

In another preferred embodiment of the invention Ar is 2-thienyl that carries a radical $R^a$ in the 3-position of the thiophene ring and optionally 1 or 2 further radicals $R^b$, which are preferably selected from halogen, in particular from fluorine or chlorine.

In another preferred embodiment of the invention, Ar is phenyl, which is fused to a 5- or 6-membered heterocyclic or carbocyclic ring as described above and which is unsubstituted or which may carry 1, 2 or 3 radicals $R^a$ as given above.

Preferred cyclic radicals of the group Ar are phenyl, 2- or 3-thienyl, 2-, 3- or 4-pyridyl, 1-, 2-, 3-, 4- or 5-indanyl, 2-, 3-, 4- or 5-benzofuranyl, in particular phenyl, 2-thienyl, 2- or 3-pyridinyl, 5-indanyl and 5-benzofuranyl.

In a more preferred embodiment of the invention, Ar is phenyl. Preferably, Ar is phenyl that carries a radical $R^a$ in the 4-position of the phenyl ring and optionally 1 or 2 further radicals $R^a$, which are preferably selected from halogen, in particular from fluorine or chlorine. More preferably, Ar is phenyl that carries a radical $R^a$ in the 4-position of the phenyl ring and no further radical.

In case $R^a$ is a saturated or unsaturated 3- to 7-membered heterocyclic ring, this radical is either unsubstituted or substituted by 1 to 3 substituents selected from OH and $R^a$. Preferred substituents are selected from hydroxy, halogen, $C_1$-$C_6$-alkyl, fluorinated $C_1$-$C_6$-alkyl, $C_1$-$C_6$-alkoxy and $C_1$-$C_4$-alkyl-$C_1$-$C_4$-alkoxy. Specifically, the substituents are selected from $C_1$-$C_4$-alkyl-$C_1$-$C_4$-alkoxy. Preferably, the 3- to 7-membered heterocyclic ring is either unsubstituted or carries one substituent.

In one preferred embodiment, the cyclic radical Ar is substituted by 1, 2 or 3 substituents $R^a$ selected from the group consisting of halogen, $C_1$-$C_6$-alkyl, fluorinated $C_1$-$C_4$-alkyl, $C_1$-$C_4$-alkoxy, fluorinated $C_1$-$C_4$-alkoxy such as $OCF_3$, $OCHF_2$ and $OCH_2F$, $C_2$-$C_4$-alkenyl, fluorinated $C_2$-$C_4$-alkenyl, $CH_2N(CH_3)_2$, $NR^6R^7$, where $R^6$ and $R^7$ are independently of each other H, $C_1$-$C_4$-alkyl or fluorinated $C_1$-$C_4$-alkyl or may form, together with N, a 4-, 5- or 6-membered saturated or unsaturated ring, especially an azetidinyl, a pyrrolidinyl or a piperidinyl system, $C_3$-$C_6$-cycloalkyl optionally substituted by halogen, acetyl or carboxyl. More preferably, Ar is phenyl which is substituted by 1, 2 or 3 substituents selected from the group consisting of halogen, $C_1$-$C_6$-alkyl, fluorinated $C_1$-$C_4$-alkyl, $C_1$-$C_4$-alkoxy, fluorinated $C_1$-$C_4$-alkoxy such as $OCF_3$, $OCHF_2$ and $OCH_2F$, $C_2$-$C_4$-alkenyl, fluorinated $C_2$-$C_4$-alkenyl, $CH_2N(CH_3)_2$, $NR^6R^7$, where $R^6$ and $R^7$ are independently of each other H, $C_1$-$C_4$-alkyl or fluorinated $C_1$-$C_4$-alkyl or may form, together with N, an azetidinyl, a pyrrolidinyl or a piperidinyl system, $C_3$-$C_6$-cycloalkyl optionally substituted by halogen, acetyl or carboxyl, or Ar is thienyl, pyridyl, benzofuranyl or indanyl, which are optionally substituted by halogen, $C_1$-$C_4$-alkyl or $C_1$-$C_4$-alkenyl. Even more preferably, Ar is phenyl which is substituted by 1, 2 or 3 substituents $R^a$ selected from fluorine or bromine, $C_1$-$C_6$-alkyl, especially methyl, ethyl, n-propyl, isopropyl, sec-butyl, isobutyl, dimethylpropyl, and particularly isopropyl, fluorinated $C_1$-$C_4$-alkyl, especially $CF_3$ or fluorinated isopropyl, $C_1$-$C_4$-alkoxy, especially methoxy, ethoxy, propoxy, isopropoxy or butoxy, $OCF_3$, $OCHF_2$, $OCH_2F$, isopropenyl, $CH_2N(CH_3)_2$, $NR^6R^7$, where $R^6$ and $R^7$ are independently of each other H, $C_1$-$C_4$-alkyl or fluorinated $C_1$-$C_4$-alkyl, $C_3$-$C_6$-cycloalkyl, especially cyclopentyl, fluorinated $C_3$-$C_6$-cycloalkyl, especially 2,2-difluorocyclopropyl, acetyl or carboxyl. Alternatively, Ar is thienyl or pyridyl which carry 1, 2 or 3 substituents selected from halogen, especially chlorine, and $C_1$-$C_4$-alkenyl, especially isopropenyl, or Ar is benzofuranyl or indanyl.

In an alternative preferred embodiment, Ar preferably carries one radical $R^a$, which has the formula $R^{a'}$

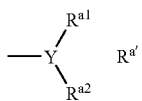

wherein
Y is N, CH or CF,
$R^{a1}$ and $R^{a2}$ are independently of each other selected from $C_1$-$C_2$-alkyl, in particular methyl, fluorinated $C_1$-$C_2$-alkyl, in particular fluoromethyl, difluoromethyl or trifluoromethyl, provided for Y being CH or CF one of the radicals $R^{a1}$ or $R^{a2}$ may also be hydrogen or fluorine, or
$R^{a1}$ and $R^{a2}$ form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6, preferably 2, 3 or 4, in particular $CH_2$—$CH_2$, CHF—$CH_2$ $CF_2$—$CH_2$, $CH_2$—$CH_2$—$CH_2$, CHF—$CH_2$—$CH_2$, $CF_2$—$CH_2$—$CH_2$, $CH_2$—CHF—$CH_2$, $CH_2$—$CF_2$—$CH_2$.

In case $R^a$, and $R^{a2}$ form a radical $(CH_2)_m$ it is preferred that 1 or 2 of the hydrogen atoms may be replaced by fluorine. Examples therefor are $CH_2$—$CH_2$, CHF—$CH_2$ $CF_2$—$CH_2$, $CH_2$—$CH_2$—$CH_2$, CHF—$CH_2$—$CH_2$, $CF_2$—$CH_2$—$CH_2$, $CH_2$—CHF—$CH_2$, and $CH_2$—$CF_2$—$CH_2$.

In case $R^{a1}$ and $R^{a2}$ are different from each other, the radical of the aforementioned formula Ra may have either (R)- or (S)-configuration with regard to the Y-moiety.

Examples for preferred radicals of the formula $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, (R)-2-fluoropropyl, (S)-2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluoro-1-methylethyl cyclopropyl, cyclobutyl, 1-fluorocyclopropyl, (S) and (R)-2,2-difluorocyclopropyl and 2-fluorocyclopropyl.

Amongst the radicals of the formula $R^{a'}$ those are preferred which carry 1, 2, 3 or 4, in particular 1 2 or 3 fluorine atoms.

Examples for alternatively preferred radicals of the formula $R^{a'}$ comprise 4-morpholinyl, 4-thiomorpholinyl, 4-(1, 1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-methoxymethylpyrrolodin-1-yl, (R)-2-methoxymethylpyrrolodin-1-yl, (S)-2-methoxymethylpyrrolodin-1-yl, 3-methoxymethylpyrrolodin-1-yl, (R)-3-methoxymethylpyrrolodin-1-yl, (S)-3-methoxymethylpyrrolodin-1-yl, 2-oxopyrrolidin-1-yl, 2-oxo-oxazolidin-3-yl, piperidin-1-yl, 2-methylpiperidin-1-yl, (S)-2-methylpiperidin-1-yl and (R)-2-methylpiperidin-1-yl.

More preferably, $R^{a'}$, is selected from isopropyl, fluorinated isopropyl (like (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl and 1-(difluoromethyl)-2,2-difluoroethyl), 1-azetidinyl, 1-pyrrolidinyl, 2-methoxymethylpyrrolidin-1-yl, (R)-2-methoxymethylpyrrolidin-1-yl and (S)-2-methoxymethylpyrrolidin-1-yl.

In a particularly preferred embodiment, radical $R^{a'}$ is in the 4-position of the phenyl ring.

In another preferred embodiment $R^a$ is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl. Amongst these radicals $R^a$, preference is given to radicals selected from 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadizolyl, [1,3,4]-oxadizolyl, 4- or 5-[1,2,3]-thiadiazolyl, [1,2,5]-thiadiazolyl, 3- or 5-[1,2,4]-thiadizolyl or [1,3,4]-thiadiazolyl, in particular from 2- or 3-furanyl, 2- or 3-thienyl, 1-, 2- or 3-pyrrolyl, pyrazolyl, imidazolyl, oxazolyl, isoxazolyl, 1,3,4-thiadiazolyl, 1,2,4-triazolyl, 1,2, 3-triazolyl and tetrazolyl, where the heteroaromatic radical may be unsubstituted or may carry 1 to 3 substituents as given above. Preferred substituents on heteroaromatic $R^a$ are selected from halogen, $C_1$-$C_4$-alkyl, $C_1$-$C_4$-alkoxy, fluorinated $C_1$-$C_4$-alkyl and fluorinated $C_1$-$C_4$-alkoxy. Preferably, the heteroaromatic radical is selected from a 5-membered heteroaromatic radical such as pyrrolyl, furanyl, thienyl, pyrazolyl, imidazolyl, oxazolyl, ioxazolyl, thiazolyl and isothiazolyl. Specifically, the heteroaromatic radical is 2-furanyl or 2-thienyl.

In another preferred embodiment, $R^a$ is selected from halogen, fluorinated methyl, $C_1$-$C_4$-alkoxy, fluorinated $C_1$-$C_4$- alkoxy, $C_1$-$C_4$-alkylthio and fluorinated $C_1$-$C_4$-alkylthio, more preferably from halogen, fluorinated methyl, fluorinated $C_1$-$C_4$-alkoxy and fluorinated $C_1$-$C_4$-alkylthio, in particular from halogen, $CH_2F$, $CHF_2$, $CF_3$, $OCH_2F$, $OCHF_2$, $OCF_3$, $SCH_2F$, $SCHF_2$, and $SCF_3$, and specifically from halogen, $CF_3$, $OCF_3$ and $SCF_3$.

In a more preferred embodiment of the invention, $R^a$ is selected from a radical of the formula $R^{a'}$, in particular isopropyl, fluorinated isopropyl (like (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl and 1-(difluoromethyl)-2,2-difluoroethyl), 1-azetidinyl, 1-pyrrolidinyl, 2-methoxymethylpyrrolidin-1-yl, (R)-2-methoxymethylpyrrolidin-1-yl or (S)-2-methoxymethylpyrrolidin-1-yl, further from halogen, in particular bromine, fluorinated methyl, $C_1$-$C_4$-alkoxy and fluorinated $C_1$-$C_4$-alkylthio (such as $CH_2F$, $CHF_2$, $CF_3$, $OCH_2F$, $OCHF_2$, $OCF_3$, $SCH_2F$, $SCHF_2$, and $SCF_3$, and specifically $CF_3$, $OCF_3$ and $SCF_3$), and from a 5-membered heteroaromatic radical, in particular 2-furanyl and 2-thienyl.

Specifically, $R^a$ is selected from isopropyl, 1-azetidinyl, 1-pyrrolidinyl, 2-methoxymethylpyrrolidin-1-yl, (R)-2-methoxymethylpyrrolidin-1-yl, (S)-2-methoxymethylpyrrolidin-1-yl, halogen, in particular bromine, fluorinated methyl, $C_1$-$C_4$-alkoxy, fluorinated $C_1$-$C_4$-alkylthio (such as $CH_2F$, $CHF_2$, $CF_3$, $OCH_2F$, $OCHF_2$, $OCF_3$, $SCH_2F$, $SCHF_2$, and $SCF_3$, and specifically $CF_3$, $OCF_3$ and $SCF_3$), and a 5-membered heteroaromatic radical, in particular 2-furanyl and 2-thienyl.

Preferably, Ar carries one radical $R^a$.

In a very preferred embodiment, Ar is phenyl that carries 1, 2 or 3 substituents selected from the group consisting of halogen, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-alkylthio, fluorinated $C_1$-$C_4$-alkylthio, 1-azetidinyl, 1-pyrrolidinyl, 2-furanyl and 2-thienyl, where the 4 last-mentioned radicals may be substituted by 1 or 2 substituents selected halogen, $C_1$-$C_4$-alkyl, fluorinated $C_1$-$C_4$-alkyl, $C_1$-$C_4$-alkoxy, fluorinated $C_1$-$C_4$-alkoxy and $C_1$-$C_4$-alkoxy-$C_1$-$C_4$-alkyl.

More preferably, Ar is phenyl that carries one radical $R^a$ in the 4-position of the phenyl ring, where $R^a$ is a radical of the formula $R^{a'}$ which is selected from isopropyl, fluorinated isopropyl (like (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl and 1-(difluoromethyl)-2,2-difluoroethyl), 1-azetidinyl, 1-pyrrolidinyl, 2-methoxymethylpyrrolidin-1-yl, (R)-2-methoxymethylpyrrolidin-1-yl and (S)-2-methoxymethylpyrrolidin-1-yl, or $R^a$ is halogen, in particular bromine, fluorinated methyl, fluorinated $C_1$-$C_4$-alkoxy, fluorinated $C_1$-$C_4$-alkylthio (such as $CH_2F$, $CHF_2$, $CF_3$, $OCH_2F$, $OCHF_2$, $OCF_3$, $SCH_2F$, $SCHF_2$, and $SCF_3$, and specifically $CF_3$, $OCF_3$ and $SCF_3$), 2-furanyl or 2-thienyl.

Specifically, Ar is phenyl that carries one radical $R^a$ in the 4-position of the phenyl ring, where $R^a$ is selected from isopropyl, 1-azetidinyl, 1-pyrrolidinyl, 2-methoxymethylpyrrolidin-1-yl, (R)-2-methoxymethylpyrrolidin-1-yl, (S)-2-methoxymethylpyrrolidin-1-yl, halogen, in particular bromine, fluorinated methyl, fluorinated $C_1$-$C_4$-alkoxy, fluorinated $C_1$-$C_4$-alkylthio (such as $CH_2F$, $CHF_2$, $CF_3$, $OCH_2F$, $OCHF_2$, $OCF_3$, $SCH_2F$, $SCHF_2$, and $SCF_3$, and specifically $CF_3$, $OCF_3$ and $SCF_3$), 2-furanyl and 2-thienyl.

Particularly preferred compounds I are those of formulae I.a, I.b, I.c and I.d, wherein $R^1$ and Ar have the above-defined meanings. Preferred meanings of $R^1$ and Ar are as defined above.

Examples of preferred compounds which are represented by the formulae I.a, I.b, I.c and I.d are the individual compounds compiled in table A, where the variables Ar and $R^1$ have the meanings given in one row of table A.

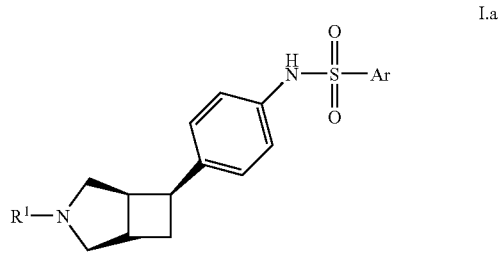

I.a

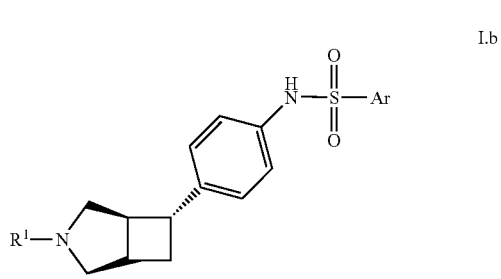

I.b

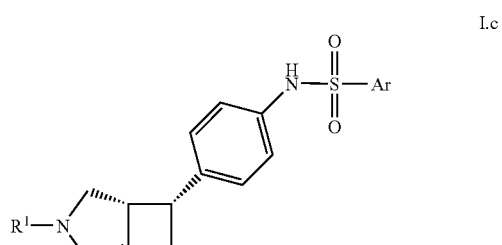

I.c

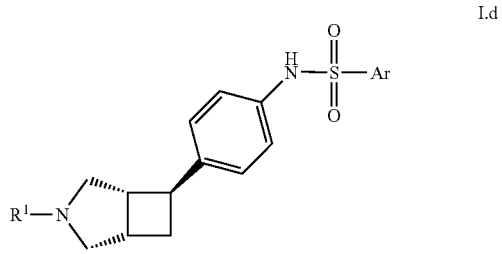

I.d

Examples of preferred compounds which are represented by the formulae I.a, I.b, I.c and I.d are the individual compounds I.a, I.b, I.c and I.d compiled above, where the variables Ar and $R^1$ have the meanings given in one row of table A:

TABLE A

| No. | R¹ | Ar |
|---|---|---|
| 1. | propyl | 4-methylphenyl |
| 2. | propyl | 4-ethylphenyl |
| 3. | propyl | 4-propylphenyl |
| 4. | propyl | 4-isopropylphenyl |
| 5. | propyl | 4-sec-butylphenyl |
| 6. | propyl | 4-isobutylphenyl |
| 7. | propyl | 4-(1,1-dimethylpropyl)-phenyl |
| 8. | propyl | 4-vinylphenyl |
| 9. | propyl | 4-isopropenylphenyl |
| 10. | propyl | 4-fluorophenyl |
| 11. | propyl | 4-chlorophenyl |
| 12. | propyl | 4-bromophenyl |
| 13. | propyl | 4-(fluoromethyl)phenyl |
| 14. | propyl | 3-(fluoromethyl)phenyl |
| 15. | propyl | 2-(fluoromethyl)phenyl |
| 16. | propyl | 4-(difluoromethyl)phenyl |
| 17. | propyl | 3-(difluoromethyl)phenyl |
| 18. | propyl | 2-(difluoromethyl)phenyl |
| 19. | propyl | 4-(trifluoromethyl)phenyl |
| 20. | propyl | 3-(trifluoromethyl)phenyl |
| 21. | propyl | 2-(trifluoromethyl)phenyl |
| 22. | propyl | 4-(1-fluoroethyl)-phenyl |
| 23. | propyl | 4-((S)-1-fluoroethyl)-phenyl |
| 24. | propyl | 4-((R)-1-fluoroethyl)-phenyl |
| 25. | propyl | 4-(2-fluoroethyl)-phenyl |
| 26. | propyl | 4-(1,1-difluoroethyl)-phenyl |
| 27. | propyl | 4-(2,2-difluoroethyl)-phenyl |
| 28. | propyl | 4-(2,2,2-trifluoroethyl)-phenyl |
| 29. | propyl | 4-(3-fluoropropyl)-phenyl |
| 30. | propyl | 4-(2-fluoropropyl)-phenyl |
| 31. | propyl | 4-((S)-2-fluoropropyl)-phenyl |
| 32. | propyl | 4-((R)-2-fluoropropyl)-phenyl |
| 33. | propyl | 4-(3,3-difluoropropyl)-phenyl |
| 34. | propyl | 4-(3,3,3-trifluoropropyl)-phenyl |
| 35. | propyl | 4-(1-fluoro-1-methylethyl)-phenyl |
| 36. | propyl | 4-(2-fluoro-1-methylethyl)-phenyl |
| 37. | propyl | 4-((S)-2-fluoro-1-methylethyl)-phenyl |
| 38. | propyl | 4-((R)-2-fluoro-1-methylethyl)-phenyl |
| 39. | propyl | 4-(2,2-difluoro-1-methylethyl)-phenyl |
| 40. | propyl | 4-((S)-2,2-difluoro-1-methylethyl)-phenyl |
| 41. | propyl | 4-((R)-2,2-difluoro-1-methylethyl)-phenyl |
| 42. | propyl | 4-(2,2,2-trifluoro-1-methylethyl)-phenyl |
| 43. | propyl | 4-((S)-2,2,2-trifluoro-1-methylethyl)-phenyl |
| 44. | propyl | 4-((R)-2,2,2-trifluoro-1-methylethyl)-phenyl |
| 45. | propyl | 4-(2-fluoro-1-fluoromethylethyl)-phenyl |
| 46. | propyl | 4-(1-difluoromethyl-2,2-difluoroethyl)-phenyl |
| 47. | propyl | 4-(1,1-dimethyl-2-fluoroethyl)-phenyl |
| 48. | propyl | 4-methoxyphenyl |
| 49. | propyl | 4-ethoxyphenyl |
| 50. | propyl | 4-propoxyphenyl |
| 51. | propyl | 4-isopropoxyphenyl |
| 52. | propyl | 4-butoxyphenyl |
| 53. | propyl | 4-(fluoromethoxy)-phenyl |
| 54. | propyl | 4-(difluoromethoxy)-phenyl |
| 55. | propyl | 4-(trifluoromethoxy)-phenyl |
| 56. | propyl | 3-(trifluoromethoxy)-phenyl |
| 57. | propyl | 4-(2-fluoroethoxy)-phenyl |
| 58. | propyl | 4-(2,2-difluoroethoxy)-phenyl |
| 59. | propyl | 4-(2,2,2-trifluoroethoxy)-phenyl |
| 60. | propyl | 4-(1,1,2,2-tetrafluoroethoxy)-phenyl |
| 61. | propyl | 4-cyclopropylphenyl |
| 62. | propyl | 4-cyclobutylphenyl |
| 63. | propyl | 4-cyclopentylphenyl |
| 64. | propyl | 4-(2,2-difluorocyclopropyl)-phenyl |
| 65. | propyl | 3,4-difluorophenyl |
| 66. | propyl | 4-bromo-3-fluorophenyl |
| 67. | propyl | 4-bromo-2-fluorophenyl |
| 68. | propyl | 4-bromo-2,5-difluorophenyl |
| 69. | propyl | 2-fluoro-4-isopropylphenyl |
| 70. | propyl | 3-fluoro-4-isopropylphenyl |
| 71. | propyl | 4-(1-hydroxy-1-methylethyl)-phenyl |
| 72. | propyl | 4-(2-hydroxy-2-methylpropyl)-phenyl |
| 73. | propyl | 4-acetylphenyl |
| 74. | propyl | 4-carboxyphenyl |
| 75. | propyl | 4-cyanophenyl |
| 76. | propyl | 4-hydroxyphenyl |
| 77. | propyl | 4-(O-benzyl)-phenyl |

TABLE A-continued

| No. | R¹ | Ar |
|---|---|---|
| 78. | propyl | 4-(2-methoxyethoxy)-phenyl |
| 79. | propyl | 4-(CH₂—N(CH₃)₂)-phenyl |
| 80. | propyl | 4-(NH—CO—NH₂)-phenyl |
| 81. | propyl | 4-(methylsulfanyl)-phenyl |
| 82. | propyl | 4-(fluoromethylsulfanyl)-phenyl |
| 83. | propyl | 4-(difluoromethylsulfanyl)-phenyl |
| 84. | propyl | 4-(trifluoromethylsulfanyl)-phenyl |
| 85. | propyl | 4-(methylsulfonyl)-phenyl |
| 86. | propyl | 4-(N-methoxy-N-methyl-amino)-phenyl |
| 87. | propyl | 4-(methoxyamino)-phenyl |
| 88. | propyl | 4-(ethoxyamino)-phenyl |
| 89. | propyl | 4-(N-methylaminooxy)-phenyl |
| 90. | propyl | 4-(N,N-dimethylaminooxy)-phenyl |
| 91. | propyl | 4-(azetidin-1-yl)-phenyl |
| 92. | propyl | 4-(2-methylazetidin-1-yl)-phenyl |
| 93. | propyl | 4-((S)-2-methylazetidin-1-yl)-phenyl |
| 94. | propyl | 4-((R)-2-methylazetidin-1-yl)-phenyl |
| 95. | propyl | 4-(3-fluoroazetidin-1-yl)-phenyl |
| 96. | propyl | 4-(3-methoxyazetidin-1-yl)-phenyl |
| 97. | propyl | 4-(3-hydroxyazetidin-1-yl)-phenyl |
| 98. | propyl | 4-(pyrrolidin-1-yl)-phenyl |
| 99. | propyl | 4-(pyrrolidin-2-yl)-phenyl |
| 100. | propyl | 4-((S)-pyrrolidin-2-yl)-phenyl |
| 101. | propyl | 4-((R)-pyrrolidin-2-yl)-phenyl |
| 102. | propyl | 4-(pyrrolidin-3-yl)-phenyl |
| 103. | propyl | 4-((S)-pyrrolidin-3-yl)-phenyl |
| 104. | propyl | 4-((R)-pyrrolidin-3-yl)-phenyl |
| 105. | propyl | 4-(2-fluoropyrrolidin-1-yl)-phenyl |
| 106. | propyl | 4-((S)-2-fluoropyrrolidin-1-yl)-phenyl |
| 107. | propyl | 4-((R)-2-fluoropyrrolidin-1-yl)-phenyl |
| 108. | propyl | 4-(3-fluoropyrrolidin-1-yl)-phenyl |
| 109. | propyl | 4-((S)-3-fluoropyrrolidin-1-yl)-phenyl |
| 110. | propyl | 4-((R)-3-fluoropyrrolidin-1-yl)-phenyl |
| 111. | propyl | 4-(2,2-difluoropyrrolidin-1-yl)-phenyl |
| 112. | propyl | 4-(3,3-difluoropyrrolidin-1-yl)-phenyl |
| 113. | propyl | 4-(2-methylpyrrolidin-1-yl)-phenyl |
| 114. | propyl | 4-((S)-2-methylpyrrolidin-1-yl)-phenyl |
| 115. | propyl | 4-((R)-2-methylpyrrolidin-1-yl)-phenyl |
| 116. | propyl | 4-(3-methylpyrrolidin-1-yl)-phenyl |
| 117. | propyl | 4-((S)-3-methylpyrrolidin-1-yl)-phenyl |
| 118. | propyl | 4-((R)-3-methylpyrrolidin-1-yl)-phenyl |
| 119. | propyl | 4-(1-methylpyrrolidin-2-yl)-phenyl |
| 120. | propyl | 4-((S)-1-methylpyrrolidin-2-yl)-phenyl |
| 121. | propyl | 4-((R)-1-methylpyrrolidin-2-yl)-phenyl |
| 122. | propyl | 4-(1-methylpyrrolidin-3-yl)-phenyl |
| 123. | propyl | 4-((S)-1-methylpyrrolidin-3-yl)-phenyl |
| 124. | propyl | 4-((R)-1-methylpyrrolidin-3-yl)-phenyl |
| 125. | propyl | 4-(2,2-dimethylpyrrolidin-1-yl)-phenyl |
| 126. | propyl | 4-(3,3-dimethylpyrrolidin-1-yl)-phenyl |
| 127. | propyl | 4-(2-trifluoromethylpyrrolidin-1-yl)-phenyl |
| 128. | propyl | 4-((S)-2-trifluoromethylpyrrolidin-1-yl)-phenyl |
| 129. | propyl | 4-((R)-2-trifluoromethylpyrrolidin-1-yl)-phenyl |
| 130. | propyl | 4-(3-trifluoromethylpyrrolidin-1-yl)-phenyl |
| 131. | propyl | 4-((S)-3-trifluoromethylpyrrolidin-1-yl)-phenyl |
| 132. | propyl | 4-((R)-3-trifluoromethylpyrrolidin-1-yl)-phenyl |
| 133. | propyl | 4-(2-methoxymethylpyrrolidin-1-yl)-phenyl |
| 134. | propyl | 4-((S)-2-methoxymethylpyrrolidin-1-yl)-phenyl |
| 135. | propyl | 4-((R)-2-methoxymethylpyrrolidin-1-yl)-phenyl |
| 136. | propyl | 4-(2-oxopyrrolidin-1-yl)-phenyl |
| 137. | propyl | 4-(2-oxo-oxazolidin-3-yl)-phenyl |
| 138. | propyl | 4-(piperidin-1-yl)-phenyl |
| 139. | propyl | 4-(2-methylpiperidin-1-yl)-phenyl |
| 140. | propyl | 4-((S)-2-methylpiperidin-1-yl)-phenyl |
| 141. | propyl | 4-((R)-2-methylpiperidin-1-yl)-phenyl |
| 142. | propyl | 4-(piperazin-1-yl)-phenyl |
| 143. | propyl | 4-(4-methylpiperazin-1-yl)-phenyl |
| 144. | propyl | 4-(morpholin-4-yl)-phenyl |
| 145. | propyl | 4-(thiomorpholin-4-yl)-phenyl |
| 146. | propyl | 4-(1-oxo-thiomorpholin-4-yl)-phenyl |
| 147. | propyl | 4-(1,1-dioxo-thiomorpholin-4-yl)-phenyl |
| 148. | propyl | 4-(pyrrol-1-yl)-phenyl |
| 149. | propyl | 4-(pyrrol-2-yl)-phenyl |
| 150. | propyl | 4-(pyrrol-3-yl)-phenyl |
| 151. | propyl | 4-(1-methylpyrrol-2-yl)-phenyl |
| 152. | propyl | 4-(1-methylpyrrol-3-yl)-phenyl |
| 153. | propyl | 4-(furan-2-yl)-phenyl |
| 154. | propyl | 4-(furan-3-yl)-phenyl |

TABLE A-continued

| No. | R¹ | Ar |
|---|---|---|
| 155. | propyl | 4-(thiophen-2-yl)-phenyl |
| 156. | propyl | 4-(thiophen-3-yl)-phenyl |
| 157. | propyl | 4-(5-propylthien-2-yl)-phenyl |
| 158. | propyl | 4-(pyrazol-1-yl)-phenyl |
| 159. | propyl | 4-(pyrazol-3-yl)-phenyl |
| 160. | propyl | 4-(pyrazol-4-yl)-phenyl |
| 161. | propyl | 4-(1-methyl-1H-pyrazol-4-yl)-phenyl |
| 162. | propyl | 4-(1-ethyl-1H-pyrazol-4-yl)-phenyl |
| 163. | propyl | 4-(1-methyl-1H-pyrazol-5-yl)-phenyl |
| 164. | propyl | 4-(1H-imidazol-2-yl)-phenyl |
| 165. | propyl | 4-(imidazol-1-yl)-phenyl |
| 166. | propyl | 4-(1-methylimidazol-2-yl)-phenyl |
| 167. | propyl | 4-(oxazol-2-yl)-phenyl |
| 168. | propyl | 4-(oxazol-4-yl)-phenyl |
| 169. | propyl | 4-(oxazol-5-yl)-phenyl |
| 170. | propyl | 4-(isoxazol-3-yl)-phenyl |
| 171. | propyl | 4-(isoxazol-4-yl)-phenyl |
| 172. | propyl | 4-(isoxazol-5-yl)-phenyl |
| 173. | propyl | 4-([1,2,3]-triazol-1-yl)-phenyl |
| 174. | propyl | 4-([1,2,4]-triazol-1-yl)-phenyl |
| 175. | propyl | 4-([1,2,3]-triazol-2-yl)-phenyl |
| 176. | propyl | 4-(4H-[1,2,4]-triazol-3-yl)-phenyl |
| 177. | propyl | 4-([1,2,4]-triazol-4-yl)-phenyl |
| 178. | propyl | 4-(2H-[1,2,3]-triazol-4-yl)-phenyl |
| 179. | propyl | 4-(4-methyl-4H-[1,2,4]-triazol-3-yl)-phenyl |
| 180. | propyl | 4-(2-methyl-2H-[1,2,3]-triazol-4-yl)-phenyl |
| 181. | propyl | 4-([1,3,4]-oxadiazol-2-yl)-phenyl |
| 182. | propyl | 4-([1,2,4]-oxadiazol-3-yl)-phenyl |
| 183. | propyl | 4-([1,2,4]-oxadiazol-5-yl)-phenyl |
| 184. | propyl | 4-([1,2,3]-oxadiazol-4-yl)-phenyl |
| 185. | propyl | 4-([1,2,3]-oxadiazol-5-yl)-phenyl |
| 186. | propyl | 4-([1,2,3]-thiadiazol-4-yl)-phenyl |
| 187. | propyl | 4-(1H-tetrazol-5-yl)-phenyl |
| 188. | propyl | 4-(tetrazol-1-yl)-phenyl |
| 189. | propyl | 4-(2-methyl-2H-tetrazol-5-yl)-phenyl |
| 190. | propyl | 4-(1-methyl-1H-tetrazol-5-yl)-phenyl |
| 191. | propyl | 4-furazan-3-yl-phenyl |
| 192. | propyl | 4-(pyrid-2-yl)-phenyl |
| 193. | propyl | 4-(pyrid-3-yl)-phenyl |
| 194. | propyl | 4-(pyrid-4-yl)-phenyl |
| 195. | propyl | 4-(pyrimidin-2-yl)-phenyl |
| 196. | propyl | 4-(pyrimidin-4-yl)-phenyl |
| 197. | propyl | 4-(pyrimidin-5-yl)-phenyl |
| 198. | propyl | 5-isopropylthiophen-2-yl |
| 199. | propyl | 2-chlorothiophen-5-yl |
| 200. | propyl | 2,5-dichlorothiophen-4-yl |
| 201. | propyl | 2,3-dichlorothiophen-5-yl |
| 202. | propyl | 2-chloro-3-nitrothiophen-5-yl |
| 203. | propyl | 2-(phenylsulfonyl)-thiophen-5-yl |
| 204. | propyl | 2-(pyridin-2-yl)thiophen-5-yl |
| 205. | propyl | 2-(5-(trifluoromethyl)isoxazol-3-yl)-thiophen-5-yl |
| 206. | propyl | 2-(2-methylthiazol-4-yl)-thiophen-5-yl |
| 207. | propyl | 1-methyl-1H-imidazol-4-yl |
| 208. | propyl | 1,2-dimethyl-1H-imidazol-4-yl |
| 209. | propyl | 3,5-dimethylisoxazol-4-yl |
| 210. | propyl | thiazol-2-yl |
| 211. | propyl | 4-methylthiazol-2-yl |
| 212. | propyl | 4-isopropylthiazol-2-yl |
| 213. | propyl | 4-trifluoromethylthiazol-2-yl |
| 214. | propyl | 5-methylthiazol-2-yl |
| 215. | propyl | 5-isopropylthiazol-2-yl |
| 216. | propyl | 5-trifluoromethylthiazol-2-yl |
| 217. | propyl | 2,4-dimethylthiazol-5-yl |
| 218. | propyl | 2-acetamido-4-methylthiazol-5-yl |
| 219. | propyl | 4H-[1,2,4]triazol-3-yl |
| 220. | propyl | 5-methyl-4H-[1,2,4]triazol-3-yl |
| 221. | propyl | 4-methyl-4H-[1,2,4]triazol-3-yl |
| 222. | propyl | 5-isopropyl-4H-[1,2,4]triazol-3-yl |
| 223. | propyl | 5-trifluoromethyl-4H-[1,2,4]triazol-3-yl |
| 224. | propyl | 4,5-dimethyl-4H-[1,2,4]triazol-3-yl |
| 225. | propyl | 5-isopropyl-4-methyl-4H-[1,2,4]triazol-3-yl |
| 226. | propyl | 5-trifluoromethyl-4-methyl-4H-[1,2,4]triazol-3-yl |
| 227. | propyl | [1,3,4]thiadiazol-2-yl |
| 228. | propyl | 5-methyl-[1,3,4]thiadiazol-2-yl |
| 229. | propyl | 5-isopropyl-[1,3,4]thiadiazol-2-yl |
| 230. | propyl | 5-trifluoromethyl-[1,3,4]thiadiazol-2-yl |
| 231. | propyl | 3-bromo-2-chloropyrid-5-yl |

TABLE A-continued

| No. | R¹ | Ar |
|---|---|---|
| 232. | propyl | 2-(4-morpholino)-pyrid-5-yl |
| 233. | propyl | 2-phenoxypyrid-5-yl |
| 234. | propyl | (2-isopropyl)-pyrimidin-5-yl |
| 235. | propyl | (5-isopropyl)-pyrimidin-2-yl |
| 236. | propyl | 8-quinolyl |
| 237. | propyl | 5-isoquinolyl |
| 238. | propyl | 2-(trifluoroacetyl)-1,2,3,4-tetrahydroisoquinolin-7-yl |
| 239. | propyl | 5-chloro-3-methylbenzothiophen-2-yl |
| 240. | propyl | 3,4-dihydro-4-methyl-2H-benzo[b][1,4]oxazinyl |
| 241. | propyl | benzothiazol-6-yl |
| 242. | propyl | benzo[2,1,3]oxadiazol-4-yl |
| 243. | propyl | 5-chlorobenzo[2,1,3]oxadiazol-4-yl |
| 244. | propyl | 7-chlorobenzo[2,1,3]oxadiazol-4-yl |
| 245. | propyl | benzo[2,1,3]thiadiazol-4-yl |
| 246. | ethyl | 4-methylphenyl |
| 247. | ethyl | 4-ethylphenyl |
| 248. | ethyl | 4-propylphenyl |
| 249. | ethyl | 4-isopropylphenyl |
| 250. | ethyl | 4-sec-butylphenyl |
| 251. | ethyl | 4-isobutylphenyl |
| 252. | ethyl | 4-(1,1-dimethylpropyl)-phenyl |
| 253. | ethyl | 4-vinylphenyl |
| 254. | ethyl | 4-isopropenylphenyl |
| 255. | ethyl | 4-fluorophenyl |
| 256. | ethyl | 4-chlorophenyl |
| 257. | ethyl | 4-bromophenyl |
| 258. | ethyl | 4-(fluoromethyl)phenyl |
| 259. | ethyl | 3-(fluoromethyl)phenyl |
| 260. | ethyl | 2-(fluoromethyl)phenyl |
| 261. | ethyl | 4-(difluoromethyl)phenyl |
| 262. | ethyl | 3-(difluoromethyl)phenyl |
| 263. | ethyl | 2-(difluoromethyl)phenyl |
| 264. | ethyl | 4-(trifluoromethyl)phenyl |
| 265. | ethyl | 3-(trifluoromethyl)phenyl |
| 266. | ethyl | 2-(trifluoromethyl)phenyl |
| 267. | ethyl | 4-(1-fluoroethyl)-phenyl |
| 268. | ethyl | 4-((S)-1-fluoroethyl)-phenyl |
| 269. | ethyl | 4-((R)-1-fluoroethyl)-phenyl |
| 270. | ethyl | 4-(2-fluoroethyl)-phenyl |
| 271. | ethyl | 4-(1,1-difluoroethyl)-phenyl |
| 272. | ethyl | 4-(2,2-difluoroethyl)-phenyl |
| 273. | ethyl | 4-(2,2,2-trifluoroethyl)-phenyl |
| 274. | ethyl | 4-(3-fluoropropyl)-phenyl |
| 275. | ethyl | 4-(2-fluoropropyl)-phenyl |
| 276. | ethyl | 4-((S)-2-fluoropropyl)-phenyl |
| 277. | ethyl | 4-((R)-2-fluoropropyl)-phenyl |
| 278. | ethyl | 4-(3,3-difluoropropyl)-phenyl |
| 279. | ethyl | 4-(3,3,3-trifluoropropyl)-phenyl |
| 280. | ethyl | 4-(1-fluoro-1-methylethyl)-phenyl |
| 281. | ethyl | 4-(2-fluoro-1-methylethyl)-phenyl |
| 282. | ethyl | 4-((S)-2-fluoro-1-methylethyl)-phenyl |
| 283. | ethyl | 4-((R)-2-fluoro-1-methylethyl)-phenyl |
| 284. | ethyl | 4-(2,2-difluoro-1-methylethyl)-phenyl |
| 285. | ethyl | 4-((S)-2,2-difluoro-1-methylethyl)-phenyl |
| 286. | ethyl | 4-((R)-2,2-difluoro-1-methylethyl)-phenyl |
| 287. | ethyl | 4-(2,2,2-trifluoro-1-methylethyl)-phenyl |
| 288. | ethyl | 4-((S)-2,2,2-trifluoro-1-methylethyl)-phenyl |
| 289. | ethyl | 4-((R)-2,2,2-trifluoro-1-methylethyl)-phenyl |
| 290. | ethyl | 4-(2-fluoro-1-fluoromethylethyl)-phenyl |
| 291. | ethyl | 4-(1-difluoromethyl-2,2-difluoroethyl)-phenyl |
| 292. | ethyl | 4-(1,1-dimethyl-2-fluoroethyl)-phenyl |
| 293. | ethyl | 4-methoxyphenyl |
| 294. | ethyl | 4-ethoxyphenyl |
| 295. | ethyl | 4-propoxyphenyl |
| 296. | ethyl | 4-isopropoxyphenyl |
| 297. | ethyl | 4-butoxyphenyl |
| 298. | ethyl | 4-(fluoromethoxy)-phenyl |
| 299. | ethyl | 4-(difluoromethoxy)-phenyl |
| 300. | ethyl | 4-(trifluoromethoxy)-phenyl |
| 301. | ethyl | 3-(trifluoromethoxy)-phenyl |
| 302. | ethyl | 4-(2-fluoroethoxy)-phenyl |
| 303. | ethyl | 4-(2,2-difluoroethoxy)-phenyl |
| 304. | ethyl | 4-(2,2,2-trifluoroethoxy)-phenyl |
| 305. | ethyl | 4-(1,1,2,2-tetrafluoroethoxy)-phenyl |
| 306. | ethyl | 4-cyclopropylphenyl |
| 307. | ethyl | 4-cyclobutylphenyl |
| 308. | ethyl | 4-cyclopentylphenyl |

TABLE A-continued

| No. | R¹ | Ar |
|---|---|---|
| 309. | ethyl | 4-(2,2-difluorocyclopropyl)-phenyl |
| 310. | ethyl | 3,4-difluorophenyl |
| 311. | ethyl | 4-bromo-3-fluorophenyl |
| 312. | ethyl | 4-bromo-2-fluorophenyl |
| 313. | ethyl | 4-bromo-2,5-difluorophenyl |
| 314. | ethyl | 2-fluoro-4-isopropylphenyl |
| 315. | ethyl | 3-fluoro-4-isopropylphenyl |
| 316. | ethyl | 4-(1-hydroxy-1-methylethyl)-phenyl |
| 317. | ethyl | 4-(2-hydroxy-2-methylpropyl)-phenyl |
| 318. | ethyl | 4-acetylphenyl |
| 319. | ethyl | 4-carboxyphenyl |
| 320. | ethyl | 4-cyanophenyl |
| 321. | ethyl | 4-hydroxyphenyl |
| 322. | ethyl | 4-(O-benzyl)-phenyl |
| 323. | ethyl | 4-(2-methoxyethoxy)-phenyl |
| 324. | ethyl | 4-($CH_2$—$N(CH_3)_2$)-phenyl |
| 325. | ethyl | 4-(NH—CO—$NH_2$)-phenyl |
| 326. | ethyl | 4-(methylsulfanyl)-phenyl |
| 327. | ethyl | 4-(fluoromethylsulfanyl)-phenyl |
| 328. | ethyl | 4-(difluoromethylsulfanyl)-phenyl |
| 329. | ethyl | 4-(trifluoromethylsulfanyl)-phenyl |
| 330. | ethyl | 4-(methylsulfonyl)-phenyl |
| 331. | ethyl | 4-(N-methoxy-N-methyl-amino)-phenyl |
| 332. | ethyl | 4-(methoxyamino)-phenyl |
| 333. | ethyl | 4-(ethoxyamino)-phenyl |
| 334. | ethyl | 4-(N-methylaminooxy)-phenyl |
| 335. | ethyl | 4-(N,N-dimethylaminooxy)-phenyl |
| 336. | ethyl | 4-(azetidin-1-yl)-phenyl |
| 337. | ethyl | 4-(2-methylazetidin-1-yl)-phenyl |
| 338. | ethyl | 4-((S)-2-methylazetidin-1-yl)-phenyl |
| 339. | ethyl | 4-((R)-2-methylazetidin-1-yl)-phenyl |
| 340. | ethyl | 4-(3-fluoroazetidin-1-yl)-phenyl |
| 341. | ethyl | 4-(3-methoxyazetidin-1-yl)-phenyl |
| 342. | ethyl | 4-(3-hydroxyazetidin-1-yl)-phenyl |
| 343. | ethyl | 4-(pyrrolidin-1-yl)-phenyl |
| 344. | ethyl | 4-(pyrrolidin-2-yl)-phenyl |
| 345. | ethyl | 4-((S)-pyrrolidin-2-yl)-phenyl |
| 346. | ethyl | 4-((R)-pyrrolidin-2-yl)-phenyl |
| 347. | ethyl | 4-(pyrrolidin-3-yl)-phenyl |
| 348. | ethyl | 4-((S)-pyrrolidin-3-yl)-phenyl |
| 349. | ethyl | 4-((R)-pyrrolidin-3-yl)-phenyl |
| 350. | ethyl | 4-(2-fluoropyrrolidin-1-yl)-phenyl |
| 351. | ethyl | 4-((S)-2-fluoropyrrolidin-1-yl)-phenyl |
| 352. | ethyl | 4-((R)-2-fluoropyrrolidin-1-yl)-phenyl |
| 353. | ethyl | 4-(3-fluoropyrrolidin-1-yl)-phenyl |
| 354. | ethyl | 4-((S)-3-fluoropyrrolidin-1-yl)-phenyl |
| 355. | ethyl | 4-((R)-3-fluoropyrrolidin-1-yl)-phenyl |
| 356. | ethyl | 4-(2,2-difluoropyrrolidin-1-yl)-phenyl |
| 357. | ethyl | 4-(3,3-difluoropyrrolidin-1-yl)-phenyl |
| 358. | ethyl | 4-(2-methylpyrrolidin-1-yl)-phenyl |
| 359. | ethyl | 4-((S)-2-methylpyrrolidin-1-yl)-phenyl |
| 360. | ethyl | 4-((R)-2-methylpyrrolidin-1-yl)-phenyl |
| 361. | ethyl | 4-(3-methylpyrrolidin-1-yl)-phenyl |
| 362. | ethyl | 4-((S)-3-methylpyrrolidin-1-yl)-phenyl |
| 363. | ethyl | 4-((R)-3-methylpyrrolidin-1-yl)-phenyl |
| 364. | ethyl | 4-(1-methylpyrrolidin-2-yl)-phenyl |
| 365. | ethyl | 4-((S)-1-methylpyrrolidin-2-yl)-phenyl |
| 366. | ethyl | 4-((R)-1-methylpyrrolidin-2-yl)-phenyl |
| 367. | ethyl | 4-(1-methylpyrrolidin-3-yl)-phenyl |
| 368. | ethyl | 4-((S)-1-methylpyrrolidin-3-yl)-phenyl |
| 369. | ethyl | 4-((R)-1-methylpyrrolidin-3-yl)-phenyl |
| 370. | ethyl | 4-(2,2-dimethylpyrrolidin-1-yl)-phenyl |
| 371. | ethyl | 4-(3,3-dimethylpyrrolidin-1-yl)-phenyl |
| 372. | ethyl | 4-(2-trifluoromethylpyrrolidin-1-yl)-phenyl |
| 373. | ethyl | 4-((S)-2-trifluoromethylpyrrolidin-1-yl)-phenyl |
| 374. | ethyl | 4-((R)-2-trifluoromethylpyrrolidin-1-yl)-phenyl |
| 375. | ethyl | 4-(3-trifluoromethylpyrrolidin-1-yl)-phenyl |
| 376. | ethyl | 4-((S)-3-trifluoromethylpyrrolidin-1-yl)-phenyl |
| 377. | ethyl | 4-((R)-3-trifluoromethylpyrrolidin-1-yl)-phenyl |
| 378. | ethyl | 4-(2-methoxymethylpyrrolidin-1-yl)-phenyl |
| 379. | ethyl | 4-((S)-2-methoxymethylpyrrolidin-1-yl)-phenyl |
| 380. | ethyl | 4-((R)-2-methoxymethylpyrrolidin-1-yl)-phenyl |
| 381. | ethyl | 4-(2-oxopyrrolidin-1-yl)-phenyl |
| 382. | ethyl | 4-(2-oxo-oxazolidin-3-yl)-phenyl |
| 383. | ethyl | 4-(piperidin-1-yl)-phenyl |
| 384. | ethyl | 4-(2-methylpiperidin-1-yl)-phenyl |
| 385. | ethyl | 4-((S)-2-methylpiperidin-1-yl)-phenyl |

TABLE A-continued

| No. | R¹ | Ar |
|---|---|---|
| 386. | ethyl | 4-((R)-2-methylpiperidin-1-yl)-phenyl |
| 387. | ethyl | 4-(piperazin-1-yl)-phenyl |
| 388. | ethyl | 4-(4-methylpiperazin-1-yl)-phenyl |
| 389. | ethyl | 4-(morpholin-4-yl)-phenyl |
| 390. | ethyl | 4-(thiomorpholin-4-yl)-phenyl |
| 391. | ethyl | 4-(1-oxo-thiomorpholin-4-yl)-phenyl |
| 392. | ethyl | 4-(1,1-dioxo-thiomorpholin-4-yl)-phenyl |
| 393. | ethyl | 4-(pyrrol-1-yl)-phenyl |
| 394. | ethyl | 4-(pyrrol-2-yl)-phenyl |
| 395. | ethyl | 4-(pyrrol-3-yl)-phenyl |
| 396. | ethyl | 4-(1-methylpyrrol-2-yl)-phenyl |
| 397. | ethyl | 4-(1-methylpyrrol-3-yl)-phenyl |
| 398. | ethyl | 4-(furan-2-yl)-phenyl |
| 399. | ethyl | 4-(furan-3-yl)-phenyl |
| 400. | ethyl | 4-(thiophen-2-yl)-phenyl |
| 401. | ethyl | 4-(thiophen-3-yl)-phenyl |
| 402. | ethyl | 4-(5-propylthien-2-yl)-phenyl |
| 403. | ethyl | 4-(pyrazol-1-yl)-phenyl |
| 404. | ethyl | 4-(pyrazol-3-yl)-phenyl |
| 405. | ethyl | 4-(pyrazol-4-yl)-phenyl |
| 406. | ethyl | 4-(1-methyl-1H-pyrazol-4-yl)-phenyl |
| 407. | ethyl | 4-(1-ethyl-1H-pyrazol-4-yl)-phenyl |
| 408. | ethyl | 4-(1-methyl-1H-pyrazol-5-yl)-phenyl |
| 409. | ethyl | 4-(1H-imidazol-2-yl)-phenyl |
| 410. | ethyl | 4-(imidazol-1-yl)-phenyl |
| 411. | ethyl | 4-(1-methylimidazol-2-yl)-phenyl |
| 412. | ethyl | 4-(oxazol-2-yl)-phenyl |
| 413. | ethyl | 4-(oxazol-4-yl)-phenyl |
| 414. | ethyl | 4-(oxazol-5-yl)-phenyl |
| 415. | ethyl | 4-(isoxazol-3-yl)-phenyl |
| 416. | ethyl | 4-(isoxazol-4-yl)-phenyl |
| 417. | ethyl | 4-(isoxazol-5-yl)-phenyl |
| 418. | ethyl | 4-([1,2,3]-triazol-1-yl)-phenyl |
| 419. | ethyl | 4-([1,2,4]-triazol-1-yl)-phenyl |
| 420. | ethyl | 4-([1,2,3]-triazol-2-yl)-phenyl |
| 421. | ethyl | 4-(4H-[1,2,4]-triazol-3-yl)-phenyl |
| 422. | ethyl | 4-([1,2,4]-triazol-4-yl)-phenyl |
| 423. | ethyl | 4-(2H-[1,2,3]-triazol-4-yl)-phenyl |
| 424. | ethyl | 4-(4-methyl-4H-[1,2,4]-triazol-3-yl)-phenyl |
| 425. | ethyl | 4-(2-methyl-2H-[1,2,3]-triazol-4-yl)-phenyl |
| 426. | ethyl | 4-([1,3,4]-oxadiazol-2-yl)-phenyl |
| 427. | ethyl | 4-([1,2,4]-oxadiazol-3-yl)-phenyl |
| 428. | ethyl | 4-([1,2,4]-oxadiazol-5-yl)-phenyl |
| 429. | ethyl | 4-([1,2,3]-oxadiazol-4-yl)-phenyl |
| 430. | ethyl | 4-([1,2,3]-oxadiazol-5-yl)-phenyl |
| 431. | ethyl | 4-([1,2,3]-thiadiazol-4-yl)-phenyl |
| 432. | ethyl | 4-(1H-tetrazol-5-yl)-phenyl |
| 433. | ethyl | 4-(tetrazol-1-yl)-phenyl |
| 434. | ethyl | 4-(2-methyl-2H-tetrazol-5-yl)-phenyl |
| 435. | ethyl | 4-(1-methyl-1H-tetrazol-5-yl)-phenyl |
| 436. | ethyl | 4-furazan-3-yl-phenyl |
| 437. | ethyl | 4-(pyrid-2-yl)-phenyl |
| 438. | ethyl | 4-(pyrid-3-yl)-phenyl |
| 439. | ethyl | 4-(pyrid-4-yl)-phenyl |
| 440. | ethyl | 4-(pyrimidin-2-yl)-phenyl |
| 441. | ethyl | 4-(pyrimidin-4-yl)-phenyl |
| 442. | ethyl | 4-(pyrimidin-5-yl)-phenyl |
| 443. | ethyl | 5-isopropylthiophen-2-yl |
| 444. | ethyl | 2-chlorothiophen-5-yl |
| 445. | ethyl | 2,5-dichlorothiophen-4-yl |
| 446. | ethyl | 2,3-dichlorothiophen-5-yl |
| 447. | ethyl | 2-chloro-3-nitrothiophen-5-yl |
| 448. | ethyl | 2-(phenylsulfonyl)-thiophen-5-yl |
| 449. | ethyl | 2-(pyridin-2-yl)thiophen-5-yl |
| 450. | ethyl | 2-(5-(trifluoromethyl)isoxazol-3-yl)-thiophen-5-yl |
| 451. | ethyl | 2-(2-methylthiazol-4-yl)-thiophen-5-yl |
| 452. | ethyl | 1-methyl-1H-imidazol-4-yl |
| 453. | ethyl | 1,2-dimethyl-1H-imidazol-4-yl |
| 454. | ethyl | 3,5-dimethylisoxazol-4-yl |
| 455. | ethyl | thiazol-2-yl |
| 456. | ethyl | 4-methylthiazol-2-yl |
| 457. | ethyl | 4-isopropylthiazol-2-yl |
| 458. | ethyl | 4-trifluoromethylthiazol-2-yl |
| 459. | ethyl | 5-methylthiazol-2-yl |
| 460. | ethyl | 5-isopropylthiazol-2-yl |
| 461. | ethyl | 5-trifluoromethylthiazol-2-yl |
| 462. | ethyl | 2,4-dimethylthiazol-5-yl |

TABLE A-continued

| No. | R¹ | Ar |
|---|---|---|
| 463. | ethyl | 2-acetamido-4-methylthiazol-5-yl |
| 464. | ethyl | 4H-[1,2,4]triazol-3-yl |
| 465. | ethyl | 5-methyl-4H-[1,2,4]triazol-3-yl |
| 466. | ethyl | 4-methyl-4H-[1,2,4]triazol-3-yl |
| 467. | ethyl | 5-isopropyl-4H-[1,2,4]triazol-3-yl |
| 468. | ethyl | 5-trifluoromethyl-4H-[1,2,4]triazol-3-yl |
| 469. | ethyl | 4,5-dimethyl-4H-[1,2,4]triazol-3-yl |
| 470. | ethyl | 5-isopropyl-4-methyl-4H-[1,2,4]triazol-3-yl |
| 471. | ethyl | 5-trifluoromethyl-4-methyl-4H-[1,2,4]triazol-3-yl |
| 472. | ethyl | [1,3,4]thiadiazol-2-yl |
| 473. | ethyl | 5-methyl-[1,3,4]thiadiazol-2-yl |
| 474. | ethyl | 5-isopropyl-[1,3,4]thiadiazol-2-yl |
| 475. | ethyl | 5-trifluoromethyl-[1,3,4]thiadiazol-2-yl |
| 476. | ethyl | 3-bromo-2-chloropyrid-5-yl |
| 477. | ethyl | 2-(4-morpholino)-pyrid-5-yl |
| 478. | ethyl | 2-phenoxypyrid-5-yl |
| 479. | ethyl | (2-isopropyl)-pyrimidin-5-yl |
| 480. | ethyl | (5-isopropyl)-pyrimidin-2-yl |
| 481. | ethyl | 8-quinolyl |
| 482. | ethyl | 5-isoquinolyl |
| 483. | ethyl | 2-(trifluoroacetyl)-1,2,3,4-tetrahydroisoquinolin-7-yl |
| 484. | ethyl | 5-chloro-3-methylbenzothiophen-2-yl |
| 485. | ethyl | 3,4-dihydro-4-methyl-2H-benzo[b][1,4]oxazinyl |
| 486. | ethyl | benzothiazol-6-yl |
| 487. | ethyl | benzo[2,1,3]oxadiazol-4-yl |
| 488. | ethyl | 5-chlorobenzo[2,1,3]oxadiazol-4-yl |
| 489. | ethyl | 7-chlorobenzo[2,1,3]oxadiazol-4-yl |
| 490. | ethyl | benzo[2,1,3]thiadiazol-4-yl |
| 491. | methyl | 4-methylphenyl |
| 492. | methyl | 4-ethylphenyl |
| 493. | methyl | 4-propylphenyl |
| 494. | methyl | 4-isopropylphenyl |
| 495. | methyl | 4-sec-butylphenyl |
| 496. | methyl | 4-isobutylphenyl |
| 497. | methyl | 4-(1,1-dimethylpropyl)-phenyl |
| 498. | methyl | 4-vinylphenyl |
| 499. | methyl | 4-isopropenylphenyl |
| 500. | methyl | 4-fluorophenyl |
| 501. | methyl | 4-chlorophenyl |
| 502. | methyl | 4-bromophenyl |
| 503. | methyl | 4-(fluoromethyl)phenyl |
| 504. | methyl | 3-(fluoromethyl)phenyl |
| 505. | methyl | 2-(fluoromethyl)phenyl |
| 506. | methyl | 4-(difluoromethyl)phenyl |
| 507. | methyl | 3-(difluoromethyl)phenyl |
| 508. | methyl | 2-(difluoromethyl)phenyl |
| 509. | methyl | 4-(trifluoromethyl)phenyl |
| 510. | methyl | 3-(trifluoromethyl)phenyl |
| 511. | methyl | 2-(trifluoromethyl)phenyl |
| 512. | methyl | 4-(1-fluoroethyl)-phenyl |
| 513. | methyl | 4-((S)-1-fluoroethyl)-phenyl |
| 514. | methyl | 4-((R)-1-fluoroethyl)-phenyl |
| 515. | methyl | 4-(2-fluoroethyl)-phenyl |
| 516. | methyl | 4-(1,1-difluoroethyl)-phenyl |
| 517. | methyl | 4-(2,2-difluoroethyl)-phenyl |
| 518. | methyl | 4-(2,2,2-trifluoroethyl)-phenyl |
| 519. | methyl | 4-(3-fluoropropyl)-phenyl |
| 520. | methyl | 4-(2-fluoropropyl)-phenyl |
| 521. | methyl | 4-((S)-2-fluoropropyl)-phenyl |
| 522. | methyl | 4-((R)-2-fluoropropyl)-phenyl |
| 523. | methyl | 4-(3,3-difluoropropyl)-phenyl |
| 524. | methyl | 4-(3,3,3-trifluoropropyl)-phenyl |
| 525. | methyl | 4-(1-fluoro-1-methylethyl)-phenyl |
| 526. | methyl | 4-(2-fluoro-1-methylethyl)-phenyl |
| 527. | methyl | 4-((S)-2-fluoro-1-methylethyl)-phenyl |
| 528. | methyl | 4-((R)-2-fluoro-1-methylethyl)-phenyl |
| 529. | methyl | 4-(2,2-difluoro-1-methylethyl)-phenyl |
| 530. | methyl | 4-((S)-2,2-difluoro-1-methylethyl)-phenyl |
| 531. | methyl | 4-((R)-2,2-difluoro-1-methylethyl)-phenyl |
| 532. | methyl | 4-(2,2,2-trifluoro-1-methylethyl)-phenyl |
| 533. | methyl | 4-((S)-2,2,2-trifluoro-1-methylethyl)-phenyl |
| 534. | methyl | 4-((R)-2,2,2-trifluoro-1-methylethyl)-phenyl |
| 535. | methyl | 4-(2-fluoro-1-fluoromethylethyl)-phenyl |
| 536. | methyl | 4-(1-difluoromethyl-2,2-difluoroethyl)-phenyl |
| 537. | methyl | 4-(1,1-dimethyl-2-fluoroethyl)-phenyl |
| 538. | methyl | 4-methoxyphenyl |
| 539. | methyl | 4-ethoxyphenyl |

TABLE A-continued

| No. | R¹ | Ar |
|---|---|---|
| 540. | methyl | 4-propoxyphenyl |
| 541. | methyl | 4-isopropoxyphenyl |
| 542. | methyl | 4-butoxyphenyl |
| 543. | methyl | 4-(fluoromethoxy)-phenyl |
| 544. | methyl | 4-(difluoromethoxy)-phenyl |
| 545. | methyl | 4-(trifluoromethoxy)-phenyl |
| 546. | methyl | 3-(trifluoromethoxy)-phenyl |
| 547. | methyl | 4-(2-fluoroethoxy)-phenyl |
| 548. | methyl | 4-(2,2-difluoroethoxy)-phenyl |
| 549. | methyl | 4-(2,2,2-trifluoroethoxy)-phenyl |
| 550. | methyl | 4-(1,1,2,2-tetrafluoroethoxy)-phenyl |
| 551. | methyl | 4-cyclopropylphenyl |
| 552. | methyl | 4-cyclobutylphenyl |
| 553. | methyl | 4-cyclopentylphenyl |
| 554. | methyl | 4-(2,2-difluorocyclopropyl)-phenyl |
| 555. | methyl | 3,4-difluorophenyl |
| 556. | methyl | 4-bromo-3-fluorophenyl |
| 557. | methyl | 4-bromo-2-fluorophenyl |
| 558. | methyl | 4-bromo-2,5-difluorophenyl |
| 559. | methyl | 2-fluoro-4-isopropylphenyl |
| 560. | methyl | 3-fluoro-4-isopropylphenyl |
| 561. | methyl | 4-(1-hydroxy-1-methylethyl)-phenyl |
| 562. | methyl | 4-(2-hydroxy-2-methylpropyl)-phenyl |
| 563. | methyl | 4-acetylphenyl |
| 564. | methyl | 4-carboxyphenyl |
| 565. | methyl | 4-cyanophenyl |
| 566. | methyl | 4-hydroxyphenyl |
| 567. | methyl | 4-(O-benzyl)-phenyl |
| 568. | methyl | 4-(2-methoxyethoxy)-phenyl |
| 569. | methyl | 4-(CH$_2$—N(CH$_3$)$_2$)-phenyl |
| 570. | methyl | 4-(NH—CO—NH$_2$)-phenyl |
| 571. | methyl | 4-(methylsulfanyl)-phenyl |
| 572. | methyl | 4-(fluoromethylsulfanyl)-phenyl |
| 573. | methyl | 4-(difluoromethylsulfanyl)-phenyl |
| 574. | methyl | 4-(trifluoromethylsulfanyl)-phenyl |
| 575. | methyl | 4-(methylsulfonyl)-phenyl |
| 576. | methyl | 4-(N-methoxy-N-methyl-amino)-phenyl |
| 577. | methyl | 4-(methoxyamino)-phenyl |
| 578. | methyl | 4-(ethoxyamino)-phenyl |
| 579. | methyl | 4-(N-methylaminooxy)-phenyl |
| 580. | methyl | 4-(N,N-dimethylaminooxy)-phenyl |
| 581. | methyl | 4-(azetidin-1-yl)-phenyl |
| 582. | methyl | 4-(2-methylazetidin-1-yl)-phenyl |
| 583. | methyl | 4-((S)-2-methylazetidin-1-yl)-phenyl |
| 584. | methyl | 4-((R)-2-methylazetidin-1-yl)-phenyl |
| 585. | methyl | 4-(3-fluoroazetidin-1-yl)-phenyl |
| 586. | methyl | 4-(3-methoxyazetidin-1-yl)-phenyl |
| 587. | methyl | 4-(3-hydroxyazetidin-1-yl)-phenyl |
| 588. | methyl | 4-(pyrrolidin-1-yl)-phenyl |
| 589. | methyl | 4-(pyrrolidin-2-yl)-phenyl |
| 590. | methyl | 4-((S)-pyrrolidin-2-yl)-phenyl |
| 591. | methyl | 4-((R)-pyrrolidin-2-yl)-phenyl |
| 592. | methyl | 4-(pyrrolidin-3-yl)-phenyl |
| 593. | methyl | 4-((S)-pyrrolidin-3-yl)-phenyl |
| 594. | methyl | 4-((R)-pyrrolidin-3-yl)-phenyl |
| 595. | methyl | 4-(2-fluoropyrrolidin-1-yl)-phenyl |
| 596. | methyl | 4-((S)-2-fluoropyrrolidin-1-yl)-phenyl |
| 597. | methyl | 4-((R)-2-fluoropyrrolidin-1-yl)-phenyl |
| 598. | methyl | 4-(3-fluoropyrrolidin-1-yl)-phenyl |
| 599. | methyl | 4-((S)-3-fluoropyrrolidin-1-yl)-phenyl |
| 600. | methyl | 4-((R)-3-fluoropyrrolidin-1-yl)-phenyl |
| 601. | methyl | 4-(2,2-difluoropyrrolidin-1-yl)-phenyl |
| 602. | methyl | 4-(3,3-difluoropyrrolidin-1-yl)-phenyl |
| 603. | methyl | 4-(2-methylpyrrolidin-1-yl)-phenyl |
| 604. | methyl | 4-((S)-2-methylpyrrolidin-1-yl)-phenyl |
| 605. | methyl | 4-((R)-2-methylpyrrolidin-1-yl)-phenyl |
| 606. | methyl | 4-(3-methylpyrrolidin-1-yl)-phenyl |
| 607. | methyl | 4-((S)-3-methylpyrrolidin-1-yl)-phenyl |
| 608. | methyl | 4-((R)-3-methylpyrrolidin-1-yl)-phenyl |
| 609. | methyl | 4-(1-methylpyrrolidin-2-yl)-phenyl |
| 610. | methyl | 4-((S)-1-methylpyrrolidin-2-yl)-phenyl |
| 611. | methyl | 4-((R)-1-methylpyrrolidin-2-yl)-phenyl |
| 612. | methyl | 4-(1-methylpyrrolidin-3-yl)-phenyl |
| 613. | methyl | 4-((S)-1-methylpyrrolidin-3-yl)-phenyl |
| 614. | methyl | 4-((R)-1-methylpyrrolidin-3-yl)-phenyl |
| 615. | methyl | 4-(2,2-dimethylpyrrolidin-1-yl)-phenyl |
| 616. | methyl | 4-(3,3-dimethylpyrrolidin-1-yl)-phenyl |

TABLE A-continued

| No. | R¹ | Ar |
|---|---|---|
| 617. | methyl | 4-(2-trifluoromethylpyrrolidin-1-yl)-phenyl |
| 618. | methyl | 4-((S)-2-trifluoromethylpyrrolidin-1-yl)-phenyl |
| 619. | methyl | 4-((R)-2-trifluoromethylpyrrolidin-1-yl)-phenyl |
| 620. | methyl | 4-(3-trifluoromethylpyrrolidin-1-yl)-phenyl |
| 621. | methyl | 4-((S)-3-trifluoromethylpyrrolidin-1-yl)-phenyl |
| 622. | methyl | 4-((R)-3-trifluoromethylpyrrolidin-1-yl)-phenyl |
| 623. | methyl | 4-(2-methoxymethylpyrrolidin-1-yl)-phenyl |
| 624. | methyl | 4-((S)-2-methoxymethylpyrrolidin-1-yl)-phenyl |
| 625. | methyl | 4-((R)-2-methoxymethylpyrrolidin-1-yl)-phenyl |
| 626. | methyl | 4-(2-oxopyrrolidin-1-yl)-phenyl |
| 627. | methyl | 4-(2-oxo-oxazolidin-3-yl)-phenyl |
| 628. | methyl | 4-(piperidin-1-yl)-phenyl |
| 629. | methyl | 4-(2-methylpiperidin-1-yl)-phenyl |
| 630. | methyl | 4-((S)-2-methylpiperidin-1-yl)-phenyl |
| 631. | methyl | 4-((R)-2-methylpiperidin-1-yl)-phenyl |
| 632. | methyl | 4-(piperazin-1-yl)-phenyl |
| 633. | methyl | 4-(4-methylpiperazin-1-yl)-phenyl |
| 634. | methyl | 4-(morpholin-4-yl)-phenyl |
| 635. | methyl | 4-(thiomorpholin-4-yl)-phenyl |
| 636. | methyl | 4-(1-oxo-thiomorpholin-4-yl)-phenyl |
| 637. | methyl | 4-(1,1-dioxo-thiomorpholin-4-yl)-phenyl |
| 638. | methyl | 4-(pyrrol-1-yl)-phenyl |
| 639. | methyl | 4-(pyrrol-2-yl)-phenyl |
| 640. | methyl | 4-(pyrrol-3-yl)-phenyl |
| 641. | methyl | 4-(1-methylpyrrol-2-yl)-phenyl |
| 642. | methyl | 4-(1-methylpyrrol-3-yl)-phenyl |
| 643. | methyl | 4-(furan-2-yl)-phenyl |
| 644. | methyl | 4-(furan-3-yl)-phenyl |
| 645. | methyl | 4-(thiophen-2-yl)-phenyl |
| 646. | methyl | 4-(thiophen-3-yl)-phenyl |
| 647. | methyl | 4-(5-propylthien-2-yl)-phenyl |
| 648. | methyl | 4-(pyrazol-1-yl)-phenyl |
| 649. | methyl | 4-(pyrazol-3-yl)-phenyl |
| 650. | methyl | 4-(pyrazol-4-yl)-phenyl |
| 651. | methyl | 4-(1-methyl-1H-pyrazol-4-yl)-phenyl |
| 652. | methyl | 4-(1-ethyl-1H-pyrazol-4-yl)-phenyl |
| 653. | methyl | 4-(1-methyl-1H-pyrazol-5-yl)-phenyl |
| 654. | methyl | 4-(1H-imidazol-2-yl)-phenyl |
| 655. | methyl | 4-(imidazol-1-yl)-phenyl |
| 656. | methyl | 4-(1-methylimidazol-2-yl)-phenyl |
| 657. | methyl | 4-(oxazol-2-yl)-phenyl |
| 658. | methyl | 4-(oxazol-4-yl)-phenyl |
| 659. | methyl | 4-(oxazol-5-yl)-phenyl |
| 660. | methyl | 4-(isoxazol-3-yl)-phenyl |
| 661. | methyl | 4-(isoxazol-4-yl)-phenyl |
| 662. | methyl | 4-(isoxazol-5-yl)-phenyl |
| 663. | methyl | 4-([1,2,3]-triazol-1-yl)-phenyl |
| 664. | methyl | 4-([1,2,4]-triazol-1-yl)-phenyl |
| 665. | methyl | 4-([1,2,3]-triazol-2-yl)-phenyl |
| 666. | methyl | 4-(4H-[1,2,4]-triazol-3-yl)-phenyl |
| 667. | methyl | 4-([1,2,4]-triazol-4-yl)-phenyl |
| 668. | methyl | 4-(2H-[1,2,3]-triazol-4-yl)-phenyl |
| 669. | methyl | 4-(4-methyl-4H-[1,2,4]-triazol-3-yl)-phenyl |
| 670. | methyl | 4-(2-methyl-2H-[1,2,3]-triazol-4-yl)-phenyl |
| 671. | methyl | 4-([1,3,4]-oxadiazol-2-yl)-phenyl |
| 672. | methyl | 4-([1,2,4]-oxadiazol-3-yl)-phenyl |
| 673. | methyl | 4-([1,2,4]-oxadiazol-5-yl)-phenyl |
| 674. | methyl | 4-([1,2,3]-oxadiazol-4-yl)-phenyl |
| 675. | methyl | 4-([1,2,3]-oxadiazol-5-yl)-phenyl |
| 676. | methyl | 4-([1,2,3]-thiadiazol-4-yl)-phenyl |
| 677. | methyl | 4-(1H-tetrazol-5-yl)-phenyl |
| 678. | methyl | 4-(tetrazol-1-yl)-phenyl |
| 679. | methyl | 4-(2-methyl-2H-tetrazol-5-yl)-phenyl |
| 680. | methyl | 4-(1-methyl-1H-tetrazol-5-yl)-phenyl |
| 681. | methyl | 4-furazan-3-yl-phenyl |
| 682. | methyl | 4-(pyrid-2-yl)-phenyl |
| 683. | methyl | 4-(pyrid-3-yl)-phenyl |
| 684. | methyl | 4-(pyrid-4-yl)-phenyl |
| 685. | methyl | 4-(pyrimidin-2-yl)-phenyl |
| 686. | methyl | 4-(pyrimidin-4-yl)-phenyl |
| 687. | methyl | 4-(pyrimidin-5-yl)-phenyl |
| 688. | methyl | 5-isopropylthiophen-2-yl |
| 689. | methyl | 2-chlorothiophen-5-yl |
| 690. | methyl | 2,5-dichlorothiophen-4-yl |
| 691. | methyl | 2,3-dichlorothiophen-5-yl |
| 692. | methyl | 2-chloro-3-nitrothiophen-5-yl |
| 693. | methyl | 2-(phenylsulfonyl)-thiophen-5-yl |

TABLE A-continued

| No. | R¹ | Ar |
|---|---|---|
| 694. | methyl | 2-(pyridin-2-yl)thiophen-5-yl |
| 695. | methyl | 2-(5-(trifluoromethyl)isoxazol-3-yl)-thiophen-5-yl |
| 696. | methyl | 2-(2-methylthiazol-4-yl)-thiophen-5-yl |
| 697. | methyl | 1-methyl-1H-imidazol-4-yl |
| 698. | methyl | 1,2-dimethyl-1H-imidazol-4-yl |
| 699. | methyl | 3,5-dimethylisoxazol-4-yl |
| 700. | methyl | thiazol-2-yl |
| 701. | methyl | 4-methylthiazol-2-yl |
| 702. | methyl | 4-isopropylthiazol-2-yl |
| 703. | methyl | 4-trifluoromethylthiazol-2-yl |
| 704. | methyl | 5-methylthiazol-2-yl |
| 705. | methyl | 5-isopropylthiazol-2-yl |
| 706. | methyl | 5-trifluoromethylthiazol-2-yl |
| 707. | methyl | 2,4-dimethylthiazol-5-yl |
| 708. | methyl | 2-acetamido-4-methylthiazol-5-yl |
| 709. | methyl | 4H-[1,2,4]triazol-3-yl |
| 710. | methyl | 5-methyl-4H-[1,2,4]triazol-3-yl |
| 711. | methyl | 4-methyl-4H-[1,2,4]triazol-3-yl |
| 712. | methyl | 5-isopropyl-4H-[1,2,4]triazol-3-yl |
| 713. | methyl | 5-trifluoromethyl-4H-[1,2,4]triazol-3-yl |
| 714. | methyl | 4,5-dimethyl-4H-[1,2,4]triazol-3-yl |
| 715. | methyl | 5-isopropyl-4-methyl-4H-[1,2,4]triazol-3-yl |
| 716. | methyl | 5-trifluoromethyl-4-methyl-4H-[1,2,4]triazol-3-yl |
| 717. | methyl | [1,3,4]thiadiazol-2-yl |
| 718. | methyl | 5-methyl-[1,3,4]thiadiazol-2-yl |
| 719. | methyl | 5-isopropyl-[1,3,4]thiadiazol-2-yl |
| 720. | methyl | 5-trifluoromethyl-[1,3,4]thiadiazol-2-yl |
| 721. | methyl | 3-bromo-2-chloropyrid-5-yl |
| 722. | methyl | 2-(4-morpholino)-pyrid-5-yl |
| 723. | methyl | 2-phenoxypyrid-5-yl |
| 724. | methyl | (2-isopropyl)-pyrimidin-5-yl |
| 725. | methyl | (5-isopropyl)-pyrimidin-2-yl |
| 726. | methyl | 8-quinolyl |
| 727. | methyl | 5-isoquinolyl |
| 728. | methyl | 2-(trifluoroacetyl)-1,2,3,4-tetrahydroisoquinolin-7-yl |
| 729. | methyl | 5-chloro-3-methylbenzothiophen-2-yl |
| 730. | methyl | 3,4-dihydro-4-methyl-2H-benzo[b][1,4]oxazinyl |
| 731. | methyl | benzothiazol-6-yl |
| 732. | methyl | benzo[2,1,3]oxadiazol-4-yl |
| 733. | methyl | 5-chlorobenzo[2,1,3]oxadiazol-4-yl |
| 734. | methyl | 7-chlorobenzo[2,1,3]oxadiazol-4-yl |
| 735. | methyl | benzo[2,1,3]thiadiazol-4-yl |
| 736. | H | 4-methylphenyl |
| 737. | H | 4-ethylphenyl |
| 738. | H | 4-propylphenyl |
| 739. | H | 4-isopropylphenyl |
| 740. | H | 4-sec-butylphenyl |
| 741. | H | 4-isobutylphenyl |
| 742. | H | 4-(1,1-dimethylpropyl)-phenyl |
| 743. | H | 4-vinylphenyl |
| 744. | H | 4-isopropenylphenyl |
| 745. | H | 4-fluorophenyl |
| 746. | H | 4-chlorophenyl |
| 747. | H | 4-bromophenyl |
| 748. | H | 4-(fluoromethyl)phenyl |
| 749. | H | 3-(fluoromethyl)phenyl |
| 750. | H | 2-(fluoromethyl)phenyl |
| 751. | H | 4-(difluoromethyl)phenyl |
| 752. | H | 3-(difluoromethyl)phenyl |
| 753. | H | 2-(difluoromethyl)phenyl |
| 754. | H | 4-(trifluoromethyl)phenyl |
| 755. | H | 3-(trifluoromethyl)phenyl |
| 756. | H | 2-(trifluoromethyl)phenyl |
| 757. | H | 4-(1-fluoroethyl)-phenyl |
| 758. | H | 4-((S)-1-fluoroethyl)-phenyl |
| 759. | H | 4-((R)-1-fluoroethyl)-phenyl |
| 760. | H | 4-(2-fluoroethyl)-phenyl |
| 761. | H | 4-(1,1-difluoroethyl)-phenyl |
| 762. | H | 4-(2,2-difluoroethyl)-phenyl |
| 763. | H | 4-(2,2,2-trifluoroethyl)-phenyl |
| 764. | H | 4-(3-fluoropropyl)-phenyl |
| 765. | H | 4-(2-fluoropropyl)-phenyl |
| 766. | H | 4-((S)-2-fluoropropyl)-phenyl |
| 767. | H | 4-((R)-2-fluoropropyl)-phenyl |
| 768. | H | 4-(3,3-difluoropropyl)-phenyl |
| 769. | H | 4-(3,3,3-trifluoropropyl)-phenyl |
| 770. | H | 4-(1-fluoro-1-methylethyl)-phenyl |

TABLE A-continued

| No. | R¹ | Ar |
|---|---|---|
| 771. | H | 4-(2-fluoro-1-methylethyl)-phenyl |
| 772. | H | 4-((S)-2-fluoro-1-methylethyl)-phenyl |
| 773. | H | 4-((R)-2-fluoro-1-methylethyl)-phenyl |
| 774. | H | 4-(2,2-difluoro-1-methylethyl)-phenyl |
| 775. | H | 4-((S)-2,2-difluoro-1-methylethyl)-phenyl |
| 776. | H | 4-((R)-2,2-difluoro-1-methylethyl)-phenyl |
| 777. | H | 4-(2,2,2-trifluoro-1-methylethyl)-phenyl |
| 778. | H | 4-((S)-2,2,2-trifluoro-1-methylethyl)-phenyl |
| 779. | H | 4-((R)-2,2,2-trifluoro-1-methylethyl)-phenyl |
| 780. | H | 4-(2-fluoro-1-fluoromethylethyl)-phenyl |
| 781. | H | 4-(1-difluoromethyl-2,2-difluoroethyl)-phenyl |
| 782. | H | 4-(1,1-dimethyl-2-fluoroethyl)-phenyl |
| 783. | H | 4-methoxyphenyl |
| 784. | H | 4-ethoxyphenyl |
| 785. | H | 4-propoxyphenyl |
| 786. | H | 4-isopropoxyphenyl |
| 787. | H | 4-butoxyphenyl |
| 788. | H | 4-(fluoromethoxy)-phenyl |
| 789. | H | 4-(difluoromethoxy)-phenyl |
| 790. | H | 4-(trifluoromethoxy)-phenyl |
| 791. | H | 3-(trifluoromethoxy)-phenyl |
| 792. | H | 4-(2-fluoroethoxy)-phenyl |
| 793. | H | 4-(2,2-difluoroethoxy)-phenyl |
| 794. | H | 4-(2,2,2-trifluoroethoxy)-phenyl |
| 795. | H | 4-(1,1,2,2-tetrafluoroethoxy)-phenyl |
| 796. | H | 4-cyclopropylphenyl |
| 797. | H | 4-cyclobutylphenyl |
| 798. | H | 4-cyclopentylphenyl |
| 799. | H | 4-(2,2-difluorocyclopropyl)-phenyl |
| 800. | H | 3,4-difluorophenyl |
| 801. | H | 4-bromo-3-fluorophenyl |
| 802. | H | 4-bromo-2-fluorophenyl |
| 803. | H | 4-bromo-2,5-difluorophenyl |
| 804. | H | 2-fluoro-4-isopropylphenyl |
| 805. | H | 3-fluoro-4-isopropylphenyl |
| 806. | H | 4-(1-hydroxy-1-methylethyl)-phenyl |
| 807. | H | 4-(2-hydroxy-2-methylpropyl)-phenyl |
| 808. | H | 4-acetylphenyl |
| 809. | H | 4-carboxyphenyl |
| 810. | H | 4-cyanophenyl |
| 811. | H | 4-hydroxyphenyl |
| 812. | H | 4-(O-benzyl)-phenyl |
| 813. | H | 4-(2-methoxyethoxy)-phenyl |
| 814. | H | 4-(CH₂—N(CH₃)₂)-phenyl |
| 815. | H | 4-(NH—CO—NH₂)-phenyl |
| 816. | H | 4-(methylsulfanyl)-phenyl |
| 817. | H | 4-(fluoromethylsulfanyl)-phenyl |
| 818. | H | 4-(difluoromethylsulfanyl)-phenyl |
| 819. | H | 4-(trifluoromethylsulfanyl)-phenyl |
| 820. | H | 4-(methylsulfonyl)-phenyl |
| 821. | H | 4-(N-methoxy-N-methyl-amino)-phenyl |
| 822. | H | 4-(methoxyamino)-phenyl |
| 823. | H | 4-(ethoxyamino)-phenyl |
| 824. | H | 4-(N-methylaminooxy)-phenyl |
| 825. | H | 4-(N,N-dimethylaminooxy)-phenyl |
| 826. | H | 4-(azetidin-1-yl)-phenyl |
| 827. | H | 4-(2-methylazetidin-1-yl)-phenyl |
| 828. | H | 4-((S)-2-methylazetidin-1-yl)-phenyl |
| 829. | H | 4-((R)-2-methylazetidin-1-yl)-phenyl |
| 830. | H | 4-(3-fluoroazetidin-1-yl)-phenyl |
| 831. | H | 4-(3-methoxyazetidin-1-yl)-phenyl |
| 832. | H | 4-(3-hydroxyazetidin-1-yl)-phenyl |
| 870. | H | 4-((R)-2-methoxymethylpyrrolidin-1-yl)-phenyl |
| 871. | H | 4-(2-oxopyrrolidin-1-yl)-phenyl |
| 872. | H | 4-(2-oxo-oxazolidin-3-yl)-phenyl |
| 873. | H | 4-(piperidin-1-yl)-phenyl |
| 874. | H | 4-(2-methylpiperidin-1-yl)-phenyl |
| 875. | H | 4-((S)-2-methylpiperidin-1-yl)-phenyl |
| 876. | H | 4-((R)-2-methylpiperidin-1-yl)-phenyl |
| 877. | H | 4-(piperazin-1-yl)-phenyl |
| 878. | H | 4-(4-methylpiperazin-1-yl)-phenyl |
| 879. | H | 4-(morpholin-4-yl)-phenyl |
| 880. | H | 4-(thiomorpholin-4-yl)-phenyl |
| 881. | H | 4-(1-oxo-thiomorpholin-4-yl)-phenyl |
| 882. | H | 4-(1,1-dioxo-thiomorpholin-4-yl)-phenyl |
| 883. | H | 4-(pyrrol-1-yl)-phenyl |
| 884. | H | 4-(pyrrol-2-yl)-phenyl |

TABLE A-continued

| No. | R¹ | Ar |
|---|---|---|
| 885. | H | 4-(pyrrol-3-yl)-phenyl |
| 886. | H | 4-(1-methylpyrrol-2-yl)-phenyl |
| 887. | H | 4-(1-methylpyrrol-3-yl)-phenyl |
| 888. | H | 4-(furan-2-yl)-phenyl |
| 889. | H | 4-(furan-3-yl)-phenyl |
| 890. | H | 4-(thiophen-2-yl)-phenyl |
| 891. | H | 4-(thiophen-3-yl)-phenyl |
| 892. | H | 4-(5-propylthien-2-yl)-phenyl |
| 893. | H | 4-(pyrazol-1-yl)-phenyl |
| 894. | H | 4-(pyrazol-3-yl)-phenyl |
| 895. | H | 4-(pyrazol-4-yl)-phenyl |
| 896. | H | 4-(1-methyl-1H-pyrazol-4-yl)-phenyl |
| 897. | H | 4-(1-ethyl-1H-pyrazol-4-yl)-phenyl |
| 898. | H | 4-(1-methyl-1H-pyrazol-5-yl)-phenyl |
| 899. | H | 4-(1H-imidazol-2-yl)-phenyl |
| 900. | H | 4-(imidazol-1-yl)-phenyl |
| 901. | H | 4-(1-methylimidazol-2-yl)-phenyl |
| 902. | H | 4-(oxazol-2-yl)-phenyl |
| 903. | H | 4-(oxazol-4-yl)-phenyl |
| 904. | H | 4-(oxazol-5-yl)-phenyl |
| 905. | H | 4-(isoxazol-3-yl)-phenyl |
| 906. | H | 4-(isoxazol-4-yl)-phenyl |
| 907. | H | 4-(isoxazol-5-yl)-phenyl |
| 908. | H | 4-([1,2,3]-triazol-1-yl)-phenyl |
| 909. | H | 4-([1,2,4]-triazol-1-yl)-phenyl |
| 910. | H | 4-([1,2,3]-triazol-2-yl)-phenyl |
| 911. | H | 4-(4H-[1,2,4]-triazol-3-yl)-phenyl |
| 912. | H | 4-([1,2,4]-triazol-4-yl)-phenyl |
| 913. | H | 4-(2H-[1,2,3]-triazol-4-yl)-phenyl |
| 914. | H | 4-(4-methyl-4H-[1,2,4]-triazol-3-yl)-phenyl |
| 915. | H | 4-(2-methyl-2H-[1,2,3]-triazol-4-yl)-phenyl |
| 916. | H | 4-([1,3,4]-oxadiazol-2-yl)-phenyl |
| 917. | H | 4-([1,2,4]-oxadiazol-3-yl)-phenyl |
| 918. | H | 4-([1,2,4]-oxadiazol-5-yl)-phenyl |
| 919. | H | 4-([1,2,3]-oxadiazol-4-yl)-phenyl |
| 920. | H | 4-([1,2,3]-oxadiazol-5-yl)-phenyl |
| 921. | H | 4-([1,2,3]-thiadiazol-4-yl)-phenyl |
| 922. | H | 4-(1H-tetrazol-5-yl)-phenyl |
| 923. | H | 4-(tetrazol-1-yl)-phenyl |
| 924. | H | 4-(2-methyl-2H-tetrazol-5-yl)-phenyl |
| 925. | H | 4-(1-methyl-1H-tetrazol-5-yl)-phenyl |
| 926. | H | 4-furazan-3-yl-phenyl |
| 927. | H | 4-(pyrid-2-yl)-phenyl |
| 928. | H | 4-(pyrid-3-yl)-phenyl |
| 929. | H | 4-(pyrid-4-yl)-phenyl |
| 930. | H | 4-(pyrimidin-2-yl)-phenyl |
| 931. | H | 4-(pyrimidin-4-yl)-phenyl |
| 932. | H | 4-(pyrimidin-5-yl)-phenyl |
| 933. | H | 5-isopropylthiophen-2-yl |
| 934. | H | 2-chlorothiophen-5-yl |
| 935. | H | 2,5-dichlorothiophen-4-yl |
| 936. | H | 2,3-dichlorothiophen-5-yl |
| 937. | H | 2-chloro-3-nitrothiophen-5-yl |
| 938. | H | 2-(phenylsulfonyl)-thiophen-5-yl |
| 939. | H | 2-(pyridin-2-yl)thiophen-5-yl |
| 940. | H | 2-(5-(trifluoromethyl)isoxazol-3-yl)-thiophen-5-yl |
| 941. | H | 2-(2-methylthiazol-4-yl)-thiophen-5-yl |
| 942. | H | 1-methyl-1H-imidazol-4-yl |
| 943. | H | 1,2-dimethyl-1H-imidazol-4-yl |
| 944. | H | 3,5-dimethylisoxazol-4-yl |
| 945. | H | thiazol-2-yl |
| 946. | H | 4-methylthiazol-2-yl |
| 947. | H | 4-isopropylthiazol-2-yl |
| 948. | H | 4-trifluoromethylthiazol-2-yl |
| 949. | H | 5-methylthiazol-2-yl |
| 950. | H | 5-isopropylthiazol-2-yl |
| 951. | H | 5-trifluoromethylthiazol-2-yl |
| 952. | H | 2,4-dimethylthiazol-5-yl |
| 953. | H | 2-acetamido-4-methylthiazol-5-yl |
| 954. | H | 4H-[1,2,4]triazol-3-yl |
| 955. | H | 5-methyl-4H-[1,2,4]triazol-3-yl |
| 956. | H | 4-methyl-4H-[1,2,4]triazol-3-yl |
| 957. | H | 5-isopropyl-4H-[1,2,4]triazol-3-yl |
| 958. | H | 5-trifluoromethyl-4H-[1,2,4]triazol-3-yl |
| 959. | H | 4,5-dimethyl-4H-[1,2,4]triazol-3-yl |
| 960. | H | 5-isopropyl-4-methyl-4H-[1,2,4]triazol-3-yl |
| 961. | H | 5-trifluoromethyl-4-methyl-4H-[1,2,4]triazol-3-yl |

TABLE A-continued

| No. | R¹ | Ar |
|---|---|---|
| 962. | H | [1,3,4]thiadiazol-2-yl |
| 963. | H | 5-methyl-[1,3,4]thiadiazol-2-yl |
| 964. | H | 5-isopropyl-[1,3,4]thiadiazol-2-yl |
| 965. | H | 5-trifluoromethyl-[1,3,4]thiadiazol-2-yl |
| 966. | H | 3-bromo-2-chloropyrid-5-yl |
| 967. | H | 2-(4-morpholino)-pyrid-5-yl |
| 968. | H | 2-phenoxypyrid-5-yl |
| 969. | H | (2-isopropyl)-pyrimidin-5-yl |
| 970. | H | (5-isopropyl)-pyrimidin-2-yl |
| 971. | H | 8-quinolyl |
| 972. | H | 5-isoquinolyl |
| 973. | H | 2-(trifluoroacetyl)-1,2,3,4-tetrahydroisoquinolin-7-yl |
| 974. | H | 5-chloro-3-methylbenzothiophen-2-yl |
| 975. | H | 3,4-dihydro-4-methyl-2H-benzo[b][1,4]oxazinyl |
| 976. | H | benzothiazol-6-yl |
| 977. | H | benzo[2,1,3]oxadiazol-4-yl |
| 978. | H | 5-chlorobenzo[2,1,3]oxadiazol-4-yl |
| 979. | H | 7-chlorobenzo[2,1,3]oxadiazol-4-yl |
| 980. | H | benzo[2,1,3]thiadiazol-4-yl |
| 981. | 3-fluoropropyl | 4-methylphenyl |
| 982. | 3-fluoropropyl | 4-ethylphenyl |
| 983. | 3-fluoropropyl | 4-propylphenyl |
| 984. | 3-fluoropropyl | 4-isopropylphenyl |
| 985. | 3-fluoropropyl | 4-sec-butylphenyl |
| 986. | 3-fluoropropyl | 4-isobutylphenyl |
| 987. | 3-fluoropropyl | 4-(1,1-dimethylpropyl)-phenyl |
| 988. | 3-fluoropropyl | 4-vinylphenyl |
| 989. | 3-fluoropropyl | 4-isopropenylphenyl |
| 990. | 3-fluoropropyl | 4-fluorophenyl |
| 991. | 3-fluoropropyl | 4-chlorophenyl |
| 992. | 3-fluoropropyl | 4-bromophenyl |
| 993. | 3-fluoropropyl | 4-(fluoromethyl)phenyl |
| 994. | 3-fluoropropyl | 3-(fluoromethyl)phenyl |
| 995. | 3-fluoropropyl | 2-(fluoromethyl)phenyl |
| 996. | 3-fluoropropyl | 4-(difluoromethyl)phenyl |
| 997. | 3-fluoropropyl | 3-(difluoromethyl)phenyl |
| 998. | 3-fluoropropyl | 2-(difluoromethyl)phenyl |
| 999. | 3-fluoropropyl | 4-(trifluoromethyl)phenyl |
| 1000. | 3-fluoropropyl | 3-(trifluoromethyl)phenyl |
| 1001. | 3-fluoropropyl | 2-(trifluoromethyl)phenyl |
| 1002. | 3-fluoropropyl | 4-(1-fluoroethyl)-phenyl |
| 1003. | 3-fluoropropyl | 4-((S)-1-fluoroethyl)-phenyl |
| 1004. | 3-fluoropropyl | 4-((R)-1-fluoroethyl)-phenyl |
| 1005. | 3-fluoropropyl | 4-(2-fluoroethyl)-phenyl |
| 1006. | 3-fluoropropyl | 4-(1,1-difluoroethyl)-phenyl |
| 1007. | 3-fluoropropyl | 4-(2,2-difluoroethyl)-phenyl |
| 1008. | 3-fluoropropyl | 4-(2,2,2-trifluoroethyl)-phenyl |
| 1009. | 3-fluoropropyl | 4-(3-fluoropropyl)-phenyl |
| 1010. | 3-fluoropropyl | 4-(2-fluoropropyl)-phenyl |
| 1011. | 3-fluoropropyl | 4-((S)-2-fluoropropyl)-phenyl |
| 1012. | 3-fluoropropyl | 4-((R)-2-fluoropropyl)-phenyl |
| 1013. | 3-fluoropropyl | 4-(3,3-difluoropropyl)-phenyl |
| 1014. | 3-fluoropropyl | 4-(3,3,3-trifluoropropyl)-phenyl |
| 1015. | 3-fluoropropyl | 4-(1-fluoro-1-methylethyl)-phenyl |
| 1016. | 3-fluoropropyl | 4-(2-fluoro-1-methylethyl)-phenyl |
| 1017. | 3-fluoropropyl | 4-((S)-2-fluoro-1-methylethyl)-phenyl |
| 1018. | 3-fluoropropyl | 4-((R)-2-fluoro-1-methylethyl)-phenyl |
| 1019. | 3-fluoropropyl | 4-(2,2-difluoro-1-methylethyl)-phenyl |
| 1020. | 3-fluoropropyl | 4-((S)-2,2-difluoro-1-methylethyl)-phenyl |
| 1021. | 3-fluoropropyl | 4-((R)-2,2-difluoro-1-methylethyl)-phenyl |
| 1022. | 3-fluoropropyl | 4-(2,2,2-trifluoro-1-methylethyl)-phenyl |
| 1023. | 3-fluoropropyl | 4-((S)-2,2,2-trifluoro-1-methylethyl)-phenyl |
| 1024. | 3-fluoropropyl | 4-((R)-2,2,2-trifluoro-1-methylethyl)-phenyl |
| 1025. | 3-fluoropropyl | 4-(2-fluoro-1-fluoromethylethyl)-phenyl |
| 1026. | 3-fluoropropyl | 4-(1-difluoromethyl-2,2-difluoroethyl)-phenyl |
| 1027. | 3-fluoropropyl | 4-(1,1-dimethyl-2-fluoroethyl)-phenyl |
| 1028. | 3-fluoropropyl | 4-methoxyphenyl |
| 1029. | 3-fluoropropyl | 4-ethoxyphenyl |
| 1030. | 3-fluoropropyl | 4-propoxyphenyl |
| 1031. | 3-fluoropropyl | 4-isopropoxyphenyl |
| 1032. | 3-fluoropropyl | 4-butoxyphenyl |
| 1033. | 3-fluoropropyl | 4-(fluoromethoxy)-phenyl |
| 1034. | 3-fluoropropyl | 4-(difluoromethoxy)-phenyl |
| 1035. | 3-fluoropropyl | 4-(trifluoromethoxy)-phenyl |
| 1036. | 3-fluoropropyl | 3-(trifluoromethoxy)-phenyl |
| 1037. | 3-fluoropropyl | 4-(2-fluoroethoxy)-phenyl |
| 1038. | 3-fluoropropyl | 4-(2,2-difluoroethoxy)-phenyl |

TABLE A-continued

| No. | R¹ | Ar |
|---|---|---|
| 1039. | 3-fluoropropyl | 4-(2,2,2-trifluoroethoxy)-phenyl |
| 1040. | 3-fluoropropyl | 4-(1,1,2,2-tetrafluoroethoxy)-phenyl |
| 1041. | 3-fluoropropyl | 4-cyclopropylphenyl |
| 1042. | 3-fluoropropyl | 4-cyclobutylphenyl |
| 1043. | 3-fluoropropyl | 4-cyclopentylphenyl |
| 1044. | 3-fluoropropyl | 4-(2,2-difluorocyclopropyl)-phenyl |
| 1045. | 3-fluoropropyl | 3,4-difluorophenyl |
| 1046. | 3-fluoropropyl | 4-bromo-3-fluorophenyl |
| 1047. | 3-fluoropropyl | 4-bromo-2-fluorophenyl |
| 1048. | 3-fluoropropyl | 4-bromo-2,5-difluorophenyl |
| 1049. | 3-fluoropropyl | 2-fluoro-4-isopropylphenyl |
| 1050. | 3-fluoropropyl | 3-fluoro-4-isopropylphenyl |
| 1051. | 3-fluoropropyl | 4-(1-hydroxy-1-methylethyl)-phenyl |
| 1052. | 3-fluoropropyl | 4-(2-hydroxy-2-methylpropyl)-phenyl |
| 1053. | 3-fluoropropyl | 4-acetylphenyl |
| 1054. | 3-fluoropropyl | 4-carboxyphenyl |
| 1055. | 3-fluoropropyl | 4-cyanophenyl |
| 1056. | 3-fluoropropyl | 4-hydroxyphenyl |
| 1057. | 3-fluoropropyl | 4-(O-benzyl)-phenyl |
| 1058. | 3-fluoropropyl | 4-(2-methoxyethoxy)-phenyl |
| 1059. | 3-fluoropropyl | 4-(CH$_2$—N(CH$_3$)$_2$)-phenyl |
| 1060. | 3-fluoropropyl | 4-(NH—CO—NH$_2$)-phenyl |
| 1061. | 3-fluoropropyl | 4-(methylsulfanyl)-phenyl |
| 1062. | 3-fluoropropyl | 4-(fluoromethylsulfanyl)-phenyl |
| 1063. | 3-fluoropropyl | 4-(difluoromethylsulfanyl)-phenyl |
| 1064. | 3-fluoropropyl | 4-(trifluoromethylsulfanyl)-phenyl |
| 1065. | 3-fluoropropyl | 4-(methylsulfonyl)-phenyl |
| 1066. | 3-fluoropropyl | 4-(N-methoxy-N-methyl-amino)-phenyl |
| 1067. | 3-fluoropropyl | 4-(methoxyamino)-phenyl |
| 1068. | 3-fluoropropyl | 4-(ethoxyamino)-phenyl |
| 1069. | 3-fluoropropyl | 4-(N-methylaminooxy)-phenyl |
| 1070. | 3-fluoropropyl | 4-(N,N-dimethylaminooxy)-phenyl |
| 1071. | 3-fluoropropyl | 4-(azetidin-1-yl)-phenyl |
| 1072. | 3-fluoropropyl | 4-(2-methylazetidin-1-yl)-phenyl |
| 1073. | 3-fluoropropyl | 4-((S)-2-methylazetidin-1-yl)-phenyl |
| 1074. | 3-fluoropropyl | 4-((R)-2-methylazetidin-1-yl)-phenyl |
| 1075. | 3-fluoropropyl | 4-(3-fluoroazetidin-1-yl)-phenyl |
| 1076. | 3-fluoropropyl | 4-(3-methoxyazetidin-1-yl)-phenyl |
| 1077. | 3-fluoropropyl | 4-(3-hydroxyazetidin-1-yl)-phenyl |
| 1078. | 3-fluoropropyl | 4-(pyrrolidin-1-yl)-phenyl |
| 1079. | 3-fluoropropyl | 4-(pyrrolidin-2-yl)-phenyl |
| 1080. | 3-fluoropropyl | 4-((S)-pyrrolidin-2-yl)-phenyl |
| 1081. | 3-fluoropropyl | 4-((R)-pyrrolidin-2-yl)-phenyl |
| 1082. | 3-fluoropropyl | 4-(pyrrolidin-3-yl)-phenyl |
| 1083. | 3-fluoropropyl | 4-((S)-pyrrolidin-3-yl)-phenyl |
| 1084. | 3-fluoropropyl | 4-((R)-pyrrolidin-3-yl)-phenyl |
| 1085. | 3-fluoropropyl | 4-(2-fluoropyrrolidin-1-yl)-phenyl |
| 1086. | 3-fluoropropyl | 4-((S)-2-fluoropyrrolidin-1-yl)-phenyl |
| 1087. | 3-fluoropropyl | 4-((R)-2-fluoropyrrolidin-1-yl)-phenyl |
| 1088. | 3-fluoropropyl | 4-(3-fluoropyrrolidin-1-yl)-phenyl |
| 1089. | 3-fluoropropyl | 4-((S)-3-fluoropyrrolidin-1-yl)-phenyl |
| 1090. | 3-fluoropropyl | 4-((R)-3-fluoropyrrolidin-1-yl)-phenyl |
| 1091. | 3-fluoropropyl | 4-(2,2-difluoropyrrolidin-1-yl)-phenyl |
| 1092. | 3-fluoropropyl | 4-(3,3-difluoropyrrolidin-1-yl)-phenyl |
| 1093. | 3-fluoropropyl | 4-(2-methylpyrrolidin-1-yl)-phenyl |
| 1094. | 3-fluoropropyl | 4-((S)-2-methylpyrrolidin-1-yl)-phenyl |
| 1095. | 3-fluoropropyl | 4-((R)-2-methylpyrrolidin-1-yl)-phenyl |
| 1096. | 3-fluoropropyl | 4-(3-methylpyrrolidin-1-yl)-phenyl |
| 1097. | 3-fluoropropyl | 4-((S)-3-methylpyrrolidin-1-yl)-phenyl |
| 1098. | 3-fluoropropyl | 4-((R)-3-methylpyrrolidin-1-yl)-phenyl |
| 1099. | 3-fluoropropyl | 4-(1-methylpyrrolidin-2-yl)-phenyl |
| 1100. | 3-fluoropropyl | 4-((S)-1-methylpyrrolidin-2-yl)-phenyl |
| 1101. | 3-fluoropropyl | 4-((R)-1-methylpyrrolidin-2-yl)-phenyl |
| 1102. | 3-fluoropropyl | 4-(1-methylpyrrolidin-3-yl)-phenyl |
| 1103. | 3-fluoropropyl | 4-((S)-1-methylpyrrolidin-3-yl)-phenyl |
| 1104. | 3-fluoropropyl | 4-((R)-1-methylpyrrolidin-3-yl)-phenyl |
| 1105. | 3-fluoropropyl | 4-(2,2-dimethylpyrrolidin-1-yl)-phenyl |
| 1106. | 3-fluoropropyl | 4-(3,3-dimethylpyrrolidin-1-yl)-phenyl |
| 1107. | 3-fluoropropyl | 4-(2-trifluoromethylpyrrolidin-1-yl)-phenyl |
| 1108. | 3-fluoropropyl | 4-((S)-2-trifluoromethylpyrrolidin-1-yl)-phenyl |
| 1109. | 3-fluoropropyl | 4-((R)-2-trifluoromethylpyrrolidin-1-yl)-phenyl |
| 1110. | 3-fluoropropyl | 4-(3-trifluoromethylpyrrolidin-1-yl)-phenyl |
| 1111. | 3-fluoropropyl | 4-((S)-3-trifluoromethylpyrrolidin-1-yl)-phenyl |
| 1112. | 3-fluoropropyl | 4-((R)-3-trifluoromethylpyrrolidin-1-yl)-phenyl |
| 1113. | 3-fluoropropyl | 4-(2-methoxymethylpyrrolidin-1-yl)-phenyl |
| 1114. | 3-fluoropropyl | 4-((S)-2-methoxymethylpyrrolidin-1-yl)-phenyl |
| 1115. | 3-fluoropropyl | 4-((R)-2-methoxymethylpyrrolidin-1-yl)-phenyl |

TABLE A-continued

| No. | R¹ | Ar |
|---|---|---|
| 1116. | 3-fluoropropyl | 4-(2-oxopyrrolidin-1-yl)-phenyl |
| 1117. | 3-fluoropropyl | 4-(2-oxo-oxazolidin-3-yl)-phenyl |
| 1118. | 3-fluoropropyl | 4-(piperidin-1-yl)-phenyl |
| 1119. | 3-fluoropropyl | 4-(2-methylpiperidin-1-yl)-phenyl |
| 1120. | 3-fluoropropyl | 4-((S)-2-methylpiperidin-1-yl)-phenyl |
| 1121. | 3-fluoropropyl | 4-((R)-2-methylpiperidin-1-yl)-phenyl |
| 1122. | 3-fluoropropyl | 4-(piperazin-1-yl)-phenyl |
| 1123. | 3-fluoropropyl | 4-(4-methylpiperazin-1-yl)-phenyl |
| 1124. | 3-fluoropropyl | 4-(morpholin-4-yl)-phenyl |
| 1125. | 3-fluoropropyl | 4-(thiomorpholin-4-yl)-phenyl |
| 1126. | 3-fluoropropyl | 4-(1-oxo-thiomorpholin-4-yl)-phenyl |
| 1127. | 3-fluoropropyl | 4-(1,1-dioxo-thiomorpholin-4-yl)-phenyl |
| 1128. | 3-fluoropropyl | 4-(pyrrol-1-yl)-phenyl |
| 1129. | 3-fluoropropyl | 4-(pyrrol-2-yl)-phenyl |
| 1130. | 3-fluoropropyl | 4-(pyrrol-3-yl)-phenyl |
| 1131. | 3-fluoropropyl | 4-(1-methylpyrrol-2-yl)-phenyl |
| 1132. | 3-fluoropropyl | 4-(1-methylpyrrol-3-yl)-phenyl |
| 1133. | 3-fluoropropyl | 4-(furan-2-yl)-phenyl |
| 1134. | 3-fluoropropyl | 4-(furan-3-yl)-phenyl |
| 1135. | 3-fluoropropyl | 4-(thiophen-2-yl)-phenyl |
| 1136. | 3-fluoropropyl | 4-(thiophen-3-yl)-phenyl |
| 1137. | 3-fluoropropyl | 4-(5-propylthien-2-yl)-phenyl |
| 1138. | 3-fluoropropyl | 4-(pyrazol-1-yl)-phenyl |
| 1139. | 3-fluoropropyl | 4-(pyrazol-3-yl)-phenyl |
| 1140. | 3-fluoropropyl | 4-(pyrazol-4-yl)-phenyl |
| 1141. | 3-fluoropropyl | 4-(1-methyl-1H-pyrazol-4-yl)-phenyl |
| 1142. | 3-fluoropropyl | 4-(1-ethyl-1H-pyrazol-4-yl)-phenyl |
| 1143. | 3-fluoropropyl | 4-(1-methyl-1H-pyrazol-5-yl)-phenyl |
| 1144. | 3-fluoropropyl | 4-(1H-imidazol-2-yl)-phenyl |
| 1145. | 3-fluoropropyl | 4-(imidazol-1-yl)-phenyl |
| 1146. | 3-fluoropropyl | 4-(1-methylimidazol-2-yl)-phenyl |
| 1147. | 3-fluoropropyl | 4-(oxazol-2-yl)-phenyl |
| 1148. | 3-fluoropropyl | 4-(oxazol-4-yl)-phenyl |
| 1149. | 3-fluoropropyl | 4-(oxazol-5-yl)-phenyl |
| 1150. | 3-fluoropropyl | 4-(isoxazol-3-yl)-phenyl |
| 1151. | 3-fluoropropyl | 4-(isoxazol-4-yl)-phenyl |
| 1152. | 3-fluoropropyl | 4-(isoxazol-5-yl)-phenyl |
| 1153. | 3-fluoropropyl | 4-([1,2,3]-triazol-1-yl)-phenyl |
| 1154. | 3-fluoropropyl | 4-([1,2,4]-triazol-1-yl)-phenyl |
| 1155. | 3-fluoropropyl | 4-([1,2,3]-triazol-2-yl)-phenyl |
| 1156. | 3-fluoropropyl | 4-(4H-[1,2,4]-triazol-3-yl)-phenyl |
| 1157. | 3-fluoropropyl | 4-([1,2,4]-triazol-4-yl)-phenyl |
| 1158. | 3-fluoropropyl | 4-(2H-[1,2,3]-triazol-4-yl)-phenyl |
| 1159. | 3-fluoropropyl | 4-(4-methyl-4H-[1,2,4]-triazol-3-yl)-phenyl |
| 1160. | 3-fluoropropyl | 4-(2-methyl-2H-[1,2,3]-triazol-4-yl)-phenyl |
| 1161. | 3-fluoropropyl | 4-([1,3,4]-oxadiazol-2-yl)-phenyl |
| 1162. | 3-fluoropropyl | 4-([1,2,4]-oxadiazol-3-yl)-phenyl |
| 1163. | 3-fluoropropyl | 4-([1,2,4]-oxadiazol-5-yl)-phenyl |
| 1164. | 3-fluoropropyl | 4-([1,2,3]-oxadiazol-4-yl)-phenyl |
| 1165. | 3-fluoropropyl | 4-([1,2,3]-oxadiazol-5-yl)-phenyl |
| 1166. | 3-fluoropropyl | 4-([1,2,3]-thiadiazol-4-yl)-phenyl |
| 1167. | 3-fluoropropyl | 4-(1H-tetrazol-5-yl)-phenyl |
| 1168. | 3-fluoropropyl | 4-(tetrazol-1-yl)-phenyl |
| 1169. | 3-fluoropropyl | 4-(2-methyl-2H-tetrazol-5-yl)-phenyl |
| 1170. | 3-fluoropropyl | 4-(1-methyl-1H-tetrazol-5-yl)-phenyl |
| 1171. | 3-fluoropropyl | 4-furazan-3-yl-phenyl |
| 1172. | 3-fluoropropyl | 4-(pyrid-2-yl)-phenyl |
| 1173. | 3-fluoropropyl | 4-(pyrid-3-yl)-phenyl |
| 1174. | 3-fluoropropyl | 4-(pyrid-4-yl)-phenyl |
| 1175. | 3-fluoropropyl | 4-(pyrimidin-2-yl)-phenyl |
| 1176. | 3-fluoropropyl | 4-(pyrimidin-4-yl)-phenyl |
| 1177. | 3-fluoropropyl | 4-(pyrimidin-5-yl)-phenyl |
| 1178. | 3-fluoropropyl | 5-isopropylthiophen-2-yl |
| 1179. | 3-fluoropropyl | 2-chlorothiophen-5-yl |
| 1180. | 3-fluoropropyl | 2,5-dichlorothiophen-4-yl |
| 1181. | 3-fluoropropyl | 2,3-dichlorothiophen-5-yl |
| 1182. | 3-fluoropropyl | 2-chloro-3-nitrothiophen-5-yl |
| 1183. | 3-fluoropropyl | 2-(phenylsulfonyl)-thiophen-5-yl |
| 1184. | 3-fluoropropyl | 2-(pyridin-2-yl)thiophen-5-yl |
| 1185. | 3-fluoropropyl | 2-(5-(trifluoromethyl)isoxazol-3-yl)-thiophen-5-yl |
| 1186. | 3-fluoropropyl | 2-(2-methylthiazol-4-yl)-thiophen-5-yl |
| 1187. | 3-fluoropropyl | 1-methyl-1H-imidazol-4-yl |
| 1188. | 3-fluoropropyl | 1,2-dimethyl-1H-imidazol-4-yl |
| 1189. | 3-fluoropropyl | 3,5-dimethylisoxazol-4-yl |
| 1190. | 3-fluoropropyl | thiazol-2-yl |
| 1191. | 3-fluoropropyl | 4-methylthiazol-2-yl |
| 1192. | 3-fluoropropyl | 4-isopropylthiazol-2-yl |

TABLE A-continued

| No. | R¹ | Ar |
|---|---|---|
| 1193. | 3-fluoropropyl | 4-trifluoromethylthiazol-2-yl |
| 1194. | 3-fluoropropyl | 5-methylthiazol-2-yl |
| 1195. | 3-fluoropropyl | 5-isopropylthiazol-2-yl |
| 1196. | 3-fluoropropyl | 5-trifluoromethylthiazol-2-yl |
| 1197. | 3-fluoropropyl | 2,4-dimethylthiazol-5-yl |
| 1198. | 3-fluoropropyl | 2-acetamido-4-methylthiazol-5-yl |
| 1199. | 3-fluoropropyl | 4H-[1,2,4]triazol-3-yl |
| 1200. | 3-fluoropropyl | 5-methyl-4H-[1,2,4]triazol-3-yl |
| 1201. | 3-fluoropropyl | 4-methyl-4H-[1,2,4]triazol-3-yl |
| 1238. | 2-fluoroethyl | 4-(fluoromethyl)phenyl |
| 1239. | 2-fluoroethyl | 3-(fluoromethyl)phenyl |
| 1240. | 2-fluoroethyl | 2-(fluoromethyl)phenyl |
| 1241. | 2-fluoroethyl | 4-(difluoromethyl)phenyl |
| 1242. | 2-fluoroethyl | 3-(difluoromethyl)phenyl |
| 1243. | 2-fluoroethyl | 2-(difluoromethyl)phenyl |
| 1244. | 2-fluoroethyl | 4-(trifluoromethyl)phenyl |
| 1245. | 2-fluoroethyl | 3-(trifluoromethyl)phenyl |
| 1246. | 2-fluoroethyl | 2-(trifluoromethyl)phenyl |
| 1247. | 2-fluoroethyl | 4-(1-fluoroethyl)-phenyl |
| 1248. | 2-fluoroethyl | 4-((S)-1-fluoroethyl)-phenyl |
| 1249. | 2-fluoroethyl | 4-((R)-1-fluoroethyl)-phenyl |
| 1250. | 2-fluoroethyl | 4-(2-fluoroethyl)-phenyl |
| 1251. | 2-fluoroethyl | 4-(1,1-difluoroethyl)-phenyl |
| 1252. | 2-fluoroethyl | 4-(2,2-difluoroethyl)-phenyl |
| 1253. | 2-fluoroethyl | 4-(2,2,2-trifluoroethyl)-phenyl |
| 1254. | 2-fluoroethyl | 4-(3-fluoropropyl)-phenyl |
| 1255. | 2-fluoroethyl | 4-(2-fluoropropyl)-phenyl |
| 1256. | 2-fluoroethyl | 4-((S)-2-fluoropropyl)-phenyl |
| 1257. | 2-fluoroethyl | 4-((R)-2-fluoropropyl)-phenyl |
| 1258. | 2-fluoroethyl | 4-(3,3-difluoropropyl)-phenyl |
| 1259. | 2-fluoroethyl | 4-(3,3,3-trifluoropropyl)-phenyl |
| 1260. | 2-fluoroethyl | 4-(1-fluoro-1-methylethyl)-phenyl |
| 1261. | 2-fluoroethyl | 4-(2-fluoro-1-methylethyl)-phenyl |
| 1262. | 2-fluoroethyl | 4-((S)-2-fluoro-1-methylethyl)-phenyl |
| 1263. | 2-fluoroethyl | 4-((R)-2-fluoro-1-methylethyl)-phenyl |
| 1264. | 2-fluoroethyl | 4-(2,2-difluoro-1-methylethyl)-phenyl |
| 1265. | 2-fluoroethyl | 4-((S)-2,2-difluoro-1-methylethyl)-phenyl |
| 1266. | 2-fluoroethyl | 4-((R)-2,2-difluoro-1-methylethyl)-phenyl |
| 1267. | 2-fluoroethyl | 4-(2,2,2-trifluoro-1-methylethyl)-phenyl |
| 1268. | 2-fluoroethyl | 4-((S)-2,2,2-trifluoro-1-methylethyl)-phenyl |
| 1269. | 2-fluoroethyl | 4-((R)-2,2,2-trifluoro-1-methylethyl)-phenyl |
| 1270. | 2-fluoroethyl | 4-(2-fluoro-1-fluoromethylethyl)-phenyl |
| 1271. | 2-fluoroethyl | 4-(1-difluoromethyl-2,2-difluoroethyl)-phenyl |
| 1272. | 2-fluoroethyl | 4-(1,1-dimethyl-2-fluoroethyl)-phenyl |
| 1273. | 2-fluoroethyl | 4-methoxyphenyl |
| 1274. | 2-fluoroethyl | 4-ethoxyphenyl |
| 1275. | 2-fluoroethyl | 4-propoxyphenyl |
| 1276. | 2-fluoroethyl | 4-isopropoxyphenyl |
| 1277. | 2-fluoroethyl | 4-butoxyphenyl |
| 1278. | 2-fluoroethyl | 4-(fluoromethoxy)-phenyl |
| 1279. | 2-fluoroethyl | 4-(difluoromethoxy)-phenyl |
| 1280. | 2-fluoroethyl | 4-(trifluoromethoxy)-phenyl |
| 1281. | 2-fluoroethyl | 3-(trifluoromethoxy)-phenyl |
| 1282. | 2-fluoroethyl | 4-(2-fluoroethoxy)-phenyl |
| 1283. | 2-fluoroethyl | 4-(2,2-difluoroethoxy)-phenyl |
| 1284. | 2-fluoroethyl | 4-(2,2,2-trifluoroethoxy)-phenyl |
| 1285. | 2-fluoroethyl | 4-(1,1,2,2-tetrafluoroethoxy)-phenyl |
| 1286. | 2-fluoroethyl | 4-cyclopropylphenyl |
| 1287. | 2-fluoroethyl | 4-cyclobutylphenyl |
| 1288. | 2-fluoroethyl | 4-cyclopentylphenyl |
| 1289. | 2-fluoroethyl | 4-(2,2-difluorocyclopropyl)-phenyl |
| 1290. | 2-fluoroethyl | 3,4-difluorophenyl |
| 1291. | 2-fluoroethyl | 4-bromo-3-fluorophenyl |
| 1292. | 2-fluoroethyl | 4-bromo-2-fluorophenyl |
| 1293. | 2-fluoroethyl | 4-bromo-2,5-difluorophenyl |
| 1294. | 2-fluoroethyl | 2-fluoro-4-isopropylphenyl |
| 1295. | 2-fluoroethyl | 3-fluoro-4-isopropylphenyl |
| 1296. | 2-fluoroethyl | 4-(1-hydroxy-1-methylethyl)-phenyl |
| 1297. | 2-fluoroethyl | 4-(2-hydroxy-2-methylpropyl)-phenyl |
| 1298. | 2-fluoroethyl | 4-acetylphenyl |
| 1299. | 2-fluoroethyl | 4-carboxyphenyl |
| 1300. | 2-fluoroethyl | 4-cyanophenyl |
| 1301. | 2-fluoroethyl | 4-hydroxyphenyl |
| 1302. | 2-fluoroethyl | 4-(O-benzyl)-phenyl |
| 1303. | 2-fluoroethyl | 4-(2-methoxyethoxy)-phenyl |
| 1304. | 2-fluoroethyl | 4-($CH_2$—$N(CH_3)_2$)-phenyl |
| 1305. | 2-fluoroethyl | 4-(NH—CO—$NH_2$)-phenyl |

TABLE A-continued

| No. | R¹ | Ar |
|---|---|---|
| 1306. | 2-fluoroethyl | 4-(methylsulfanyl)-phenyl |
| 1307. | 2-fluoroethyl | 4-(fluoromethylsulfanyl)-phenyl |
| 1308. | 2-fluoroethyl | 4-(difluoromethylsulfanyl)-phenyl |
| 1309. | 2-fluoroethyl | 4-(trifluoromethylsulfanyl)-phenyl |
| 1310. | 2-fluoroethyl | 4-(methylsulfonyl)-phenyl |
| 1311. | 2-fluoroethyl | 4-(N-methoxy-N-methyl-amino)-phenyl |
| 1312. | 2-fluoroethyl | 4-(methoxyamino)-phenyl |
| 1313. | 2-fluoroethyl | 4-(ethoxyamino)-phenyl |
| 1314. | 2-fluoroethyl | 4-(N-methylaminooxy)-phenyl |
| 1315. | 2-fluoroethyl | 4-(N,N-dimethylaminooxy)-phenyl |
| 1316. | 2-fluoroethyl | 4-(azetidin-1-yl)-phenyl |
| 1317. | 2-fluoroethyl | 4-(2-methylazetidin-1-yl)-phenyl |
| 1318. | 2-fluoroethyl | 4-((S)-2-methylazetidin-1-yl)-phenyl |
| 1319. | 2-fluoroethyl | 4-((R)-2-methylazetidin-1-yl)-phenyl |
| 1320. | 2-fluoroethyl | 4-(3-fluoroazetidin-1-yl)-phenyl |
| 1321. | 2-fluoroethyl | 4-(3-methoxyazetidin-1-yl)-phenyl |
| 1322. | 2-fluoroethyl | 4-(3-hydroxyazetidin-1-yl)-phenyl |
| 1323. | 2-fluoroethyl | 4-(pyrrolidin-1-yl)-phenyl |
| 1324. | 2-fluoroethyl | 4-(pyrrolidin-2-yl)-phenyl |
| 1325. | 2-fluoroethyl | 4-((S)-pyrrolidin-2-yl)-phenyl |
| 1326. | 2-fluoroethyl | 4-((R)-pyrrolidin-2-yl)-phenyl |
| 1327. | 2-fluoroethyl | 4-(pyrrolidin-3-yl)-phenyl |
| 1328. | 2-fluoroethyl | 4-((S)-pyrrolidin-3-yl)-phenyl |
| 1329. | 2-fluoroethyl | 4-((R)-pyrrolidin-3-yl)-phenyl |
| 1330. | 2-fluoroethyl | 4-(2-fluoropyrrolidin-1-yl)-phenyl |
| 1331. | 2-fluoroethyl | 4-((S)-2-fluoropyrrolidin-1-yl)-phenyl |
| 1332. | 2-fluoroethyl | 4-((R)-2-fluoropyrrolidin-1-yl)-phenyl |
| 1333. | 2-fluoroethyl | 4-(3-fluoropyrrolidin-1-yl)-phenyl |
| 1334. | 2-fluoroethyl | 4-((S)-3-fluoropyrrolidin-1-yl)-phenyl |
| 1335. | 2-fluoroethyl | 4-((R)-3-fluoropyrrolidin-1-yl)-phenyl |
| 1336. | 2-fluoroethyl | 4-(2,2-difluoropyrrolidin-1-yl)-phenyl |
| 1337. | 2-fluoroethyl | 4-(3,3-difluoropyrrolidin-1-yl)-phenyl |
| 1338. | 2-fluoroethyl | 4-(2-methylpyrrolidin-1-yl)-phenyl |
| 1339. | 2-fluoroethyl | 4-((S)-2-methylpyrrolidin-1-yl)-phenyl |
| 1340. | 2-fluoroethyl | 4-((R)-2-methylpyrrolidin-1-yl)-phenyl |
| 1341. | 2-fluoroethyl | 4-(3-methylpyrrolidin-1-yl)-phenyl |
| 1342. | 2-fluoroethyl | 4-((S)-3-methylpyrrolidin-1-yl)-phenyl |
| 1343. | 2-fluoroethyl | 4-((R)-3-methylpyrrolidin-1-yl)-phenyl |
| 1344. | 2-fluoroethyl | 4-(1-methylpyrrolidin-2-yl)-phenyl |
| 1345. | 2-fluoroethyl | 4-((S)-1-methylpyrrolidin-2-yl)-phenyl |
| 1346. | 2-fluoroethyl | 4-((R)-1-methylpyrrolidin-2-yl)-phenyl |
| 1347. | 2-fluoroethyl | 4-(1-methylpyrrolidin-3-yl)-phenyl |
| 1348. | 2-fluoroethyl | 4-((S)-1-methylpyrrolidin-3-yl)-phenyl |
| 1349. | 2-fluoroethyl | 4-((R)-1-methylpyrrolidin-3-yl)-phenyl |
| 1350. | 2-fluoroethyl | 4-(2,2-dimethylpyrrolidin-1-yl)-phenyl |
| 1351. | 2-fluoroethyl | 4-(3,3-dimethylpyrrolidin-1-yl)-phenyl |
| 1352. | 2-fluoroethyl | 4-(2-trifluoromethylpyrrolidin-1-yl)-phenyl |
| 1353. | 2-fluoroethyl | 4-((S)-2-trifluoromethylpyrrolidin-1-yl)-phenyl |
| 1354. | 2-fluoroethyl | 4-((R)-2-trifluoromethylpyrrolidin-1-yl)-phenyl |
| 1355. | 2-fluoroethyl | 4-(3-trifluoromethylpyrrolidin-1-yl)-phenyl |
| 1356. | 2-fluoroethyl | 4-((S)-3-trifluoromethylpyrrolidin-1-yl)-phenyl |
| 1357. | 2-fluoroethyl | 4-((R)-3-trifluoromethylpyrrolidin-1-yl)-phenyl |
| 1358. | 2-fluoroethyl | 4-(2-methoxymethylpyrrolidin-1-yl)-phenyl |
| 1359. | 2-fluoroethyl | 4-((S)-2-methoxymethylpyrrolidin-1-yl)-phenyl |
| 1360. | 2-fluoroethyl | 4-((R)-2-methoxymethylpyrrolidin-1-yl)-phenyl |
| 1361. | 2-fluoroethyl | 4-(2-oxopyrrolidin-1-yl)-phenyl |
| 1362. | 2-fluoroethyl | 4-(2-oxo-oxazolidin-3-yl)-phenyl |
| 1363. | 2-fluoroethyl | 4-(piperidin-1-yl)-phenyl |
| 1364. | 2-fluoroethyl | 4-(2-methylpiperidin-1-yl)-phenyl |
| 1365. | 2-fluoroethyl | 4-((S)-2-methylpiperidin-1-yl)-phenyl |
| 1366. | 2-fluoroethyl | 4-((R)-2-methylpiperidin-1-yl)-phenyl |
| 1367. | 2-fluoroethyl | 4-(piperazin-1-yl)-phenyl |
| 1368. | 2-fluoroethyl | 4-(4-methylpiperazin-1-yl)-phenyl |
| 1369. | 2-fluoroethyl | 4-(morpholin-4-yl)-phenyl |
| 1370. | 2-fluoroethyl | 4-(thiomorpholin-4-yl)-phenyl |
| 1371. | 2-fluoroethyl | 4-(1-oxo-thiomorpholin-4-yl)-phenyl |
| 1372. | 2-fluoroethyl | 4-(1,1-dioxo-thiomorpholin-4-yl)-phenyl |
| 1373. | 2-fluoroethyl | 4-(pyrrol-1-yl)-phenyl |
| 1374. | 2-fluoroethyl | 4-(pyrrol-2-yl)-phenyl |
| 1375. | 2-fluoroethyl | 4-(pyrrol-3-yl)-phenyl |
| 1376. | 2-fluoroethyl | 4-(1-methylpyrrol-2-yl)-phenyl |
| 1377. | 2-fluoroethyl | 4-(1-methylpyrrol-3-yl)-phenyl |
| 1378. | 2-fluoroethyl | 4-(furan-2-yl)-phenyl |
| 1379. | 2-fluoroethyl | 4-(furan-3-yl)-phenyl |
| 1380. | 2-fluoroethyl | 4-(thiophen-2-yl)-phenyl |
| 1381. | 2-fluoroethyl | 4-(thiophen-3-yl)-phenyl |
| 1382. | 2-fluoroethyl | 4-(5-propylthien-2-yl)-phenyl |

TABLE A-continued

| No. | R¹ | Ar |
|---|---|---|
| 1383. | 2-fluoroethyl | 4-(pyrazol-1-yl)-phenyl |
| 1384. | 2-fluoroethyl | 4-(pyrazol-3-yl)-phenyl |
| 1385. | 2-fluoroethyl | 4-(pyrazol-4-yl)-phenyl |
| 1386. | 2-fluoroethyl | 4-(1-methyl-1H-pyrazol-4-yl)-phenyl |
| 1387. | 2-fluoroethyl | 4-(1-ethyl-1H-pyrazol-4-yl)-phenyl |
| 1388. | 2-fluoroethyl | 4-(1-methyl-1H-pyrazol-5-yl)-phenyl |
| 1389. | 2-fluoroethyl | 4-(1H-imidazol-2-yl)-phenyl |
| 1390. | 2-fluoroethyl | 4-(imidazol-1-yl)-phenyl |
| 1391. | 2-fluoroethyl | 4-(1-methylimidazol-2-yl)-phenyl |
| 1392. | 2-fluoroethyl | 4-(oxazol-2-yl)-phenyl |
| 1393. | 2-fluoroethyl | 4-(oxazol-4-yl)-phenyl |
| 1394. | 2-fluoroethyl | 4-(oxazol-5-yl)-phenyl |
| 1395. | 2-fluoroethyl | 4-(isoxazol-3-yl)-phenyl |
| 1396. | 2-fluoroethyl | 4-(isoxazol-4-yl)-phenyl |
| 1397. | 2-fluoroethyl | 4-(isoxazol-5-yl)-phenyl |
| 1398. | 2-fluoroethyl | 4-([1,2,3]-triazol-1-yl)-phenyl |
| 1399. | 2-fluoroethyl | 4-([1,2,4]-triazol-1-yl)-phenyl |
| 1400. | 2-fluoroethyl | 4-([1,2,3]-triazol-2-yl)-phenyl |
| 1401. | 2-fluoroethyl | 4-(4H-[1,2,4]-triazol-3-yl)-phenyl |
| 1402. | 2-fluoroethyl | 4-([1,2,4]-triazol-4-yl)-phenyl |
| 1403. | 2-fluoroethyl | 4-(2H-[1,2,3]-triazol-4-yl)-phenyl |
| 1404. | 2-fluoroethyl | 4-(4-methyl-4H-[1,2,4]-triazol-3-yl)-phenyl |
| 1405. | 2-fluoroethyl | 4-(2-methyl-2H-[1,2,3]-triazol-4-yl)-phenyl |
| 1406. | 2-fluoroethyl | 4-([1,3,4]-oxadiazol-2-yl)-phenyl |
| 1407. | 2-fluoroethyl | 4-([1,2,4]-oxadiazol-3-yl)-phenyl |
| 1408. | 2-fluoroethyl | 4-([1,2,4]-oxadiazol-5-yl)-phenyl |
| 1409. | 2-fluoroethyl | 4-([1,2,3]-oxadiazol-4-yl)-phenyl |
| 1410. | 2-fluoroethyl | 4-([1,2,3]-oxadiazol-5-yl)-phenyl |
| 1411. | 2-fluoroethyl | 4-([1,2,3]-thiadiazol-4-yl)-phenyl |
| 1412. | 2-fluoroethyl | 4-(1H-tetrazol-5-yl)-phenyl |
| 1413. | 2-fluoroethyl | 4-(tetrazol-1-yl)-phenyl |
| 1414. | 2-fluoroethyl | 4-(2-methyl-2H-tetrazol-5-yl)-phenyl |
| 1415. | 2-fluoroethyl | 4-(1-methyl-1H-tetrazol-5-yl)-phenyl |
| 1416. | 2-fluoroethyl | 4-furazan-3-yl-phenyl |
| 1417. | 2-fluoroethyl | 4-(pyrid-2-yl)-phenyl |
| 1418. | 2-fluoroethyl | 4-(pyrid-3-yl)-phenyl |
| 1419. | 2-fluoroethyl | 4-(pyrid-4-yl)-phenyl |
| 1420. | 2-fluoroethyl | 4-(pyrimidin-2-yl)-phenyl |
| 1421. | 2-fluoroethyl | 4-(pyrimidin-4-yl)-phenyl |
| 1422. | 2-fluoroethyl | 4-(pyrimidin-5-yl)-phenyl |
| 1423. | 2-fluoroethyl | 5-isopropylthiophen-2-yl |
| 1424. | 2-fluoroethyl | 2-chlorothiophen-5-yl |
| 1425. | 2-fluoroethyl | 2,5-dichlorothiophen-4-yl |
| 1426. | 2-fluoroethyl | 2,3-dichlorothiophen-5-yl |
| 1427. | 2-fluoroethyl | 2-chloro-3-nitrothiophen-5-yl |
| 1428. | 2-fluoroethyl | 2-(phenylsulfonyl)-thiophen-5-yl |
| 1429. | 2-fluoroethyl | 2-(pyridin-2-yl)thiophen-5-yl |
| 1430. | 2-fluoroethyl | 2-(5-(trifluoromethyl)isoxazol-3-yl)-thiophen-5-yl |
| 1431. | 2-fluoroethyl | 2-(2-methylthiazol-4-yl)-thiophen-5-yl |
| 1432. | 2-fluoroethyl | 1-methyl-1H-imidazol-4-yl |
| 1433. | 2-fluoroethyl | 1,2-dimethyl-1H-imidazol-4-yl |
| 1434. | 2-fluoroethyl | 3,5-dimethylisoxazol-4-yl |
| 1435. | 2-fluoroethyl | thiazol-2-yl |
| 1436. | 2-fluoroethyl | 4-methylthiazol-2-yl |
| 1437. | 2-fluoroethyl | 4-isopropylthiazol-2-yl |
| 1438. | 2-fluoroethyl | 4-trifluoromethylthiazol-2-yl |
| 1439. | 2-fluoroethyl | 5-methylthiazol-2-yl |
| 1440. | 2-fluoroethyl | 5-isopropylthiazol-2-yl |
| 1441. | 2-fluoroethyl | 5-trifluoromethylthiazol-2-yl |
| 1442. | 2-fluoroethyl | 2,4-dimethylthiazol-5-yl |
| 1443. | 2-fluoroethyl | 2-acetamido-4-methylthiazol-5-yl |
| 1444. | 2-fluoroethyl | 4H-[1,2,4]triazol-3-yl |
| 1445. | 2-fluoroethyl | 5-methyl-4H-[1,2,4]triazol-3-yl |
| 1446. | 2-fluoroethyl | 4-methyl-4H-[1,2,4]triazol-3-yl |
| 1447. | 2-fluoroethyl | 5-isopropyl-4H-[1,2,4]triazol-3-yl |
| 1448. | 2-fluoroethyl | 5-trifluoromethyl-4H-[1,2,4]triazol-3-yl |
| 1449. | 2-fluoroethyl | 4,5-dimethyl-4H-[1,2,4]triazol-3-yl |
| 1450. | 2-fluoroethyl | 5-isopropyl-4-methyl-4H-[1,2,4]triazol-3-yl |
| 1451. | 2-fluoroethyl | 5-trifluoromethyl-4-methyl-4H-[1,2,4]triazol-3-yl |
| 1452. | 2-fluoroethyl | [1,3,4]thiadiazol-2-yl |
| 1453. | 2-fluoroethyl | 5-methyl-[1,3,4]thiadiazol-2-yl |
| 1454. | 2-fluoroethyl | 5-isopropyl-[1,3,4]thiadiazol-2-yl |
| 1455. | 2-fluoroethyl | 5-trifluoromethyl-[1,3,4]thiadiazol-2-yl |
| 1456. | 2-fluoroethyl | 3-bromo-2-chloropyrid-5-yl |
| 1457. | 2-fluoroethyl | 2-(4-morpholino)-pyrid-5-yl |
| 1458. | 2-fluoroethyl | 2-phenoxypyrid-5-yl |
| 1459. | 2-fluoroethyl | (2-isopropyl)-pyrimidin-5-yl |

TABLE A-continued

| No. | R¹ | Ar |
|---|---|---|
| 1460. | 2-fluoroethyl | (5-isopropyl)-pyrimidin-2-yl |
| 1461. | 2-fluoroethyl | 8-quinolyl |
| 1462. | 2-fluoroethyl | 5-isoquinolyl |
| 1463. | 2-fluoroethyl | 2-(trifluoroacetyl)-1,2,3,4-tetrahydroisoquinolin-7-yl |
| 1464. | 2-fluoroethyl | 5-chloro-3-methylbenzothiophen-2-yl |
| 1465. | 2-fluoroethyl | 3,4-dihydro-4-methyl-2H-benzo[b][1,4]oxazinyl |
| 1466. | 2-fluoroethyl | benzothiazol-6-yl |
| 1467. | 2-fluoroethyl | benzo[2,1,3]oxadiazol-4-yl |
| 1468. | 2-fluoroethyl | 5-chlorobenzo[2,1,3]oxadiazol-4-yl |
| 1469. | 2-fluoroethyl | 7-chlorobenzo[2,1,3]oxadiazol-4-yl |
| 1470. | 2-fluoroethyl | benzo[2,1,3]thiadiazol-4-yl |
| 1471. | cyclopropylmethyl | 4-methylphenyl |
| 1472. | cyclopropylmethyl | 4-ethylphenyl |
| 1473. | cyclopropylmethyl | 4-propylphenyl |
| 1474. | cyclopropylmethyl | 4-isopropylphenyl |
| 1475. | cyclopropylmethyl | 4-sec-butylphenyl |
| 1476. | cyclopropylmethyl | 4-isobutylphenyl |
| 1477. | cyclopropylmethyl | 4-(1,1-dimethylpropyl)-phenyl |
| 1478. | cyclopropylmethyl | 4-vinylphenyl |
| 1479. | cyclopropylmethyl | 4-isopropenylphenyl |
| 1480. | cyclopropylmethyl | 4-fluorophenyl |
| 1481. | cyclopropylmethyl | 4-chlorophenyl |
| 1482. | cyclopropylmethyl | 4-bromophenyl |
| 1483. | cyclopropylmethyl | 4-(fluoromethyl)phenyl |
| 1484. | cyclopropylmethyl | 3-(fluoromethyl)phenyl |
| 1485. | cyclopropylmethyl | 2-(fluoromethyl)phenyl |
| 1486. | cyclopropylmethyl | 4-(difluoromethyl)phenyl |
| 1487. | cyclopropylmethyl | 3-(difluoromethyl)phenyl |
| 1488. | cyclopropylmethyl | 2-(difluoromethyl)phenyl |
| 1489. | cyclopropylmethyl | 4-(trifluoromethyl)phenyl |
| 1490. | cyclopropylmethyl | 3-(trifluoromethyl)phenyl |
| 1491. | cyclopropylmethyl | 2-(trifluoromethyl)phenyl |
| 1492. | cyclopropylmethyl | 4-(1-fluoroethyl)-phenyl |
| 1493. | cyclopropylmethyl | 4-((S)-1-fluoroethyl)-phenyl |
| 1494. | cyclopropylmethyl | 4-((R)-1-fluoroethyl)-phenyl |
| 1495. | cyclopropylmethyl | 4-(2-fluoroethyl)-phenyl |
| 1496. | cyclopropylmethyl | 4-(1,1-difluoroethyl)-phenyl |
| 1497. | cyclopropylmethyl | 4-(2,2-difluoroethyl)-phenyl |
| 1498. | cyclopropylmethyl | 4-(2,2,2-trifluoroethyl)-phenyl |
| 1499. | cyclopropylmethyl | 4-(3-fluoropropyl)-phenyl |
| 1500. | cyclopropylmethyl | 4-(2-fluoropropyl)-phenyl |
| 1501. | cyclopropylmethyl | 4-((S)-2-fluoropropyl)-phenyl |
| 1502. | cyclopropylmethyl | 4-((R)-2-fluoropropyl)-phenyl |
| 1503. | cyclopropylmethyl | 4-(3,3-difluoropropyl)-phenyl |
| 1504. | cyclopropylmethyl | 4-(3,3,3-trifluoropropyl)-phenyl |
| 1505. | cyclopropylmethyl | 4-(1-fluoro-1-methylethyl)-phenyl |
| 1506. | cyclopropylmethyl | 4-(2-fluoro-1-methylethyl)-phenyl |
| 1507. | cyclopropylmethyl | 4-((S)-2-fluoro-1-methylethyl)-phenyl |
| 1508. | cyclopropylmethyl | 4-((R)-2-fluoro-1-methylethyl)-phenyl |
| 1509. | cyclopropylmethyl | 4-(2,2-difluoro-1-methylethyl)-phenyl |
| 1510. | cyclopropylmethyl | 4-((S)-2,2-difluoro-1-methylethyl)-phenyl |
| 1511. | cyclopropylmethyl | 4-((R)-2,2-difluoro-1-methylethyl)-phenyl |
| 1512. | cyclopropylmethyl | 4-(2,2,2-trifluoro-1-methylethyl)-phenyl |
| 1513. | cyclopropylmethyl | 4-((S)-2,2,2-trifluoro-1-methylethyl)-phenyl |
| 1514. | cyclopropylmethyl | 4-((R)-2,2,2-trifluoro-1-methylethyl)-phenyl |
| 1515. | cyclopropylmethyl | 4-(2-fluoro-1-fluoromethylethyl)-phenyl |
| 1516. | cyclopropylmethyl | 4-(1-difluoromethyl-2,2-difluoroethyl)-phenyl |
| 1517. | cyclopropylmethyl | 4-(1,1-dimethyl-2-fluoroethyl)-phenyl |
| 1518. | cyclopropylmethyl | 4-methoxyphenyl |
| 1519. | cyclopropylmethyl | 4-ethoxyphenyl |
| 1520. | cyclopropylmethyl | 4-propoxyphenyl |
| 1521. | cyclopropylmethyl | 4-isopropoxyphenyl |
| 1522. | cyclopropylmethyl | 4-butoxyphenyl |
| 1523. | cyclopropylmethyl | 4-(fluoromethoxy)-phenyl |
| 1524. | cyclopropylmethyl | 4-(difluoromethoxy)-phenyl |
| 1525. | cyclopropylmethyl | 4-(trifluoromethoxy)-phenyl |
| 1526. | cyclopropylmethyl | 3-(trifluoromethoxy)-phenyl |
| 1527. | cyclopropylmethyl | 4-(2-fluoroethoxy)-phenyl |
| 1528. | cyclopropylmethyl | 4-(2,2-difluoroethoxy)-phenyl |
| 1529. | cyclopropylmethyl | 4-(2,2,2-trifluoroethoxy)-phenyl |
| 1530. | cyclopropylmethyl | 4-(1,1,2,2-tetrafluoroethoxy)-phenyl |
| 1531. | cyclopropylmethyl | 4-cyclopropylphenyl |
| 1532. | cyclopropylmethyl | 4-cyclobutylphenyl |
| 1533. | cyclopropylmethyl | 4-cyclopentylphenyl |
| 1534. | cyclopropylmethyl | 4-(2,2-difluorocyclopropyl)-phenyl |
| 1535. | cyclopropylmethyl | 3,4-difluorophenyl |
| 1536. | cyclopropylmethyl | 4-bromo-3-fluorophenyl |

TABLE A-continued

| No. | R¹ | Ar |
|---|---|---|
| 1537. | cyclopropylmethyl | 4-bromo-2-fluorophenyl |
| 1538. | cyclopropylmethyl | 4-bromo-2,5-difluorophenyl |
| 1539. | cyclopropylmethyl | 2-fluoro-4-isopropylphenyl |
| 1540. | cyclopropylmethyl | 3-fluoro-4-isopropylphenyl |
| 1541. | cyclopropylmethyl | 4-(1-hydroxy-1-methylethyl)-phenyl |
| 1542. | cyclopropylmethyl | 4-(2-hydroxy-2-methylpropyl)-phenyl |
| 1543. | cyclopropylmethyl | 4-acetylphenyl |
| 1544. | cyclopropylmethyl | 4-carboxyphenyl |
| 1545. | cyclopropylmethyl | 4-cyanophenyl |
| 1546. | cyclopropylmethyl | 4-hydroxyphenyl |
| 1547. | cyclopropylmethyl | 4-(O-benzyl)-phenyl |
| 1548. | cyclopropylmethyl | 4-(2-methoxyethoxy)-phenyl |
| 1549. | cyclopropylmethyl | 4-(CH₂—N(CH₃)₂)-phenyl |
| 1550. | cyclopropylmethyl | 4-(NH—CO—NH₂)-phenyl |
| 1551. | cyclopropylmethyl | 4-(methylsulfanyl)-phenyl |
| 1552. | cyclopropylmethyl | 4-(fluoromethylsulfanyl)-phenyl |
| 1553. | cyclopropylmethyl | 4-(difluoromethylsulfanyl)-phenyl |
| 1554. | cyclopropylmethyl | 4-(trifluoromethylsulfanyl)-phenyl |
| 1555. | cyclopropylmethyl | 4-(methylsulfonyl)-phenyl |
| 1556. | cyclopropylmethyl | 4-(N-methoxy-N-methyl-amino)-phenyl |
| 1557. | cyclopropylmethyl | 4-(methoxyamino)-phenyl |
| 1558. | cyclopropylmethyl | 4-(ethoxyamino)-phenyl |
| 1559. | cyclopropylmethyl | 4-(N-methylaminooxy)-phenyl |
| 1560. | cyclopropylmethyl | 4-(N,N-dimethylaminooxy)-phenyl |
| 1561. | cyclopropylmethyl | 4-(azetidin-1-yl)-phenyl |
| 1562. | cyclopropylmethyl | 4-(2-methylazetidin-1-yl)-phenyl |
| 1563. | cyclopropylmethyl | 4-((S)-2-methylazetidin-1-yl)-phenyl |
| 1564. | cyclopropylmethyl | 4-((R)-2-methylazetidin-1-yl)-phenyl |
| 1565. | cyclopropylmethyl | 4-(3-fluoroazetidin-1-yl)-phenyl |
| 1566. | cyclopropylmethyl | 4-(3-methoxyazetidin-1-yl)-phenyl |
| 1567. | cyclopropylmethyl | 4-(3-hydroxyazetidin-1-yl)-phenyl |
| 1568. | cyclopropylmethyl | 4-(pyrrolidin-1-yl)-phenyl |
| 1569. | cyclopropylmethyl | 4-(pyrrolidin-2-yl)-phenyl |
| 1570. | cyclopropylmethyl | 4-((S)-pyrrolidin-2-yl)-phenyl |
| 1571. | cyclopropylmethyl | 4-((R)-pyrrolidin-2-yl)-phenyl |
| 1572. | cyclopropylmethyl | 4-(pyrrolidin-3-yl)-phenyl |
| 1573. | cyclopropylmethyl | 4-((S)-pyrrolidin-3-yl)-phenyl |
| 1574. | cyclopropylmethyl | 4-((R)-pyrrolidin-3-yl)-phenyl |
| 1575. | cyclopropylmethyl | 4-(2-fluoropyrrolidin-1-yl)-phenyl |
| 1576. | cyclopropylmethyl | 4-((S)-2-fluoropyrrolidin-1-yl)-phenyl |
| 1577. | cyclopropylmethyl | 4-((R)-2-fluoropyrrolidin-1-yl)-phenyl |
| 1578. | cyclopropylmethyl | 4-(3-fluoropyrrolidin-1-yl)-phenyl |
| 1579. | cyclopropylmethyl | 4-((S)-3-fluoropyrrolidin-1-yl)-phenyl |
| 1580. | cyclopropylmethyl | 4-((R)-3-fluoropyrrolidin-1-yl)-phenyl |
| 1581. | cyclopropylmethyl | 4-(2,2-difluoropyrrolidin-1-yl)-phenyl |
| 1582. | cyclopropylmethyl | 4-(3,3-difluoropyrrolidin-1-yl)-phenyl |
| 1583. | cyclopropylmethyl | 4-(2-methylpyrrolidin-1-yl)-phenyl |
| 1584. | cyclopropylmethyl | 4-((S)-2-methylpyrrolidin-1-yl)-phenyl |
| 1585. | cyclopropylmethyl | 4-((R)-2-methylpyrrolidin-1-yl)-phenyl |
| 1586. | cyclopropylmethyl | 4-(3-methylpyrrolidin-1-yl)-phenyl |
| 1587. | cyclopropylmethyl | 4-((S)-3-methylpyrrolidin-1-yl)-phenyl |
| 1588. | cyclopropylmethyl | 4-((R)-3-methylpyrrolidin-1-yl)-phenyl |
| 1589. | cyclopropylmethyl | 4-(1-methylpyrrolidin-2-yl)-phenyl |
| 1590. | cyclopropylmethyl | 4-((S)-1-methylpyrrolidin-2-yl)-phenyl |
| 1591. | cyclopropylmethyl | 4-((R)-1-methylpyrrolidin-2-yl)-phenyl |
| 1592. | cyclopropylmethyl | 4-(1-methylpyrrolidin-3-yl)-phenyl |
| 1593. | cyclopropylmethyl | 4-((S)-1-methylpyrrolidin-3-yl)-phenyl |
| 1594. | cyclopropylmethyl | 4-((R)-1-methylpyrrolidin-3-yl)-phenyl |
| 1595. | cyclopropylmethyl | 4-(2,2-dimethylpyrrolidin-1-yl)-phenyl |
| 1596. | cyclopropylmethyl | 4-(3,3-dimethylpyrrolidin-1-yl)-phenyl |
| 1597. | cyclopropylmethyl | 4-(2-trifluoromethylpyrrolidin-1-yl)-phenyl |
| 1598. | cyclopropylmethyl | 4-((S)-2-trifluoromethylpyrrolidin-1-yl)-phenyl |
| 1599. | cyclopropylmethyl | 4-((R)-2-trifluoromethylpyrrolidin-1-yl)-phenyl |
| 1600. | cyclopropylmethyl | 4-(3-trifluoromethylpyrrolidin-1-yl)-phenyl |
| 1601. | cyclopropylmethyl | 4-((S)-3-trifluoromethylpyrrolidin-1-yl)-phenyl |
| 1602. | cyclopropylmethyl | 4-((R)-3-trifluoromethylpyrrolidin-1-yl)-phenyl |
| 1603. | cyclopropylmethyl | 4-(2-methoxymethylpyrrolidin-1-yl)-phenyl |
| 1604. | cyclopropylmethyl | 4-((S)-2-methoxymethylpyrrolidin-1-yl)-phenyl |
| 1605. | cyclopropylmethyl | 4-((R)-2-methoxymethylpyrrolidin-1-yl)-phenyl |
| 1606. | cyclopropylmethyl | 4-(2-oxopyrrolidin-1-yl)-phenyl |
| 1607. | cyclopropylmethyl | 4-(2-oxo-oxazolidin-3-yl)-phenyl |
| 1608. | cyclopropylmethyl | 4-(piperidin-1-yl)-phenyl |
| 1609. | cyclopropylmethyl | 4-(2-methylpiperidin-1-yl)-phenyl |
| 1610. | cyclopropylmethyl | 4-((S)-2-methylpiperidin-1-yl)-phenyl |
| 1611. | cyclopropylmethyl | 4-((R)-2-methylpiperidin-1-yl)-phenyl |
| 1612. | cyclopropylmethyl | 4-(piperazin-1-yl)-phenyl |
| 1613. | cyclopropylmethyl | 4-(4-methylpiperazin-1-yl)-phenyl |

TABLE A-continued

| No. | R¹ | Ar |
|---|---|---|
| 1614. | cyclopropylmethyl | 4-(morpholin-4-yl)-phenyl |
| 1615. | cyclopropylmethyl | 4-(thiomorpholin-4-yl)-phenyl |
| 1616. | cyclopropylmethyl | 4-(1-oxo-thiomorpholin-4-yl)-phenyl |
| 1617. | cyclopropylmethyl | 4-(1,1-dioxo-thiomorpholin-4-yl)-phenyl |
| 1618. | cyclopropylmethyl | 4-(pyrrol-1-yl)-phenyl |
| 1619. | cyclopropylmethyl | 4-(pyrrol-2-yl)-phenyl |
| 1620. | cyclopropylmethyl | 4-(pyrrol-3-yl)-phenyl |
| 1621. | cyclopropylmethyl | 4-(1-methylpyrrol-2-yl)-phenyl |
| 1622. | cyclopropylmethyl | 4-(1-methylpyrrol-3-yl)-phenyl |
| 1623. | cyclopropylmethyl | 4-(furan-2-yl)-phenyl |
| 1624. | cyclopropylmethyl | 4-(furan-3-yl)-phenyl |
| 1625. | cyclopropylmethyl | 4-(thiophen-2-yl)-phenyl |
| 1626. | cyclopropylmethyl | 4-(thiophen-3-yl)-phenyl |
| 1627. | cyclopropylmethyl | 4-(5-propylthien-2-yl)-phenyl |
| 1628. | cyclopropylmethyl | 4-(pyrazol-1-yl)-phenyl |
| 1629. | cyclopropylmethyl | 4-(pyrazol-3-yl)-phenyl |
| 1630. | cyclopropylmethyl | 4-(pyrazol-4-yl)-phenyl |
| 1631. | cyclopropylmethyl | 4-(1-methyl-1H-pyrazol-4-yl)-phenyl |
| 1632. | cyclopropylmethyl | 4-(1-ethyl-1H-pyrazol-4-yl)-phenyl |
| 1633. | cyclopropylmethyl | 4-(1-methyl-1H-pyrazol-5-yl)-phenyl |
| 1634. | cyclopropylmethyl | 4-(1H-imidazol-2-yl)-phenyl |
| 1635. | cyclopropylmethyl | 4-(imidazol-1-yl)-phenyl |
| 1636. | cyclopropylmethyl | 4-(1-methylimidazol-2-yl)-phenyl |
| 1637. | cyclopropylmethyl | 4-(oxazol-2-yl)-phenyl |
| 1638. | cyclopropylmethyl | 4-(oxazol-4-yl)-phenyl |
| 1639. | cyclopropylmethyl | 4-(oxazol-5-yl)-phenyl |
| 1640. | cyclopropylmethyl | 4-(isoxazol-3-yl)-phenyl |
| 1641. | cyclopropylmethyl | 4-(isoxazol-4-yl)-phenyl |
| 1642. | cyclopropylmethyl | 4-(isoxazol-5-yl)-phenyl |
| 1643. | cyclopropylmethyl | 4-([1,2,3]-triazol-1-yl)-phenyl |
| 1644. | cyclopropylmethyl | 4-([1,2,4]-triazol-1-yl)-phenyl |
| 1645. | cyclopropylmethyl | 4-([1,2,3]-triazol-2-yl)-phenyl |
| 1646. | cyclopropylmethyl | 4-(4H-[1,2,4]-triazol-3-yl)-phenyl |
| 1647. | cyclopropylmethyl | 4-([1,2,4]-triazol-4-yl)-phenyl |
| 1648. | cyclopropylmethyl | 4-(2H-[1,2,3]-triazol-4-yl)-phenyl |
| 1649. | cyclopropylmethyl | 4-(4-methyl-4H-[1,2,4]-triazol-3-yl)-phenyl |
| 1650. | cyclopropylmethyl | 4-(2-methyl-2H-[1,2,3]-triazol-4-yl)-phenyl |
| 1651. | cyclopropylmethyl | 4-([1,3,4]-oxadiazol-2-yl)-phenyl |
| 1652. | cyclopropylmethyl | 4-([1,2,4]-oxadiazol-3-yl)-phenyl |
| 1653. | cyclopropylmethyl | 4-([1,2,4]-oxadiazol-5-yl)-phenyl |
| 1654. | cyclopropylmethyl | 4-([1,2,3]-oxadiazol-4-yl)-phenyl |
| 1655. | cyclopropylmethyl | 4-([1,2,3]-oxadiazol-5-yl)-phenyl |
| 1656. | cyclopropylmethyl | 4-([1,2,3]-thiadiazol-4-yl)-phenyl |
| 1657. | cyclopropylmethyl | 4-(1H-tetrazol-5-yl)-phenyl |
| 1658. | cyclopropylmethyl | 4-(tetrazol-1-yl)-phenyl |
| 1659. | cyclopropylmethyl | 4-(2-methyl-2H-tetrazol-5-yl)-phenyl |
| 1660. | cyclopropylmethyl | 4-(1-methyl-1H-tetrazol-5-yl)-phenyl |
| 1661. | cyclopropylmethyl | 4-furazan-3-yl-phenyl |
| 1662. | cyclopropylmethyl | 4-(pyrid-2-yl)-phenyl |
| 1663. | cyclopropylmethyl | 4-(pyrid-3-yl)-phenyl |
| 1664. | cyclopropylmethyl | 4-(pyrid-4-yl)-phenyl |
| 1665. | cyclopropylmethyl | 4-(pyrimidin-2-yl)-phenyl |
| 1666. | cyclopropylmethyl | 4-(pyrimidin-4-yl)-phenyl |
| 1667. | cyclopropylmethyl | 4-(pyrimidin-5-yl)-phenyl |
| 1668. | cyclopropylmethyl | 5-isopropylthiophen-2-yl |
| 1669. | cyclopropylmethyl | 2-chlorothiophen-5-yl |
| 1670. | cyclopropylmethyl | 2,5-dichlorothiophen-4-yl |
| 1671. | cyclopropylmethyl | 2,3-dichlorothiophen-5-yl |
| 1672. | cyclopropylmethyl | 2-chloro-3-nitrothiophen-5-yl |
| 1673. | cyclopropylmethyl | 2-(phenylsulfonyl)-thiophen-5-yl |
| 1674. | cyclopropylmethyl | 2-(pyridin-2-yl)thiophen-5-yl |
| 1675. | cyclopropylmethyl | 2-(5-(trifluoromethyl)isoxazol-3-yl)-thiophen-5-yl |
| 1676. | cyclopropylmethyl | 2-(2-methylthiazol-4-yl)-thiophen-5-yl |
| 1677. | cyclopropylmethyl | 1-methyl-1H-imidazol-4-yl |
| 1678. | cyclopropylmethyl | 1,2-dimethyl-1H-imidazol-4-yl |
| 1679. | cyclopropylmethyl | 3,5-dimethylisoxazol-4-yl |
| 1680. | cyclopropylmethyl | thiazol-2-yl |
| 1681. | cyclopropylmethyl | 4-methylthiazol-2-yl |
| 1682. | cyclopropylmethyl | 4-isopropylthiazol-2-yl |
| 1683. | cyclopropylmethyl | 4-trifluoromethylthiazol-2-yl |
| 1684. | cyclopropylmethyl | 5-methylthiazol-2-yl |
| 1685. | cyclopropylmethyl | 5-isopropylthiazol-2-yl |
| 1686. | cyclopropylmethyl | 5-trifluoromethylthiazol-2-yl |
| 1687. | cyclopropylmethyl | 2,4-dimethylthiazol-5-yl |
| 1688. | cyclopropylmethyl | 2-acetamido-4-methylthiazol-5-yl |
| 1689. | cyclopropylmethyl | 4H-[1,2,4]triazol-3-yl |
| 1690. | cyclopropylmethyl | 5-methyl-4H-[1,2,4]triazol-3-yl |

TABLE A-continued

| No. | R¹ | Ar |
|---|---|---|
| 1691. | cyclopropylmethyl | 4-methyl-4H-[1,2,4]triazol-3-yl |
| 1692. | cyclopropylmethyl | 5-isopropyl-4H-[1,2,4]triazol-3-yl |
| 1693. | cyclopropylmethyl | 5-trifluoromethyl-4H-[1,2,4]triazol-3-yl |
| 1694. | cyclopropylmethyl | 4,5-dimethyl-4H-[1,2,4]triazol-3-yl |
| 1695. | cyclopropylmethyl | 5-isopropyl-4-methyl-4H-[1,2,4]triazol-3-yl |
| 1696. | cyclopropylmethyl | 5-trifluoromethyl-4-methyl-4H-[1,2,4]triazol-3-yl |
| 1697. | cyclopropylmethyl | [1,3,4]thiadiazol-2-yl |
| 1698. | cyclopropylmethyl | 5-methyl-[1,3,4]thiadiazol-2-yl |
| 1699. | cyclopropylmethyl | 5-isopropyl-[1,3,4]thiadiazol-2-yl |
| 1700. | cyclopropylmethyl | 5-trifluoromethyl-[1,3,4]thiadiazol-2-yl |
| 1701. | cyclopropylmethyl | 3-bromo-2-chloropyrid-5-yl |
| 1702. | cyclopropylmethyl | 2-(4-morpholino)-pyrid-5-yl |
| 1703. | cyclopropylmethyl | 2-phenoxypyrid-5-yl |
| 1704. | cyclopropylmethyl | (2-isopropyl)-pyrimidin-5-yl |
| 1705. | cyclopropylmethyl | (5-isopropyl)-pyrimidin-2-yl |
| 1706. | cyclopropylmethyl | 8-quinolyl |
| 1707. | cyclopropylmethyl | 5-isoquinolyl |
| 1708. | cyclopropylmethyl | 2-(trifluoroacetyl)-1,2,3,4-tetrahydroisoquinolin-7-yl |
| 1709. | cyclopropylmethyl | 5-chloro-3-methylbenzothiophen-2-yl |
| 1710. | cyclopropylmethyl | 3,4-dihydro-4-methyl-2H-benzo[b][1,4]oxazinyl |
| 1711. | cyclopropylmethyl | benzothiazol-6-yl |
| 1712. | cyclopropylmethyl | benzo[2,1,3]oxadiazol-4-yl |
| 1713. | cyclopropylmethyl | 5-chlorobenzo[2,1,3]oxadiazol-4-yl |
| 1714. | cyclopropylmethyl | 7-chlorobenzo[2,1,3]oxadiazol-4-yl |
| 1715. | cyclopropylmethyl | benzo[2,1,3]thiadiazol-4-yl |
| 1716. | allyl | 4-methylphenyl |
| 1717. | allyl | 4-ethylphenyl |
| 1718. | allyl | 4-propylphenyl |
| 1719. | allyl | 4-isopropylphenyl |
| 1720. | allyl | 4-sec-butylphenyl |
| 1721. | allyl | 4-isobutylphenyl |
| 1722. | allyl | 4-(1,1-dimethylpropyl)-phenyl |
| 1723. | allyl | 4-vinylphenyl |
| 1724. | allyl | 4-isopropenylphenyl |
| 1725. | allyl | 4-fluorophenyl |
| 1726. | allyl | 4-chlorophenyl |
| 1727. | allyl | 4-bromophenyl |
| 1728. | allyl | 4-(fluoromethyl)phenyl |
| 1729. | allyl | 3-(fluoromethyl)phenyl |
| 1730. | allyl | 2-(fluoromethyl)phenyl |
| 1731. | allyl | 4-(difluoromethyl)phenyl |
| 1732. | allyl | 3-(difluoromethyl)phenyl |
| 1733. | allyl | 2-(difluoromethyl)phenyl |
| 1734. | allyl | 4-(trifluoromethyl)phenyl |
| 1735. | allyl | 3-(trifluoromethyl)phenyl |
| 1736. | allyl | 2-(trifluoromethyl)phenyl |
| 1737. | allyl | 4-(1-fluoroethyl)-phenyl |
| 1738. | allyl | 4-((S)-1-fluoroethyl)-phenyl |
| 1739. | allyl | 4-((R)-1-fluoroethyl)-phenyl |
| 1740. | allyl | 4-(2-fluoroethyl)-phenyl |
| 1741. | allyl | 4-(1,1-difluoroethyl)-phenyl |
| 1742. | allyl | 4-(2,2-difluoroethyl)-phenyl |
| 1743. | allyl | 4-(2,2,2-trifluoroethyl)-phenyl |
| 1744. | allyl | 4-(3-fluoropropyl)-phenyl |
| 1745. | allyl | 4-(2-fluoropropyl)-phenyl |
| 1746. | allyl | 4-((S)-2-fluoropropyl)-phenyl |
| 1747. | allyl | 4-((R)-2-fluoropropyl)-phenyl |
| 1748. | allyl | 4-(3,3-difluoropropyl)-phenyl |
| 1749. | allyl | 4-(3,3,3-trifluoropropyl)-phenyl |
| 1750. | allyl | 4-(1-fluoro-1-methylethyl)-phenyl |
| 1751. | allyl | 4-(2-fluoro-1-methylethyl)-phenyl |
| 1752. | allyl | 4-((S)-2-fluoro-1-methylethyl)-phenyl |
| 1753. | allyl | 4-((R)-2-fluoro-1-methylethyl)-phenyl |
| 1754. | allyl | 4-(2,2-difluoro-1-methylethyl)-phenyl |
| 1755. | allyl | 4-((S)-2,2-difluoro-1-methylethyl)-phenyl |
| 1756. | allyl | 4-((R)-2,2-difluoro-1-methylethyl)-phenyl |
| 1757. | allyl | 4-(2,2,2-trifluoro-1-methylethyl)-phenyl |
| 1758. | allyl | 4-((S)-2,2,2-trifluoro-1-methylethyl)-phenyl |
| 1759. | allyl | 4-((R)-2,2,2-trifluoro-1-methylethyl)-phenyl |
| 1760. | allyl | 4-(2-fluoro-1-fluoromethylethyl)-phenyl |
| 1761. | allyl | 4-(1-difluoromethyl-2,2-difluoroethyl)-phenyl |
| 1762. | allyl | 4-(1,1-dimethyl-2-fluoroethyl)-phenyl |
| 1763. | allyl | 4-methoxyphenyl |
| 1764. | allyl | 4-ethoxyphenyl |
| 1765. | allyl | 4-propoxyphenyl |
| 1766. | allyl | 4-isopropoxyphenyl |
| 1767. | allyl | 4-butoxyphenyl |

TABLE A-continued

| No. | R¹ | Ar |
|---|---|---|
| 1768. | allyl | 4-(fluoromethoxy)-phenyl |
| 1769. | allyl | 4-(difluoromethoxy)-phenyl |
| 1770. | allyl | 4-(trifluoromethoxy)-phenyl |
| 1771. | allyl | 3-(trifluoromethoxy)-phenyl |
| 1772. | allyl | 4-(2-fluoroethoxy)-phenyl |
| 1773. | allyl | 4-(2,2-difluoroethoxy)-phenyl |
| 1774. | allyl | 4-(2,2,2-trifluoroethoxy)-phenyl |
| 1775. | allyl | 4-(1,1,2,2-tetrafluoroethoxy)-phenyl |
| 1776. | allyl | 4-cyclopropylphenyl |
| 1777. | allyl | 4-cyclobutylphenyl |
| 1778. | allyl | 4-cyclopentylphenyl |
| 1779. | allyl | 4-(2,2-difluorocyclopropyl)-phenyl |
| 1780. | allyl | 3,4-difluorophenyl |
| 1781. | allyl | 4-bromo-3-fluorophenyl |
| 1782. | allyl | 4-bromo-2-fluorophenyl |
| 1783. | allyl | 4-bromo-2,5-difluorophenyl |
| 1784. | allyl | 2-fluoro-4-isopropylphenyl |
| 1785. | allyl | 3-fluoro-4-isopropylphenyl |
| 1786. | allyl | 4-(1-hydroxy-1-methylethyl)-phenyl |
| 1787. | allyl | 4-(2-hydroxy-2-methylpropyl)-phenyl |
| 1788. | allyl | 4-acetylphenyl |
| 1789. | allyl | 4-carboxyphenyl |
| 1790. | allyl | 4-cyanophenyl |
| 1791. | allyl | 4-hydroxyphenyl |
| 1792. | allyl | 4-(O-benzyl)-phenyl |
| 1793. | allyl | 4-(2-methoxyethoxy)-phenyl |
| 1794. | allyl | 4-(CH₂—N(CH₃)₂)-phenyl |
| 1795. | allyl | 4-(NH—CO—NH₂)-phenyl |
| 1796. | allyl | 4-(methylsulfanyl)-phenyl |
| 1797. | allyl | 4-(fluoromethylsulfanyl)-phenyl |
| 1798. | allyl | 4-(difluoromethylsulfanyl)-phenyl |
| 1799. | allyl | 4-(trifluoromethylsulfanyl)-phenyl |
| 1800. | allyl | 4-(methylsulfonyl)-phenyl |
| 1801. | allyl | 4-(N-methoxy-N-methyl-amino)-phenyl |
| 1802. | allyl | 4-(methoxyamino)-phenyl |
| 1803. | allyl | 4-(ethoxyamino)-phenyl |
| 1804. | allyl | 4-(N-methylaminooxy)-phenyl |
| 1805. | allyl | 4-(N,N-dimethylaminooxy)-phenyl |
| 1806. | allyl | 4-(azetidin-1-yl)-phenyl |
| 1807. | allyl | 4-(2-methylazetidin-1-yl)-phenyl |
| 1808. | allyl | 4-((S)-2-methylazetidin-1-yl)-phenyl |
| 1809. | allyl | 4-((R)-2-methylazetidin-1-yl)-phenyl |
| 1810. | allyl | 4-(3-fluoroazetidin-1-yl)-phenyl |
| 1811. | allyl | 4-(3-methoxyazetidin-1-yl)-phenyl |
| 1812. | allyl | 4-(3-hydroxyazetidin-1-yl)-phenyl |
| 1813. | allyl | 4-(pyrrolidin-1-yl)-phenyl |
| 1814. | allyl | 4-(pyrrolidin-2-yl)-phenyl |
| 1815. | allyl | 4-((S)-pyrrolidin-2-yl)-phenyl |
| 1816. | allyl | 4-((R)-pyrrolidin-2-yl)-phenyl |
| 1817. | allyl | 4-(pyrrolidin-3-yl)-phenyl |
| 1818. | allyl | 4-((S)-pyrrolidin-3-yl)-phenyl |
| 1819. | allyl | 4-((R)-pyrrolidin-3-yl)-phenyl |
| 1820. | allyl | 4-(2-fluoropyrrolidin-1-yl)-phenyl |
| 1821. | allyl | 4-((S)-2-fluoropyrrolidin-1-yl)-phenyl |
| 1822. | allyl | 4-((R)-2-fluoropyrrolidin-1-yl)-phenyl |
| 1823. | allyl | 4-(3-fluoropyrrolidin-1-yl)-phenyl |
| 1824. | allyl | 4-((S)-3-fluoropyrrolidin-1-yl)-phenyl |
| 1825. | allyl | 4-((R)-3-fluoropyrrolidin-1-yl)-phenyl |
| 1826. | allyl | 4-(2,2-difluoropyrrolidin-1-yl)-phenyl |
| 1827. | allyl | 4-(3,3-difluoropyrrolidin-1-yl)-phenyl |
| 1828. | allyl | 4-(2-methylpyrrolidin-1-yl)-phenyl |
| 1829. | allyl | 4-((S)-2-methylpyrrolidin-1-yl)-phenyl |
| 1830. | allyl | 4-((R)-2-methylpyrrolidin-1-yl)-phenyl |
| 1831. | allyl | 4-(3-methylpyrrolidin-1-yl)-phenyl |
| 1832. | allyl | 4-((S)-3-methylpyrrolidin-1-yl)-phenyl |
| 1833. | allyl | 4-((R)-3-methylpyrrolidin-1-yl)-phenyl |
| 1834. | allyl | 4-(1-methylpyrrolidin-2-yl)-phenyl |
| 1835. | allyl | 4-((S)-1-methylpyrrolidin-2-yl)-phenyl |
| 1836. | allyl | 4-((R)-1-methylpyrrolidin-2-yl)-phenyl |
| 1837. | allyl | 4-(1-methylpyrrolidin-3-yl)-phenyl |
| 1838. | allyl | 4-((S)-1-methylpyrrolidin-3-yl)-phenyl |
| 1839. | allyl | 4-((R)-1-methylpyrrolidin-3-yl)-phenyl |
| 1840. | allyl | 4-(2,2-dimethylpyrrolidin-1-yl)-phenyl |
| 1841. | allyl | 4-(3,3-dimethylpyrrolidin-1-yl)-phenyl |
| 1842. | allyl | 4-(2-trifluoromethylpyrrolidin-1-yl)-phenyl |
| 1843. | allyl | 4-((S)-2-trifluoromethylpyrrolidin-1-yl)-phenyl |
| 1844. | allyl | 4-((R)-2-trifluoromethylpyrrolidin-1-yl)-phenyl |

TABLE A-continued

| No. | R¹ | Ar |
|---|---|---|
| 1845. | allyl | 4-(3-trifluoromethylpyrrolidin-1-yl)-phenyl |
| 1846. | allyl | 4-((S)-3-trifluoromethylpyrrolidin-1-yl)-phenyl |
| 1847. | allyl | 4-((R)-3-trifluoromethylpyrrolidin-1-yl)-phenyl |
| 1848. | allyl | 4-(2-methoxymethylpyrrolidin-1-yl)-phenyl |
| 1849. | allyl | 4-((S)-2-methoxymethylpyrrolidin-1-yl)-phenyl |
| 1850. | allyl | 4-((R)-2-methoxymethylpyrrolidin-1-yl)-phenyl |
| 1851. | allyl | 4-(2-oxopyrrolidin-1-yl)-phenyl |
| 1852. | allyl | 4-(2-oxo-oxazolidin-3-yl)-phenyl |
| 1853. | allyl | 4-(piperidin-1-yl)-phenyl |
| 1854. | allyl | 4-(2-methylpiperidin-1-yl)-phenyl |
| 1855. | allyl | 4-((S)-2-methylpiperidin-1-yl)-phenyl |
| 1856. | allyl | 4-((R)-2-methylpiperidin-1-yl)-phenyl |
| 1857. | allyl | 4-(piperazin-1-yl)-phenyl |
| 1858. | allyl | 4-(4-methylpiperazin-1-yl)-phenyl |
| 1859. | allyl | 4-(morpholin-4-yl)-phenyl |
| 1860. | allyl | 4-(thiomorpholin-4-yl)-phenyl |
| 1861. | allyl | 4-(1-oxo-thiomorpholin-4-yl)-phenyl |
| 1862. | allyl | 4-(1,1-dioxo-thiomorpholin-4-yl)-phenyl |
| 1863. | allyl | 4-(pyrrol-1-yl)-phenyl |
| 1864. | allyl | 4-(pyrrol-2-yl)-phenyl |
| 1865. | allyl | 4-(pyrrol-3-yl)-phenyl |
| 1866. | allyl | 4-(1-methylpyrrol-2-yl)-phenyl |
| 1867. | allyl | 4-(1-methylpyrrol-3-yl)-phenyl |
| 1868. | allyl | 4-(furan-2-yl)-phenyl |
| 1869. | allyl | 4-(furan-3-yl)-phenyl |
| 1870. | allyl | 4-(thiophen-2-yl)-phenyl |
| 1871. | allyl | 4-(thiophen-3-yl)-phenyl |
| 1872. | allyl | 4-(5-propylthien-2-yl)-phenyl |
| 1873. | allyl | 4-(pyrazol-1-yl)-phenyl |
| 1874. | allyl | 4-(pyrazol-3-yl)-phenyl |
| 1875. | allyl | 4-(pyrazol-4-yl)-phenyl |
| 1876. | allyl | 4-(1-methyl-1H-pyrazol-4-yl)-phenyl |
| 1877. | allyl | 4-(1-ethyl-1H-pyrazol-4-yl)-phenyl |
| 1878. | allyl | 4-(1-methyl-1H-pyrazol-5-yl)-phenyl |
| 1879. | allyl | 4-(1H-imidazol-2-yl)-phenyl |
| 1880. | allyl | 4-(imidazol-1-yl)-phenyl |
| 1881. | allyl | 4-(1-methylimidazol-2-yl)-phenyl |
| 1882. | allyl | 4-(oxazol-2-yl)-phenyl |
| 1883. | allyl | 4-(oxazol-4-yl)-phenyl |
| 1884. | allyl | 4-(oxazol-5-yl)-phenyl |
| 1885. | allyl | 4-(isoxazol-3-yl)-phenyl |
| 1886. | allyl | 4-(isoxazol-4-yl)-phenyl |
| 1887. | allyl | 4-(isoxazol-5-yl)-phenyl |
| 1888. | allyl | 4-([1,2,3]-triazol-1-yl)-phenyl |
| 1889. | allyl | 4-([1,2,4]-triazol-1-yl)-phenyl |
| 1890. | allyl | 4-([1,2,3]-triazol-2-yl)-phenyl |
| 1891. | allyl | 4-(4H-[1,2,4]-triazol-3-yl)-phenyl |
| 1892. | allyl | 4-([1,2,4]-triazol-4-yl)-phenyl |
| 1893. | allyl | 4-(2H-[1,2,3]-triazol-4-yl)-phenyl |
| 1894. | allyl | 4-(4-methyl-4H-[1,2,4]-triazol-3-yl)-phenyl |
| 1895. | allyl | 4-(2-methyl-2H-[1,2,3]-triazol-4-yl)-phenyl |
| 1896. | allyl | 4-([1,3,4]-oxadiazol-2-yl)-phenyl |
| 1897. | allyl | 4-([1,2,4]-oxadiazol-3-yl)-phenyl |
| 1898. | allyl | 4-([1,2,4]-oxadiazol-5-yl)-phenyl |
| 1899. | allyl | 4-([1,2,3]-oxadiazol-4-yl)-phenyl |
| 1900. | allyl | 4-([1,2,3]-oxadiazol-5-yl)-phenyl |
| 1901. | allyl | 4-([1,2,3]-thiadiazol-4-yl)-phenyl |
| 1902. | allyl | 4-(1H-tetrazol-5-yl)-phenyl |
| 1903. | allyl | 4-(tetrazol-1-yl)-phenyl |
| 1904. | allyl | 4-(2-methyl-2H-tetrazol-5-yl)-phenyl |
| 1905. | allyl | 4-(1-methyl-1H-tetrazol-5-yl)-phenyl |
| 1906. | allyl | 4-furazan-3-yl-phenyl |
| 1907. | allyl | 4-(pyrid-2-yl)-phenyl |
| 1908. | allyl | 4-(pyrid-3-yl)-phenyl |
| 1909. | allyl | 4-(pyrid-4-yl)-phenyl |
| 1910. | allyl | 4-(pyrimidin-2-yl)-phenyl |
| 1911. | allyl | 4-(pyrimidin-4-yl)-phenyl |
| 1912. | allyl | 4-(pyrimidin-5-yl)-phenyl |
| 1913. | allyl | 5-isopropylthiophen-2-yl |
| 1914. | allyl | 2-chlorothiophen-5-yl |
| 1915. | allyl | 2,5-dichlorothiophen-4-yl |
| 1916. | allyl | 2,3-dichlorothiophen-5-yl |
| 1917. | allyl | 2-chloro-3-nitrothiophen-5-yl |
| 1918. | allyl | 2-(phenylsulfonyl)-thiophen-5-yl |
| 1919. | allyl | 2-(pyridin-2-yl)thiophen-5-yl |
| 1920. | allyl | 2-(5-(trifluoromethyl)isoxazol-3-yl)-thiophen-5-yl |
| 1921. | allyl | 2-(2-methylthiazol-4-yl)-thiophen-5-yl |

TABLE A-continued

| No. | R¹ | Ar |
|---|---|---|
| 1922. | allyl | 1-methyl-1H-imidazol-4-yl |
| 1923. | allyl | 1,2-dimethyl-1H-imidazol-4-yl |
| 1924. | allyl | 3,5-dimethylisoxazol-4-yl |
| 1925. | allyl | thiazol-2-yl |
| 1926. | allyl | 4-methylthiazol-2-yl |
| 1927. | allyl | 4-isopropylthiazol-2-yl |
| 1928. | allyl | 4-trifluoromethylthiazol-2-yl |
| 1929. | allyl | 5-methylthiazol-2-yl |
| 1930. | allyl | 5-isopropylthiazol-2-yl |
| 1931. | allyl | 5-trifluoromethylthiazol-2-yl |
| 1932. | allyl | 2,4-dimethylthiazol-5-yl |
| 1933. | allyl | 2-acetamido-4-methylthiazol-5-yl |
| 1934. | allyl | 4H-[1,2,4]triazol-3-yl |
| 1935. | allyl | 5-methyl-4H-[1,2,4]triazol-3-yl |
| 1936. | allyl | 4-methyl-4H-[1,2,4]triazol-3-yl |
| 1937. | allyl | 5-isopropyl-4H-[1,2,4]triazol-3-yl |
| 1938. | allyl | 5-trifluoromethyl-4H-[1,2,4]triazol-3-yl |
| 1939. | allyl | 4,5-dimethyl-4H-[1,2,4]triazol-3-yl |
| 1940. | allyl | 5-isopropyl-4-methyl-4H-[1,2,4]triazol-3-yl |
| 1941. | allyl | 5-trifluoromethyl-4-methyl-4H-[1,2,4]triazol-3-yl |
| 1942. | allyl | [1,3,4]thiadiazol-2-yl |
| 1943. | allyl | 5-methyl-[1,3,4]thiadiazol-2-yl |
| 1944. | allyl | 5-isopropyl-[1,3,4]thiadiazol-2-yl |
| 1945. | allyl | 5-trifluoromethyl-[1,3,4]thiadiazol-2-yl |
| 1946. | allyl | 3-bromo-2-chloropyrid-5-yl |
| 1947. | allyl | 2-(4-morpholino)-pyrid-5-yl |
| 1948. | allyl | 2-phenoxypyrid-5-yl |
| 1949. | allyl | (2-isopropyl)-pyrimidin-5-yl |
| 1950. | allyl | (5-isopropyl)-pyrimidin-2-yl |
| 1951. | allyl | 8-quinolyl |
| 1952. | allyl | 5-isoquinolyl |
| 1953. | allyl | 2-(trifluoroacetyl)-1,2,3,4-tetrahydroisoquinolin-7-yl |
| 1954. | allyl | 5-chloro-3-methylbenzothiophen-2-yl |
| 1955. | allyl | 3,4-dihydro-4-methyl-2H-benzo[b][1,4]oxazinyl |
| 1956. | allyl | benzothiazol-6-yl |
| 1957. | allyl | benzo[2,1,3]oxadiazol-4-yl |
| 1958. | allyl | 5-chlorobenzo[2,1,3]oxadiazol-4-yl |
| 1959. | allyl | 7-chlorobenzo[2,1,3]oxadiazol-4-yl |
| 1960. | allyl | benzo[2,1,3]thiadiazol-4-yl |
| 1961. | allyl | 6-chloroimidazo[2,1-b]thiazolyl |

Compounds I of the present invention can be synthesized as outlined in the synthetic route below.

Scheme 1:

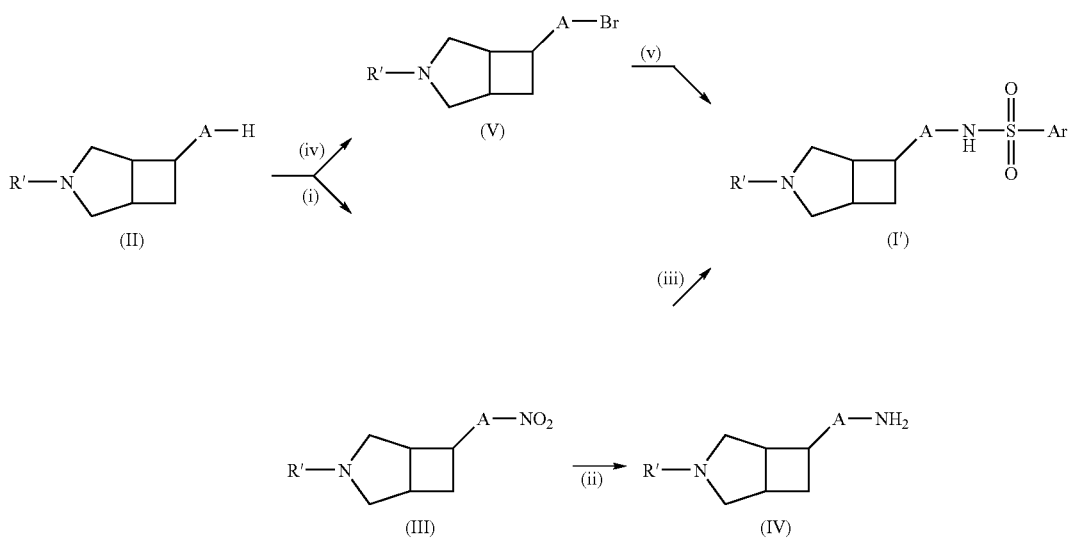

In scheme 1, A and Ar are as defined above. R' is either R$^1$ or is a precursor of R$^1$.

Compound (I'), which is either the desired product (I) or a precursor thereof, can be obtained by nitrating the aryl or hetaryl moiety A-H of an azabicycloheptane (II). Reduction of the nitro group and reaction of the formed amino functionality with a suitable sulfonic acid derivative provides compound (I') (steps (i), (ii) and (iii)). Alternatively, the aryl or hetaryl moiety A-H of the azabicycloheptane (II) is brominated and then reacted with a suitable sulfonic acid derivative.

The reaction of step (i) takes place under the reaction conditions which are customary for a nitration reaction on an aromatic radical and which are described, for example, in Jerry March, Advanced Organic Chemistry, John Wiley, 3$^{rd}$ edition, page 468ff, Tetrahedron 1999, 55(33), pp. 10243-10252, J. Med. Chem. 1997, 40(22), pp. 3679-3686 and Synthetic Communications, 1993, 23(5), pp. 591-599. For example, compound (II) is reacted with concentrated nitric acid or a nitrate, such as potassium or sodium nitrate, in the presence of concentrated sulfuric acid. The nitration reaction generally leads to the formation of different regioisomers, such as the ortho, para and meta product. Generally, the meta product I essentially is not formed. However, customarily both ortho and para products are obtained, the para product being generally the predominant species. By separating the ortho and para products, compounds of formula I, wherein A is 1,4-aryl or hetaryl as well as compounds I, wherein A is 1,2-aryl or hetaryl, are accessible via the reaction path shown in scheme 1.

In step (ii), the nitro group in (III) is reduced to an NH$_2$ group. Subsequently, the NH$_2$ group can be converted into a —NR$^{5'}$ group, in which R$^{5'}$ has the meanings different from hydrogen which are specified for R$^5$. The reaction conditions which are required for step (ii) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction is achieved, for example, by reacting the nitro compound III with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as NiCl$_2$(P(phenyl)$_3$)$_2$, or COCl$_2$, (see Ono et al. Chem. Ind. (London), 1983 p. 480), or using NaBH$_2$S$_3$ (see Lalancette et al. Can. J. Chem. 49, 1971, p. 2990), with it being possible to carry out these reductions, depending on the given reagent, in substance or in a solvent or diluent. Alternatively, the reduction of VII to VIII can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound VII, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of VII with tin(II) chloride is preferably carried out in an inert organic solvent, preferably an alcohol such as methanol, ethanol, isopropanol or butanol.

Step (iii) is preferably carried out in the presence of a base, according to standard procedures in the art. In the reaction depicted in the above scheme, step (iii) takes place under the reaction conditions which are customary for preparing arylsulfonamide compounds or arylsulfonic esters, respectively, and which are described, for example, in J. March, Advanced Organic Chemistry, 3$^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction with Cl—SO$_2$—Ar is customarily carried out in the presence of an auxiliary base. Suitable bases are inorganic bases, such as sodium carbonate or potassium carbonate, or sodium hydrogencarbonate or potassium hydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound II.

Instead of the nitration step (i), the compounds I' are also accessible by bromination of compound (II). The bromo substituent of the A group may then be replaced by reacting with an appropriate sulfonamide ArSO$_2$NH$_2$, e.g. under microwave conditions. Pd, especially Pd(0), or Cu catalysts may also be used for coupling (see, e.g. Org. Lett. 2000, 2, 1101; J. Am. Chem. Soc. 2002, 124, 6043; Org. Lett. 2003, 5, 4373; Tetrahedron Lett. 2003, 44, 3385). This reaction path is especially useful in cases where the corresponding sulfonyl chloride is not available. Alternatively, the bromo substituent may be replaced by an amino substituent, e.g. by reacting with benzophenone imine in the presence of a Pd catalyst (see, e.g. J. Org. Chem. 2000, 65, 2612). The aminoaryl or hetaryl compound may then be subjected to the sulfonation of step (iii).

If R' is allyl, the allyl group can be cleaved to obtain a compound wherein R' is hydrogen. The cleavage of the allyl group is achieved, for example, by reacting I [R'=allyl] with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis(triphenylphosphine)palladium(0) or tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem 2002, 67(11) pp. 3718-3723). Alternatively, the cleavage of N-allyl can also be effected by reacting in the presence of rhodium compounds, such as tris(triphenylphosphine)chlororhodium(I), using methods known from the literature (see J. Chem. Soc., Perkin Transaction I: Organic and Bio-Organic Chemistry 1999 (21) pp. 3089-3104 and Tetrahedron Asymmetry 1997, 8(20), pp. 3387-3391).

If R' is benzyl, this substituent may also be cleaved to obtain a compound I' wherein R' is H. The reaction conditions for the cleavage are known in the art. Typically, the benzyl group is removed by a hydrogenation reaction in the presence of a suitable Pd catalyst, such as Pd on carbon or palladium hydroxide.

R' can also be a protective group. The protective group may be removed to yield a compound I' wherein R' is H. Suitable protective groups are known in the art and are, for example, selected from tert-butoxycarbonyl (boc), benzyloxycarbonyl (Cbz), 9-fluorenylmethoxycarbonyl (Fmoc), triphenylmethyl (Trt) and nitrobenzenesulfenyl (Nps). A preferred protective group is boc. The protective groups can be removed by known methods, such as treatment of the protected amine with an acid, e.g halogen acid, such as HCl or HBr, or trifluoroacetic acid, or by hydrogenation, optionally in the presence of a Pd catalyst.

The resulting compound [R'=H] can then be reacted, in a known manner, in the sense of an alkylation, with a compound $R^1$—X. In this compound, $R^1$ is $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl or $C_3$-$C_6$-cycloalkyl-$C_1$-$C_4$-alkyl and X is a nucleophilically displaceable leaving group, e.g. halogen, trifluoroacetate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

The alkylation can also be achieved, in the sense of a reductive amination, by reacting the compound I', wherein R'=H, with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

In case R' is hydrogen, the resulting sulfonamide can further be reacted with an acyl halide to obtain a compound of the formula I wherein $R^1$ is $C_1$-$C_3$-alkylcarbonyl. The carbonyl group in these compounds can be reduced, e.g. with diborane or lithium aluminium hydride, to obtain compounds of the general formula I, wherein $R^1$ is $C_2$-$C_4$-alkyl. The carbonyl group can also be reacted with a fluorinating agent to obtain a compound I wherein $R^1$ is 1,1-difluoroalkyl. Acylation and reduction can be achieved by standard methods, which are discussed in Jerry March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

The substituent Ar can be varied by either using different sulfonyl chlorides or by modifying the substituents of the cyclic group Ar after the formation of the sulfonylamide by known methods. For example, a bromine substituent of the Ar group may be replaced by an N-bound pyrrolidinyl group according to the procedure described in Tetrahedron Asym. 1999, 10, 1831. A bromine substituent of the Ar group may be replaced by an isopropenyl group according to a Stille coupling where the bromo compound is reacted with an alkenyl tributyl stannate in the presence of an appropriate Pd coupling catalyst, e.g. tetrakistriphenylphosphine palladium(0) (see, e.g. Tetrahedron, 2003, 59(34), 6545 and Bioorg. Med. Chem. 1999, 7(5), 665). The isopropenyl group may then be converted into the isopropyl group by known hydrogenation methods.

Starting compound (II) can be obtained according to following scheme 2 (see WO 94/00458, WO 00/23423 and Drugs and Future, 1998, 23(2), 191)

Scheme 2:

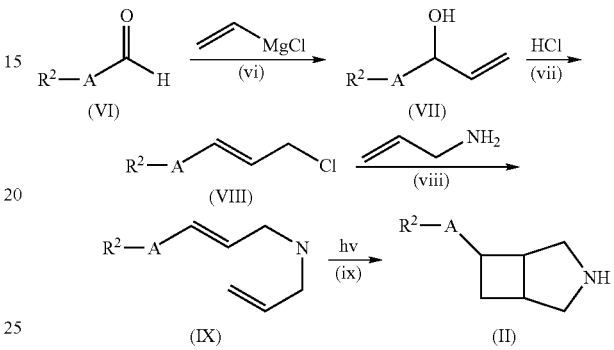

In scheme 2, A has the meanings as defined above. $R^2$ is H or a suitable substituent, such as halogen. If $R^2$ is Br, the resulting compound (II) can be subjected to step (v) without further reaction.

In step (vi), an aryl or hetaryl aldehyde is reacted with vinyl magnesium chloride to yield the enol (VII). (VIII), obtained via HCl addition and dehydration, is reacted with allyl amine to provide (IX) which is converted in a photochemical [2+2]-cycloaddition reaction into the azabicycloheptane (II). Compound (IX) having E-configuration (as shown in scheme 2) yields essentially the exo enantiomers, whereas the corresponding Z-isomer of (IX) provides essentially the endo isomers. The Z-isomer of (IX) can be obtained by reacting in step (vi) with aryl lithium species to form the hydroxylated species, which is then dehydrated and hydrogenated to give the Z-compound.

The exo and the endo enantiomers, respectively, can be separated by methods known in the art. For instance, the mixture of enantiomers may be treated with enantiomerically pure acids, e.g. with (+) or (−)-ditoluoyltartrate, to yield diastereomeric salts. The latter can be separated by standard separation methods such as chromatography, crystallization and the like. Alternatively, the mixture can be separated by means of a chiral chromatographic column.

Compound (II), where R' is H (as obtained according to scheme 2) can, if desired, be converted into an N-substituted compound by reacting with a suitable alkylating or acylating agent, as discussed above, before being subjected to the reaction steps of scheme 1.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The sulfonylchlorides Cl—SO$_2$—Ar are either commercially available or can be prepared according to standard synthetic methods. Sulfonylchlorides containing a fluorinated radical R$^a$ may be prepared by different synthetic routes, e.g. by reacting suitable hydroxy or oxo precursor (e.g. a compound Cl—SO$_2$—Ar, carrying a hydroxy or oxo substituted radical) with fluorinating reagents like DAST (diethylaminosulfurtrifluoride), morpholine-DAST, deoxofluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377). More conventionally, the hydroxy group of an aromatic compound which carries a hydroxy substituted radical but not a chlorosulfonyl group, is transformed into a leaving group which is then replace by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorous pentachloride (Eur. J. Med. Chem., 2002, 36, 809-828) and the like, yields the desired sulfonylchloride (Tetrahedron Letters, 1991, 33, 50 7787-7788)) Sulfonylchlorides may also be prepared by diazotation of suitable amine precursor Ar—NH$_2$ with sodium nitrite under acidic conditions and reaction with sulfur dioxide in acetic acid (scheme (iii); J. Org. Chem., 1960, 25, 1824-26;); by oxidation of suitable heteroaryl-thiols HS—Ar or heteroaryl-benzyl-thioethers C$_6$H$_5$—CH$_2$—S—Ar with chlorine (Synthesis, 1998, 36-38; J. Am. Chem. Soc., 1950, 74, 4890-92;) directly to the corresponding sulfonyl chlorides. The further are known in the art or may be prepared by standard methods. E.g. mercapto-pyrimidines or pyrimidinyl-benzylthioether precursors can e.g. be prepared according to literature (Chemische Berichte, 1960, 1208-11; Chemische Berichte, 1960, 95, 230-235; Collection Czechoslow. Chem. Comm., 1959, 24, 1667-1671; Austr. J. Chem., 1966, 19, 2321-30; Chemiker-Zeitung, 101, 6, 1977, 305-7; Tetrahedron, 2002, 58, 887-890; Synthesis, 1983, 641-645).

In the following schemes 3 to 5 several routes are shown which are suitable to prepare benzenesulfonyl chlorides carrying a fluorinated propyl radical.

The 4-(1,1-difluoropropan-2-yl)benzene-1-sulfonyl chloride intermediate can be prepared from the commercially available 2-phenylpropanoic acid. In the first step a) the 2-phenylpropanic acid is converted to the alkyl ester by esterification with an alcohol (e.g. methanol or ethanol) under acid catalysis (e.g. HCl, SO$_2$Cl$_2$). The ester can be reduced to the corresponding 2-phenyl propanal by a reducing agent such as DIBAL (diisobutylaluminium hydride). The aldehyde is converted to the 1,1-difluoro-2-propyl derivative by reaction with a suitable fluorinating reagent like DAST (diethylaminosulfurtrifluoride), morpholine-DAST, deoxofluor (bis(2-methoxyethyl)aminosulfur trifluoride), Ishikawa's reagent (N,N-diethyl-(1,1,2,3,3,3-hexafluoropropyl)amine: Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 3 can also be performed using (R)-2-phenylpropanic acid and (S)-2-phenylpropanic acid respectively to give the corresponding chiral 4-(1,1-difluoropropan-2-yl)benzene-1-sulfonyl chlorides.

Scheme 4:

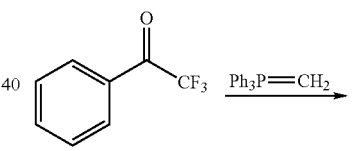

Scheme 3:

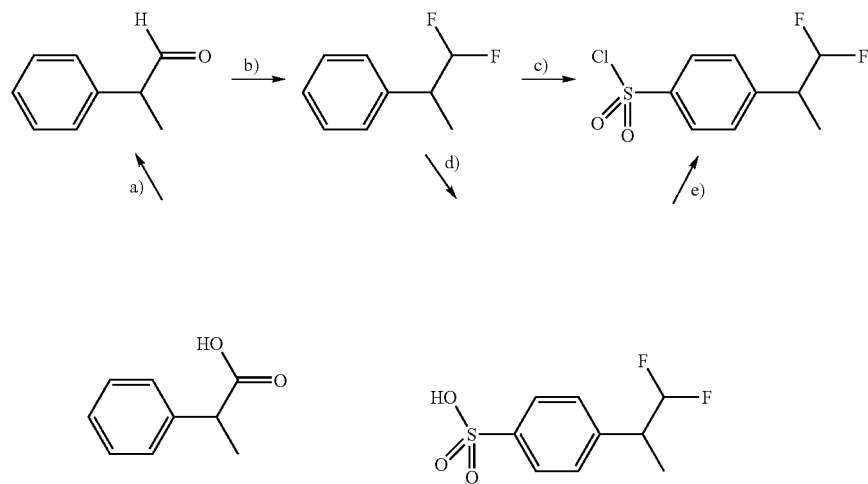

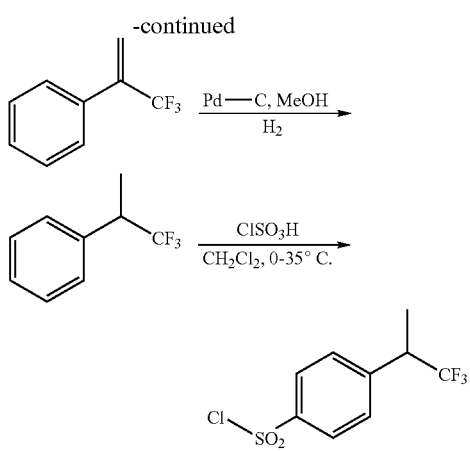

4-(1,1,1-Trifluoropropan-2-yl)benzene-1-sulfonyl chloride intermediate can be prepared from the commercially available 2,2,2-trifluoro-1-phenylethanone by a synthetic route shown in scheme 4. The ketone can be converted to the 3,3,3-trifluoro-2-phenylpropene by a Wittig reaction with a suitable ylide such as methylene-triphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable base such as lithium diisopropylamide or potassium tert-butoxide. The thus obtained 3,3,3-trifluoro-2-phenylpropene can then be reduced to the saturated alkane by catalytic hydrogenation (eg Pd—C) followed by conversion to the sulfonyl chloride by the methods described in scheme 3.

The synthesis of scheme 4 can also be performed using a chiral catalyst for the alkene hydrogenation to allow the preparation of the corresponding chiral 4-(1,1,1-triifluoropropan-2-yl)benzene-1-sulfonyl chlorides.

Scheme 5:

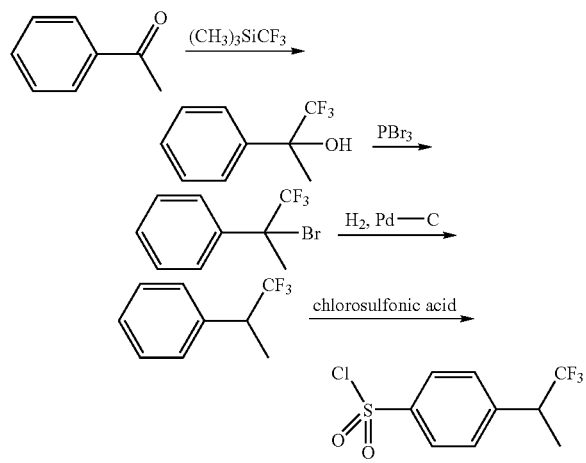

The 4-(1,1,1-trifluoropropan-2-yl)benzene-1-sulfonyl chloride can be also prepared from the commercially available 1-phenyl-ethanone by a four step procedure as shown in scheme 5. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (eg Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_1$ receptors, $D_4$ receptors, $\alpha$1-adrenergic and/or $\alpha$2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in-vitro receptor binding constants ($K_i(D_3)$ values) of as a rule less than 50 nM (nmol/l), preferably of less than 10 nM and, in particular of less than 5 nM. The displacement of [$^{125}$I]-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of [$^3$H]SCH23390,

[$^{125}$I]-iodosulpride or [$^{125}$I]-spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847) and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

The compounds were either characterized via proton-NMR in $d_4$-methanol, $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Preparation of Intermediates a. Synthesis of Sulfonyl Chlorides a. 1 4-((S)-2-Fluoro-1-methyl-ethyl)-benzenesulfonyl chloride a.1.1 Toluene-4-sulfonic acid (S)-2-phenyl-propyl ester To a solution of 20 g of (S)-(−)-2-phenyl-1-propanol in 240 ml of dichloromethane was added in portions 28 g of p-toluenesulfonyl chloride (146.8 mmol). After stirring for 18 h at room temperature, the organic phase was washed with 100 ml of water, dried over magnesium sulfate, filtered, and the solvent evaporated under reduced pressure to yield 43 g of the title compound.

$^1$H-NMR (CDCl$_3$, 400 MHz): δ [ppm] 7.65 (d, 2H), 7.15-7.3 (m, 5H), 7.1 (d, 2H), 4.0-4.1 (m, 2H), 3.1 (m, 1H), 2.4 (s, 3H), 1.3 (d, 3H).

a.1.2 ((S)-2-Fluoro-1-methyl-ethyl)-benzene 9.62 g of toluene-4-sulfonic acid (S)-2-phenyl-propyl ester (33.13 mmol) were dissolved in 80 ml of polyethylenglycol 400. 9.62 g of potassium fluoride (165.6 mmol) were added and the reaction mixture was stirred at 50° C. for 3 days and another 2 days at 55-70° C. The reaction was treated with 150 ml of saturated aqueous sodium chloride solution, extracted three times with diethyl ether, and the combined organic layers were dried over magnesium sulfate, filtered, and the solvent was evaporated under reduced pressure. The crude product was purified via silica gel chromatography using cyclohexyane/ethyl acetate 15% as eluent. 2.85 g of the desired product were isolated, containing ~25% of the elimination side product.

¹H-NMR (CDCl₃, 400 MHz): δ [ppm] 7.2-7.4 (m, 5H), 4.3-4.6 (several m, 2H), 3.15 (m, 1H). 1.3 (m, 3H).

a.1.3 4-((S)-2-Fluoro-1-methyl-ethyl)-benzenesulfonyl chloride 3.5 g of ((S)-2-fluoro-1-methyl-ethyl)-benzene (25.32 mmol) were dissolved in 80 ml of dichloromethane. At 0-5° C., 11.81 g of chlorosulfonic acid (101.31 mmol), dissolved in 20 ml of dichloromethane, were added dropwise. The reaction mixture was stirred for 30 min at room temperature and 2 h at 30° C. The solvent was evaporated. 150 ml of diethyl ether were added to the residue, washed once with 150 ml of water, and the organic layer was dried over magnesium sulfate, filtered, and the solvent evaporated under reduced pressure. The crude product was purified via silica gel chromatography with n-heptane-dichloromethane (6:4) as eluent to give 1.5 g of the title compound.
¹H-NMR (CDCl₃, 400 MHz): δ [ppm] 8.0 (d, 2H), 7.5 (d, 2H), 4.5 (dd, 2H), 3.25 (m, 1H), 1.4 (d, 3H).

a.2 4-((R)-2-Fluoro-1-methyl-ethyl)-benzenesulfonyl chloride a.2.1 Toluene-4-sulfonic acid (R)-2-phenyl-propyl ester

Following the procedure analogous to that used for the synthesis of toluene-4-sulfonic acid (S)-2-phenyl-propyl ester, but using (R)-2-phenyl-1-propanol, the title compound was prepared a.2.2 ((R)-2-Fluoro-1-methyl-ethyl)-benzene

The title compound was prepared as described above for the synthesis of ((S)-2-fluoro-1-methyl-ethyl)-benzene, but using toluene-4-sulfonic acid (R)-2-phenyl-propyl ester instead of toluene-4-sulfonic acid (S)-2-phenyl-propyl ester.
¹H-NMR (CDCl₃, 400 MHz): δ [ppm] 7.2-7.4 (m, 5H), 4.3-4.6 (several m, 2H), 3.15 (m, 1H). 1.3 (m, 3H).

a.2.3 4-((R)-2-Fluoro-1-methyl-ethyl)-benzenesulfonyl chloride 1.3 g of ((R)-2-fluoro-1-methyl-ethyl)-benzene (9.4 mmol) were dissolved in 50 ml of dichloromethane. At 0-5° C., 1.1 g of chlorosulfonic acid (9.4 mmol), dissolved in 10 ml of dichloromethane, were added dropwise. The reaction mixture was stirred for 20 min at 0-5° C. and then added to a solution of 2.15 g of phosphorous pentachloride dissolved in 40 ml of dichloromethane. The reaction mixture was stirred for 30 min at 0-5° C. and 1 h at room temperature. The solvent was evaporated, 100 ml of diethyl ether were added, the mixture was washed once with 150 ml of water, and the organic layer dried over magnesium sulfate, filtered, and the solvent evaporated under reduced pressure. The crude product was purified via silica gel chromatography with n-heptane-dichloromethane (1:1) as eluent to give 0.261 g of the title compound.
¹H-NMR (CDCl₃, 400 MHz): δ [ppm] 8.0 (d, 2H), 7.5 (d, 2H), 4.5 (dd, 2H), 3.25 (m, 1H), 1.4 (d, 3H).

a.3 4-(2-Fluoro-1-methyl-ethyl)-benzenesulfonyl chloride

Following the procedures analogous to that used for the preparation of 4-((S)-2-fluoro-1-methyl-ethyl)-benzenesulfonyl chloride, but starting with 2-phenyl-1-propanol in step a.3.1, the title compound was prepared.
¹H-NMR (CDCl₃, 400 MHz): δ [ppm] 8.0 (d, 2H), 7.5 (d, 2H), 4.5 (dd, 2H), 3.25 (m, 1H), 1.4 (d, 3H).

a.4 4-(2-Fluoro-1-fluoromethyl-ethyl)-benzenesulfonyl chloride a.4.1 (2-Fluoro-1-fluoromethyl-ethyl)-benzene 4 g of 3-phenylglutaric acid (19.21 mmol) were suspended in 350 ml of dichloromethane. At room temperature, 6.5 g of xenon difluoride (38.42 mmol) were added and the reaction mixture was stirred at room temperature for 18 h. The organic phase was washed once with 975 ml of 6% aqueous sodium hydrogencarbonate, dried over magnesium sulfate, filtered, and the solvent evaporated. The remaining residue was distilled at a bath temperature of 123° C. at 21 mm to yield 0.78 g of the title compound that contained ~50% of 4-(2-Fluoro-1-methyl-ethyl)-benzene.
¹H-NMR (CDCl₃, 400 MHz): δ [ppm] 7.2-7.4 (m, 5H), 4.6-4.8 (dd, 4H), 3.3 (m, 1H).

a.4.2 4-(2-Fluoro-1-fluoromethyl-ethyl)-benzenesulfonyl chloride

Following the procedures analogous to that used for the preparation of 4-((S)-2-fluoro-1-methyl-ethyl)-benzenesulfonyl chloride, but using 5 equivalents of chlorosulfonic acid, 0.12 g of the title compound were obtained.
¹H-NMR (CDCl₃, 400 MHz): δ [ppm] 8.05 (d, 2H), 7.55 (d, 2H), 4.75 (dd, 4H), 3.4 (m, 1H).

a. 5 4-(3,3,3-Trifluoropropyl)-benzenesulfonyl chloride 2.9 g were obtained from commercially available (3,3,3-trifluoropropyl)-benzene following the procedure used for the synthesis of 4-((S)-2-fluoro-1-methyl-ethyl)-benzenesulfonyl chloride described above.
¹H-NMR (CDCl₃, 400 MHz): δ [ppm] 8.0 (d, 2H), 7.45 (d, 2H), 3.0 (t, 2H), 2.45 (m, 2H).

a.6 4-(2,2,2-Trifluoroethyl)-benzenesulfonyl chloride

The product was obtained from commercially available (2,2,2-trifluoroethyl)-benzene following the procedure as described in J. Org. Chem., 1960, 25, 1824-26.
¹H-NMR (CDCl₃, 400 MHz): δ [ppm] 8.05 (d, 2H), 7.55 (d, 2H), 3.5 (q, 2H).

a.7 4-(3-Fluoropropyl)-benzenesulfonyl chloride a.7.1 (3-Fluoropropyl)-benzene 15.6 g of diethylaminosulfurtrifluoride (DAST, 96.91 mmol) were dissolved in 18 ml of dichloromethane. At 0-5° C., 12 g of 3-phenyl-1-propanol (88.1 mmol) dissolved in 30 ml of dichloromethane, were added dropwise. The reaction mixture was stirred for 18 h, and, after addition of 30 ml of dichloromethane, poured onto 100 ml of ice water. The organic layer was separated, dried over magnesium sulfate, filtered, and the solvent evaporated. The crude product was purified by distillation at a bath temperature of 106° C. at 20 mm to yield 7.4 g of the title compound.

¹H-NMR (CDCl₃, 400 MHz): δ [ppm] 7.1-7.3 (m, 5H), 4.4 (dt, 2H), 2.7 (m, 2H). 2.0 (m, 2H).

a.7.2 4-(3-Fluoropropyl)-benzenesulfonyl chloride 4.1 g of (3-fluoro-propyl)-benzene (29.67 mmol) were dissolved in 40 ml of dichloromethane. At 0-5° C., 6.91 g of chlorosulfonic acid (59.34 mmol), dissolved in 10 ml of dichloromethane, were added dropwise. The reaction mixture was stirred for 45 min at 0-5° C. and then added to a solution of 6.8 g of phosphorous pentachloride (32.63 mmol) dissolved in 50 ml of dichloromethane. The reaction mixture was stirred for 1 h at 5-10° C. The solvent was evaporated, 150 ml of diethyl ether added, washed once with 150 ml of ice water, and the organic layer dried over magnesium sulfate, filtered, and the solvent evaporated under reduced pressure. The crude product was purified via silica gel chromatography with n-heptane-dichloromethane (11:9) as eluent to give 5.5 g of the title compound.
¹H-NMR (CDCl₃, 400 MHz): δ [ppm] 7.95 (d, 2H), 7.45 (d, 2H), 4.5 (dt, 2H), 2.9 (t, 2H), 2.05 (m, 2H).

a.8 4-(2,2-Difluoro-cyclopropyl)-benzenesulfonyl chloride 2.07 g of were obtained from commercially available (2,2-difluorocyclopropyl)-benzene following the procedure used for the synthesis of (3-fluoropropyl)-benzenesulfonyl chloride with the exception that only 1.1 equivalents of phosphorous pentachloride were used.
¹H-NMR (CDCl₃, 400 MHz): δ [ppm] 8.0 (d, 2H), 7.45 (d, 2H), 2.85 (m, 1H), 2.0 (m, 1H), 1.75 (m, 1H).

a.9 3-Bromo-4-trifluoromethoxy-benzenesulfonyl chloride 2.0 g of 1-bromo-2-(trifluoro-methoxy)benzene (8.3 mmol) were dissolved in 30 ml of dichloromethane. At 0-5° C., 1.06 g of chlorosulfonic acid (9.13 mmol), dissolved in 3 ml of dichloromethane, were added dropwise. The reaction mixture was stirred for 30 min at room temperature. Additional 5.5 equivalents of chlorosulfonic in dichloromethane were added to drive the reaction to completion. Standard work-up was followed and silica gel chromatography with n-heptane-dichloromethane (6:4) as eluent gave 2.19 g of the title compound.
¹H-NMR (CDCl₃, 400 MHz): δ [ppm] 8.3 (d, 1H), 8.05 (dd, 1H), 7.5 (dd, 1H).

a.10 4-(2-Fluoroethyl)-benzenesulfonyl chloride a.10.1 (2-Fluoroethyl)-benzene 6.8 g of the title compound were obtained from commercially available 2-phenylethanol following the procedure used for the synthesis of (3-fluoropropyl)-benzene.
¹H-NMR (CDCl₃, 400 MHz): δ [ppm] 7.1-7.3 (m, 5H), 4.6 (m, 1H), 4.45 (m, 1H), 2.95 (m, 1H), 2.9 (m, 1H).

a.10.2 4-(2-Fluoroethyl)-benzenesulfonyl chloride 3.55 g were obtained following the procedure used for the synthesis of 4-((R)-2-fluoro-1-methyl-ethyl)-benzenesulfonyl chloride.
¹H-NMR (CDCl₃, 400 MHz): δ [ppm] 8.0 (d, 2H), 7.5 (d, 2H), 4.7 (dt, 2H), 3.05-3.2 (dt, 2H).

a.11 5-Propylthiophene-2-sulfonyl chloride

Following the procedures analogous to that used for the preparation of (3-fluoropropyl)-benzenesulfonyl chloride, but using only 1 equivalent of phosphorous pentachloride, the title compound was prepared.
¹H-NMR (CDCl₃, 400 MHz): δ [ppm] 7.7 (d, 1H), 6.85 (d, 1H), 2.9 (t, 2H), 1.75 (m, 2H), 1.0 (t, 3H).

a.12 4-(1-Methyl-1H-pyrazol-4-yl)-benzenesulfonyl chloride a.12.1 1-Methyl-4-phenyl-1H-pyrazole 1 g of 2-phenylmalonaldehyde (6.75 mmol) were dissolved in 25 ml of ethanol. 0.36 ml of N-methyl-hydrazine (6.75 mmol) were added, the reaction mixture was stirred under reflux for 4 h, the solvent evaporated under reduced pressure to yield 1.09 g of the product.
ESI-MS: 159.1 [M+H]+
¹H-NMR (CDCl₃, 400 MHz): δ [ppm] 7.75 (s, 1H), 7.6 (s, 1H), 7.45 (d, 2H), 7.35 (t, 2H), 7.2 (t, 1H), 3.9 (s, 3H)

a.12.2 4-(1-Methyl-1H-pyrazol-4-yl)-benzenesulfonyl chloride 0.5 g of 1-methyl-4-phenyl-1H-pyrazole (3.16 mmol) were dissolved in 20 ml of dichloromethane. At 0° C., 0.232 ml of chlorosulfonic acid were added and the reaction mixture was stirred for 1 h under ice cooling. Additional 0.7 ml of chlorosulfonic acid were added, the mixture was stirred at 0° C. for 30 minutes and then 90 minutes at 50° C. The two phases were separated and the lower layer put on ice, extracted twice with diethyl ether, dried over magnesium sulfate, filtered, and the solvent evaporated under reduced pressure to yield 0.496 g of the product.
¹H-NMR (CDCl₃, 400 MHz): δ [ppm] 8.0 (d, 2H), 7.85 (s, 1H), 7.75 (s, 1H), 7.65 (d, 2H), 4.0 (s, 3H).

a.13 4-(1,1,1-Trifluoropropan-2-yl)benzenesulfonyl chloride and 2-(1,1,1-trifluoropropan-2-yl)benzenesulfonyl chloride Prepared on a 14 g scale following the procedure outlined in Scheme 7. 2-(1,1,1-Trifluoropropan-2-yl)benzenesulfonyl chloride is a by-product of the reaction.
4-(1,1,1-Trifluoropropan-2-yl)benzenesulfonyl chloride:
MS (ESI) m/z: 273.1 [M+H]⁺
¹H-NMR (DMSO-d₆): δ [ppm] 7.62 (d, 2H), 7.33 (d, 2H), 3.81 (m, 1H), 1.42 (d, 3H).
2-(1,1,1-Trifluoropropan-2-yl)benzenesulfonyl chloride:
MS (ESI) m/z: 273.1 [M+H]⁺ a.14 4-(1,1-Difluoropropan-2-yl)benzenesulfonyl chloride and 2-(1,1-Difluoropropan-2-yl)benzene-1-sulfonyl chloride Prepared on an 11 g scale following the procedure outlined in Scheme 6. 2-(1,1-Difluoropropan-2-yl)benzene-1-sulfonyl chloride is a by-product of the reaction.
4-(1,1-Difluoropropan-2-yl)benzenesulfonyl chloride:
MS (ESI) m/z: 255.0 [M+H]⁺
¹H-NMR (DMSO): δ [ppm] 8.03 (d, 2H), 7.55 (d, 2H), 5.88 (dt, 1H), 3.34 (m, 1H), 1.47 (d, 3H).
¹³C-NMR (DMSO-d₆): δ [ppm] 146.43, 143.54, 129.77, 127.28, 117.06 (t), 43.76, 13.78.

2-(1,1-Difluoropropan-2-yl)benzene-1-sulfonyl chloride:
Isolated by chromatography on 110 mg scale.

MS (ESI) m/z: 255.0 [M+H]$^+$ $^1$H-NMR (DMSO-d$_6$): δ [ppm] 8.15 (d, 1H), 7.77 (t, 1H), 7.70 (d, 1H), 7.54 (t, 1H), 5.99 (dt, 1H), 4.43 (m, 1H), 1.51 (d, 3H).

$^{13}$C-NMR (DMSO-d$_6$): δ [ppm] 143.45, 138.63, 135.53, 130.93, 129.04, 128.17, 116.61 (t), 38.38, 13.68.

b. Preparation of toluene-4-sulfonic acid 3-fluoro-propyl ester 5 g of 3-fluoro-propanol (64.03 mmol) and 18 ml of triethylamine (129.32 mmol) were dissolved in 50 ml dichloromethane. At 0-5° C., 12.9 g toluene-4-sulfonylchloride (67.66 mmol) were added and the reaction mixture stirred at room temperature for 18 h. Standard work-up yielded 13.7 g of toluene-4-sulfonic acid 3-fluoro-propyl ester.

ESI-MS: 233.1 [M+H]$^+$

II. Preparation of Compounds I

Example 1

4-Isopropyl-N-[4-((1R,5S,6R)-3-propyl-3-aza-bicyclo[3.2.0]hept-6-yl)-phenyl]-benzenesulfonamide 1.1
(1R,5S,6R)-6-Phenyl-3-aza-bicyclo[3.2.0]heptane 11.1 g of (1R,5S,6R)-6-phenyl-3-aza-bicyclo[3.2.0]heptane×0.5 ditoloyl tartrate were dissolved in 50 ml of 1 N aqueous sodium hydroxide. The aqueous layer was extracted three times with diethyl ether, the combined organic phases dried over magnesium sulfate, filtered, and evaporated to dryness to yield 5.15 g of the free amine.

$^1$H-NMR (CDCl$_3$): δ [ppm] 7.15-7.4 (several m, 5H), 3.0 (m, 2H), 2.7-2.9 (several m, 4H), 2.3 (m, 1H), 2.1 (m, 1H), 2.0 (m, 1H).

1.2 1-((1R,5S,6R)-6-Phenyl-3-aza-bicyclo[3.2.0]hept-3-yl)-propan-1-one 2.82 g of (1R,5S,6R)-6-phenyl-3-aza-bicyclo[3.2.0]heptane (16.28 mmol) were dissolved in 45 ml of tetrahydrofuran and 4.53 ml of triethylamine were added (32.55 mmol). At −5° C., a solution of 2.33 g of propionic acid anhydride (17.9 mmol) in 5 ml of tetrahydrofuran was added dropwise. After stirring for 2 h at room temperature, the reaction mixture was treated with 3 ml of 7 N ammonia in methanol, stirred for 10 minutes, and the solvents were evaporated. The residue was redissolved in ethyl acetate and washed with water and saturated aqueous sodium chloride. The organic layer was dried over magnesium sulfate, filtered, and the solvent was evaporated under reduced pressure. The residue was redissolved in 70 ml of diethyl ether, washed twice with water and once with saturated aqueous sodium hydrogen carbonate. The organic phase was again dried over magnesium sulfate, filtered, and the solvent evaporated under reduced pressure to yield 3.64 g of the product.

ESI-MS: 230.1 [M+H]$^+$ $^1$H-NMR (CDCl$_3$): δ [ppm] 7.15-7.4 (several m, 5H), 4.0 (dd, 1H), 3.6 (m, 2H), 3.2-3.45 (several m, 2H), 2.9-3.1 (m, 2H), 2.25-2.5 (m, 3H), 2.15 (m, 1H), 1.2 (m, 3H).

1.3 1-[(1R,5S,6R)-6-(4-Nitro-phenyl)-3-aza-bicyclo[3.2.0]hept-3-yl]-propan-1-one 1.0 g of 1-((1R,5S,6R)-6-Phenyl-3-aza-bicyclo[3.2.0]hept-3-yl)-propan-1-one (4.36 mmol) were dissolved in 12 ml of nitromethane. At −8° C., a mixture of 0.3 ml of nitric acid (65%, 4.36 mmol) and 4.6 ml of sulphuric acid (95%) in 0.76 ml of water were added dropwise within 45 minutes. Stirring at −8° C. was continued for 30 minutes, before 20 ml of ice water were added and the aqueous phase was extracted twice with diethyl ether, the combined organic layers were dried over magnesium sulfate, filtered, and the solvent was evaporated under reduced pressure to yield 1.27 g of the product as a mixture of 2:1 para versus ortho substituted product which was used without further separation.

ESI-MS: 275.1 [M+H]$^+$ 1.4 1-[(1R,5S,6R)-6-(4-Amino-phenyl)-3-aza-bicyclo[3.2.0]hept-3-yl]-propan-1-one 1.21 g of 1-((1R,5S,6R)-6-(4-nitro-phenyl)-3-aza-bicyclo[3.2.0]hept-3-yl)-propan-1-one (4.44 mmol) were dissolved in 50 ml of methanol, 8.0 g of stannous dichloride SnCl$_2$×H$_2$O (35.46 mmol) were added, and the reaction was stirred under refluxing conditions for 2 h. The solvent was evaporated and the residue portioned between 1 N aqueous sodium hydroxide and ethyl acetate. This mixture was filtered, the two phases were separated, and the aqueous layer was extracted with ethyl acetate and dichloromethane. The combined organic phases were dried over magnesium sulfate, filtered, and the solvent was evaporated under reduced pressure to yield 0.94 g of the product as a mixture of 72% para and 28% ortho substituted product which was used in the next step without further separation.

ESI-MS: 245.1 [M+H]$^+$ 1.5 4-Isopropyl-N-[4-((1R,5S,6R)-3-propionyl-3-aza-bicyclo[3.2.0]hept-6-yl)-phenyl]-benzenesulfonamide 0.935 g of 1-((1R,5S,6R)-6-(4-amino-phenyl)-3-aza-bicyclo[3.2.0]hept-3-yl)-propan-1-one (3.83 mmol) were dissolved in 30 ml of tetrahydrofuran and 0.795 g of 4-isopropylbenzenesulfonyl chloride (3.64 mmol) and 1.6 ml of triethylamine (11.48 mmol) were added. After stirring for 18 h at room temperature, the solvent was evaporated under reduced pressure, the remaining material was partitioned between diethyl ether and water that was adjusted to alkaline pH with 1 N aqueous sodium hydroxide. The aqueous layer was reextracted three times with diethyl ether, and the combined organic layers were dried over magnesium sulfate, filtered, and the solvent was evaporated to yield 1.76 g of crude product that was used in the subsequent reaction step without further purification.

ESI-MS: 427.1 [M+H]$^+$ 1.6 4-Isopropyl-N-[4-((1R,5S,6R)-3-propyl-3-azabicyclo[3.2.0]hept-6-yl)-phenyl]-benzenesulfonamide 0.9 g of 4-isopropyl-N-[4-((1R,5S,6R)-3-propionyl-3-azabicyclo[3.2.0]hept-6-yl)-phenyl]-benzenesulfonamide (2.11 mmol) were dissolved in tetrahydrofuran and 11 ml of a 1 M borane/THF complex in tetrahydrofuran (10.8 mmol) was added at room temperature. The reaction mixture was heated under reflux for 30 minutes, 10 ml of aqueous 2 N hydrochloric acid were added, and the mixture was again refluxed for 3 h. After cooling to room temperature, the solvent was evaporated, the residue was treated with 50% aqueous sodium hydroxide solution, and the aqueous layer was extracted twice with diethyl ether. The combined organic layers were dried over magnesium sulfate, filtered, and the solvent was evaporated to yield 0.824 g of crude product which was then purified via preparative HPLC (column Delta Pak, 40 mm diameter, methanol/water/0.1% acetic acid) to yield 0.078 g of the purified product.

ESI-MS: 413.3 [M+H]$^+$ $^1$H-NMR (DMSO-d$_6$): δ [ppm] 10.2 (s, broad, 1H), 7.7 (d, 2H), 7.4 (d, 2H), 7.1 (d, 2H), 7.0 (d, 2H), 3.1 (m, 1H), 2.8-3.0 (m, 3H), 2.7 (m, 1H), 2.6 (m, 1H), 2.4 (m, 2H), 1.9-2.1 (m, 4H), 1.5 (m, 2H), 1.15 (m, 6H), 0.9 (m, 3H).

Example 2

4-isopropyl-N-[4-(exo-3-propionyl-3-aza-bicyclo[3.2.0]hept-6-yl)-phenyl]-benzenesulfonamide and 4-isopropyl-N-[2-(exo-3-propionyl-3-aza-bicyclo[3.2.0]hept-6-yl)-phenyl]-benzenesulfonamide 2.1 exo-1-[6-(4-Nitro-phenyl)-3-aza-bicyclo[3.2.0]hept-3-yl]-propan-1-one and exo-1-[6-(2-nitro-phenyl)-3-aza-bicyclo[3.2.0]hept-3-yl]-propan-1-one 2.86 g of exo-1-[6-(4-Nitro-phenyl)-3-aza-bicyclo[3.2.0]hept-3-yl]-propan-1-one and exo-1-[6-(2-nitro-phenyl)-3-aza-bicyclo[3.2.0]hept-3-yl]-propan-1-one were prepared according to synthetic procedures as described for 1-[(1R,5S,6R)-6-(4-nitro-phenyl)-3-azabicyclo[3.2.0]hept-3-yl]-propan-1-one.

ESI-MS: 275.1 [M+H]$^+$ 2.2 exo-1-[6-(4-Amino-phenyl)-3-aza-bicyclo[3.2.0]hept-3-yl]-propan-1-one and exo-1-[6-(2-amino-phenyl)-3-aza-bicyclo[3.2.0]hept-3-yl]-propan-1-one 2.8 g of the product obtained in 2.1 (10.2 mmol) were dissolved in 40 ml of methanol, 4 ml of acetic acid was added, and, under nitrogen atmosphere, 0.4 g of 10% Pd/C. Hydrogenation continued until the starting material was consumed. The catalyst was filtered and the filtrate evaporated to dryness to yield 3.2 g of the amino compound, again as a 2:1 mixture of the para and ortho isomers which was used in the next step, without further separation.

ESI-MS: 245.15 [M+H]$^+$ 2.3 4-Isopropyl-N-[4-(exo-3-propionyl-3-aza-bicyclo[3.2.0]hept-6-yl)-phenyl]-benzenesulfonamide and 4-isopropyl-N-[2-(exo-3-propionyl-3-aza-bicyclo[3.2.0]hept-6-yl)-phenyl]-benzenesulfonamide To a solution of 3.2 g of the product obtained in 2.2 (13.1 mmol) in 40 ml of pyridine at 0° C. were added dropwise 3.15 g of 4-isopropylbenzenesulfonyl chloride in 5 ml of dichloromethane. Stirring was continued for 3 h before the solvents were evaporated and the residue was partitioned between 80 ml of ethyl acetate and 60 ml of water. The aqueous phase was extracted again with ethyl acetate, and the combined organic phases were dried over magnesium sulfate, filtered, and evaporated to dryness to yield 3.9 g of the product as a 2:1 mixture of the para and ortho isomers which was used in example 3 without further separation.

ESI-MS: 427.2 [M+H]$^+$

Example 3

4-Isopropyl-N-[4-(exo-3-propyl-3-aza-bicyclo[3.2.0]hept-6-yl)-phenyl]-benzenesulfonamide 0.151 g of the product were obtained using the same synthetic procedures as for the 4-isopropyl-N-[4-((1R,5S,6R)-3-propyl-3-aza-bicyclo[3.2.0]hept-6-yl)-phenyl]-benzenesulfonamide as described in example 1.6. The crude product was thereby purified via preparative HPLC using a DeltaPak column (40 mm I.D., methanol/water/0.1% acetic acid) to give 0.151 g of the title compound and 0.04 mg of the corresponding ortho-substituted product.

4-Isopropyl-N-[4-(exo-3-propyl-3-aza-bicyclo[3.2.0]hept-6-yl)-phenyl]-benzenesulfonamide

ESI-MS: 413.1 [M+H]$^+$ $^1$H-NMR (DMSO-d$_6$): δ [ppm] 10.15 (s, broad, 1H), 7.7 (d, 2H), 7.4 (d, 2H), 7.1 (d, 2H), 7.0 (d, 2H), 3.1 (m, 1H), 2.8-3.0 (m, 3H), 2.7 (m, 1H), 2.6 (m, 1H), 2.4 (m, 2H), 1.9-2.1 (m, 4H), 1.5 (m, 2H), 1.15 (m, 6H), 0.9 (m, 3H).

4-isopropyl-N-[2-(exo-3-propyl-3-aza-bicyclo[3.2.0]hept-6-yl)-phenyl]-benzenesulfonamide

ESI-MS: 413.2 [M+H]$^+$

Example 4

N-[4-((1R,5S,6R)-3-Propyl-3-aza-bicyclo[3.2.0]hept-6-yl)-phenyl]-4-trifluoromethoxy-benzenesulfonamide Step 1. Following a procedure analogous to the procedure described in example 1.5, but starting with 1-[(1R,5S,6R)-6-(4-aminophenyl)-3-aza-bicyclo[3.2.0]hept-3-yl]-propan-1-one and 4-trifluoromethoxybenzensulfonyl chloride, N-[4-((1R,5S,6R)-3-propionyl-3-azabicyclo[3.2.0]hept-6-yl)-phenyl]-4-trifluoromethoxy-benzenesulfonamide (234 mg, yield 86%) was obtained.

Step 2. Following a procedure analogous to the procedure described in example 1.6, N-[4-((1R,5S,6R)-3-propionyl-3-aza-bicyclo[3.2.0]hept-3-yl]-propan-1-one was reduced to yield the title compound (37 mg, yield: 38%).

MS (ESI) m/z: 455.0 [M+H]$^+$ $^1$H-NMR (DMSO-d$_6$): δ [ppm] 7.83 (d, 2H), 7.52 (d, 2H), 7.12 (d, 2H), 7.02 (d, 2H), 3.11 (m, 1H), 2.91 (m, 2H), 2.73 (m, 1H), 2.62 (m, 1H), 2.40 (m, 3H), 2.01 (m, 2H), 1.55 (m, 2H), 0.92 (t, J=7.3 Hz, 3H).

Example 5

N-[4-((1R,5S,6R)-3-Propyl-3-aza-bicyclo[3.2.0]hept-6-yl)-phenyl]-4-trifluoromethyl-benzenesulfonamide Step 1. Following a procedure analogous to the procedure described in example 1.5, the sulfonamide was prepared (389 mg, yield 98%).

Step 2. Following a procedure analogous to the procedure described in example 1.6, the amide was reduced to yield the title compound (amount 76 mg; yield 39%).

MS (ESI) m/z: 439.1 [M+H]$^+$

¹H-NMR (DMSO-d₆): δ [ppm] 10.32 (br s, 1H), 7.92 (m, 4H), 7.14 (d, 2H), 7.02 (d, 2H), 3.11 (m, 1H), 2.89 (m, 2H), 2.73 (m, 1H), 2.62 (m, 1H), 2.40 (m, 3H), 2.01 (m, 2H), 1.55 (m, 2H), 0.92 (t, J=7.3 Hz, 3H).

Example 6

N-[4-((1R,5S,6R)-3-Allyl-3-aza-bicyclo[3.2.0]hept-6-yl)-phenyl]-4-trifluoromethoxy-benzenesulfonamide Step 1: N-[4-((1R,5S,6R)-3-Propionyl-3-aza-bicyclo[3.2.0]hept-6-yl)-phenyl]-4-trifluoromethoxy-benzenesulfonamide (100 mg, 0.21 mmol) was dissolved in n-butanol (10 ml) followed by the addition of concentrated HCl (2 ml). The solution was refluxed for 3 hours, cooled and concentrated. The residue was washed with ethyl acetate, treated with NaOH (2M) and extracted with ethyl acetate (3×10 ml). The alkaline organic extracts were dried over MgSO₄, filtered and concentrated to give N-[4-(3-aza-bicyclo[3.2.0]hept-6-yl)-phenyl]-4-trifluoromethoxy-benzenesulfonamide as an oil (amount 389 mg, yield 98%).

Step 2. 100 mg (0.43 mmol) of N-[4-(3-aza-bicyclo[3.2.0]hept-6-yl)-phenyl]-4-trifluoromethoxy-benzenesulfonamide and 40 μl (0.46 mmol) of allyl bromide were dissolved in 2 ml of N,N-dimethylformamide. 0.18 ml (1.26 mmol) of triethylamine were then added to the solution. After the mixture had been stirred at room temperature for 1 hour, a further 10 μl of allyl bromide were added to the reaction mixture, which was then stirred overnight at room temperature. After the solvent had been evaporated down to dryness, the resulting residue was taken up in water and this solution was made alkaline using a 1N aqueous solution of sodium hydroxide. After that, the aqueous reaction mixture was extracted three times with diethyl ether. The combined organic phases were dried over sodium sulfate, filtered and evaporated down give 50 mg of title compound (yield 46%).

MS (ESI) m/z: 453.0 [M+H]⁺

¹H-NMR (DMSO-d₆): δ [ppm] 10.25 (br s, 1H), 7.82 (d, 2H), 7.52 (d, 2H), 7.12 (d, 2H), 7.01 (d, 2H), 5.92 (m, 1H), 5.20 (d, 1H), 5.11 (d, 1H), 3.15 (m, 3H), 2.80 (m, 2H), 2.71 (m, 1H), 2.62 (m, 1H), 2.00 (m, 4H).

Example 7

4-Bromo-N-[4-((1R,5S,6R)-3-propyl-3-aza-bicyclo[3.2.0]hept-6-yl)-phenyl]-benzenesulfonamide Step 1: Following a procedure in analogy to the procedure described in example 1.6, borane reduction of 1-[(1R,5S,6R)-6-(4-amino-phenyl)-3-aza-bicyclo[3.2.0]hept-3-yl]-propan-1-one gave the propyl compound.

Step 2: Following a procedure analogous to the procedure described in example 1.5, 164 mg of the title compound (yield 42%) were obtained.

MS (ESI) m/z: 449.0, 451.0 [M+H]⁺

¹H-NMR (DMSO-d₆): δ [ppm] 10.18 (br s, 1H), 7.75 (d, 2H), 7.64 (d, 2H), 7.13 (d, 2H), 7.00 (d, 2H), 3.11 (m, 1H), 2.91 (m, 2H), 2.73 (m, 1H), 2.62 (m, 1H), 2.40 (m, 3H), 2.01 (m, 2H), 1.52 (m, 2H), 0.92 (t, J=7.3 Hz, 3H).

Example 8

N-[4-((1R,5S,6R)-3-Propyl-3-aza-bicyclo[3.2.0]hept-6-yl)-phenyl]-4-trifluoromethylsulfanyl-benzenesulfonamide Step 1,1-[(1R,5S,6R)-6-(4-amino-phenyl)-3-aza-bicyclo[3.2.0]hept-3-yl]-propan-1-one from example 1.4 (200 mg, 0.82 mmol) was dissolved in THF (15 ml) at −78° C. and potassium hexamethyldisilazide (490 mg, 2.46 mmol) added. The solution was stirred at −78° C. for 1 hour and then 4-(trifluoromethylthio)benzene-1-sulfonyl fluoride (218 mg, 0.82 mmol) was added and the solution was allowed to reach room temperature overnight. The solvent was removed in vacuo and the residue partitioned between ethyl acetate and NaOH (2M). The organic extract was separated, dried (MgSO₄), filtered and concentrated to give 133 mg of N-[4-((1R,5S,6R)-3-propionyl-3-aza-bicyclo[3.2.0]hept-6-yl)-phenyl]-4-trifluoromethylsulfanyl-benzenesulfonamide (yield 34%).

Step 2. Following a procedure in analogy to a procedure described in example 1.6, amide reduction of N-[4-((1R,5S,6R)-3-propionyl-3-aza-bicyclo[3.2.0]hept-6-yl)-phenyl]-4-trifluoromethylsulfanyl-benzenesulfonamide gave 96 mg (yield 99%) of the title compound.

MS (ESI) m/z: 471.0 [M+H]⁺

¹H-NMR (DMSO-d₆): δ [ppm] 10.30 (br s, 1H), 7.84 (m, 4H), 7.13 (d, 2H), 7.01 (d, 2H), 3.11 (m, 1H), 2.87 (m, 2H), 2.73 (m, 1H), 2.62 (m, 1H), 2.40 (t, 1H, J=7.3 Hz, 2H), 2.01 (m, 3H), 1.52 (m, 2H), 0.90 (t, J=7.3 Hz, 3H).

Example 9

4-((R)-2-Methoxymethyl-pyrrolidin-1-yl)-N-[4-((1R,5S,6R)-3-propyl-3-azabicyclo[3.2.0]hept-6-yl)-phenyl]-benzenesulfonamide A solution of 0.07 g rac-2,2'-bis(diphenylphosphino)-1,1'-binaphthalene (BINAP, 0.11 mmol) and 0.043 g tri(dibenzylideneacetone)dipalladioum(0) (0.05 mmol) in 5 ml tetrahydrofuran were added dropwise to a solution of 4-bromo-N-[4-((1R,5S,6R)-3-propyl-3-aza-bicyclo[3.2.0]hept-6-yl)-phenyl]-benzenesulfonamide (0.26 g, 0.59 mmol), (R)-2-(methoxymethyl)pyrrolidine (104 mg, 0.9 mmol), and 0.104 g sodium tert.butylate (1.08 mmol) in 20 ml tetrahydrofuran. The reaction mixture was refluxed for 5½ hours, and, after additional addition of 0.04 ml (R)-2-(methoxymethyl)pyrrolidine, for another 2 hours. After evaporation, the residue was treated with water, extracted twice with diethyl ether and dichloromethane each, and the combined organic layers dried over magnesium sulfate, filtered, and the solvent evaporated. Purification of the thus obtained crude product via silica gel chromatography using a gradient of dichloromethane/methanol 0-12% gave 50 mg (yield 18%) of the title compound.

MS (ESI) m/z: 484.5 [M+H]⁺

¹H-NMR (DMSO-d₆): δ [ppm] 9.85 (br s, 1H), 7.50 (d, 2H), 7.08 (d, 2H), 7.00 (d, 2H), 6.61 (d, 2H), 3.90 (br s, 1H), 3.30 (m, 7H), 3.11 (m, 1H), 2.83 (m, 2H), 2.69 (m, 1H), 2.62 (m, 1H), 1.90 (m, 6H), 1.51 (m, 2H), 0.91 (t, J=7.3 Hz, 3H).

Example 10

N-[4-((1R,5S,6R)-3-Propyl-3-aza-bicyclo[3.2.0]hept-6-yl)-phenyl]-4-pyrrolidin-1-yl-benzenesulfonamide Following a procedure analogous to the procedure described in example 9, 5.6 mg of the title compound (yield 9%) were obtained.

MS (ESI) m/z: 440.2 [M+H]⁺

¹H-NMR (CH₃OH-d₄): δ [ppm] 7.51 (d, 2H), 7.06 (d, 2H), 7.00 (d, 2H), 6.60 (d, 2H), 3.30 (m, 4H), 3.12 (m, 1H), 2.83 (m, 2H), 2.69 (m, 1H), 2.62 (m, 1H), 1.90 (m, 6H), 1.51 (m, 2H), 0.92 (t, J=7.3 Hz, 3H).

Example 11

4-Azetidin-1-yl-N-[4-((1R,5S,6R)-3-propyl-3-aza-bicyclo[3.2.0]hept-6-yl)-phenyl]-benzenesulfonamide Following a procedure analogous to the procedure described in example 9, 12 mg of the title compound (yield 13%) were obtained MS (ESI) m/z: 426.1 [M+H]$^+$
$^1$H-NMR (DMSO-d$_6$): δ [ppm] 7.49 (d, 2H), 7.08 (d, 2H), 6.98 (d, 2H), 6.33 (d, 2H), 3.83 (t, 4H), 3.08 (m, 1H), 2.83 (m, 2H), 2.73 (m, 1H), 2.62 (m, 1H), 2.33 (t, 1H, J=7.3 Hz, 2H), 2.28 (m, 2H), 1.90 (m, 4H), 1.50 (m, 2H), 0.91 (t, J=7.3 Hz, 3H).

Example 12

N-[4-((1R,5S,6R)-3-Propyl-3-aza-bicyclo[3.2.0]hept-6-yl)-phenyl]-4-furan-2-yl-benzenesulfonamide 4-Bromo-N-[4-((1R,5S,6R)-3-propyl-3-aza-bicyclo[3.2.0]hept-6-yl)-phenyl]-benzenesulfonamide (50 mg, 0.11 mmol), 2-(tributylstannyl)-furan (199 mg, 0.56 mmol) and tetrakistriphenylphosphinpalladium(0) (26 mg, 0.02 mmol) were dissolved in 5 ml of tetrahydrofuran and stirred for 40 minutes at 150° C. in the microwave (CEM). The reaction mixture was filtered over celite, washed with methanol, and the filtrate evaporated to dryness under reduced pressure. The residue was purified via silica gel chromatography with ethyl acetate, and ethyl acetate/methanol (15%). Fractions containing the product were combined, the solvent evaporated to yield 4.2 mg of the title product (yield 9%).

MS (ESI) m/z: 437.1 [M+H]$^+$
$^1$H-NMR (DMSO-d$_6$): δ [ppm] 7.86 (m, 1H), 7.72 (m, 4H), 7.61 (s, 1H), 7.16 (d, 2H), 7.12 (d, 2H), 6.91 (s, 1H), 6.53 (s, 1H), 3.75 (m, 2H), 3.15 (m, 4H), 2.30 (t, 1H, J=7.3 Hz, 2H), 1.85 (m, 2H), 1.28 (m, 2H), 1.06 (t, J=7.3 Hz, 3H).

Example 13

N-[4-((1R,5S,6R)-3-Propyl-3-aza-bicyclo[3.2.0]hept-6-yl)-phenyl]-4-thiophen-2-yl-benzenesulfonamide Following a procedure analogous to the procedure described in example 12 the title compound was obtained (37 mg, yield 67%).

MS (ESI) m/z: 453.1 [M+H]$^+$
$^1$H-NMR (DMSO-d$_6$): δ [ppm] 10.24 (br s, 1H), 7.82 (m, 1H), 7.77 (m, 4H), 7.64 (m, 2H), 7.16 (m, 3H), 7.08 (d, 2H), 4.01 (m, 2H), 3.70 (m, 1H), 3.62 (m, 1H), 3.32 (m, 1H), 3.10 (m, 4H), 2.20 (t, 1H, J=7.3 Hz, 2H), 1.72 (m, 2H), 1.18 (m, 2H), 0.92 (t, J=7.3 Hz, 3H).

Example 14

4-Isopropyl-N-[4-((1S,5R,6S)-3-propyl-3-aza-bicyclo[3.2.0]hept-6-yl)-phenyl]-benzenesulfonamide Step 1. Following a procedure analogous to the procedure described in example 1.5, the sulfonamide was obtained (175 mg, yield 100%).
Step 2. Following a procedure analogous to the procedure described in example 1.6, the title compound (amount 78 mg; yield 100%) was obtained.

MS (ESI) m/z 413.1 [M+H]$^+$
$^1$H-NMR (DMSO-d$_6$): δ [ppm] 10.08 (br s, 1H), 7.66 (d, 2H), 7.40 (d, 2H), 7.12 (d, 2H), 7.02 (d, 2H), 3.40 (m, 1H), 3.07 (m, 1H), 2.85 (m, 3H), 2.72 (m, 1H), 2.62 (m, 1H), 2.39 (t, 1H, J=7.3 Hz, 2H), 1.95 (m, 4H), 1.51 (m, 2H), 1.18 (d, 6H), 0.91 (t, J=7.3 Hz, 3H).

Example 15 endo-4-Isopropyl-N-[4-(-3-propionyl-3-aza-bicyclo[3.2.0]hept-6-yl)-phenyl]-benzenesulfonamide 15.1 endo-1-[6-(4-Nitro-phenyl)-3-aza-bicyclo[3.2.0]hept-3-yl]-propan-1-one The title compound was prepared in analogy to the procedure described in example 2.1.
ESI-MS: 275.1 [M+H]$^+$ 15.2 endo-1-[6-(4-Amino-phenyl)-3-aza-bicyclo[3.2.0]hept-3-yl]-propan-1-one The title compound was prepared in analogy to the procedure described in example 2.2.
ESI-MS: 245.1 [M+H]$^+$ 15.3 endo-4-Isopropyl-N-[4-(-3-propionyl-3-aza-bicyclo[3.2.0]hept-6-yl)-phenyl]-benzenesulfonamide The title compound was prepared in analogy to the procedure described in example 2.3.
ESI-MS: 427.15 [M+H]$^+$

Example 16 endo-4-Isopropyl-N-[4-(3-propyl-3-aza-bicyclo[3.2.0]hept-6-yl)-phenyl]-benzenesulfonamide The title compound was prepared in analogy to the procedure described in example 3.
ESI-MS: 413.15 [M+H]$^+$
$^1$H-NMR (CDCl$_3$, 400 MHz): δ [ppm] 7.7 (d, 2H), 7.25 (m, 4H), 7.0 (d, 2H), 3.6 (m, 1H), 2.95 (m, 2H), 2.8 (m, 2H), 2.5-2.3 (m, 3H), 2.2 (m, 2H), 2.05 (m, 1H), 1.85 (m, 1H), 1.45 (m, 2H), 1.25 (d, 6H), 0.9 (t, 3H).

III. Examples of Galenic Administration Forms

A) Tablets

Tablets of the following composition are pressed on a tablet press in the customary manner:
  40 mg of substance from Example 8
  120 mg of corn starch
  13.5 mg of gelatin
  45 mg of lactose
  2.25 mg of Aerosil® (chemically pure silicic acid in sub-microscopically fine dispersion)
  6.75 mg of potato starch (as a 6% paste)

B) Sugar-Coated Tablets
  20 mg of substance from Example 8
  60 mg of core composition 70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biological Investigations

Receptor Binding Studies:

The substance to be tested was either dissolved in methanol/Chremophor® (BASF-AG) or in dimethyl sulfoxide and then diluted with water to the desired concentration.

Dopamine $D_3$ Receptor:

The assay mixture (0.250 ml) was composed of membranes derived from ~$10^6$ HEK-293 cells possessing stably expressed human dopamine $D_3$ receptors, 0.1 nM [$^{125}$I]-iodosulpride and incubation buffer (total binding) or, in addition, test substance (inhibition curve) or 1 µM spiperone (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin, 10 µM quinolone and 0.1% ascorbic acid (prepared fresh daily). The buffer was adjusted to pH 7.4 with HCl.

Dopamine $D_{2L}$ Receptor:

The assay mixture (1 ml) was composed of membranes from ~106 HEK-293 cells possessing stably expressed human dopamine $D_{2L}$ receptors (long isoform) and 0.01 nM [$^{125}$I]iodospiperone and incubation buffer (total binding) or, in addition, test substance (inhibition curve) or 1 µM haloperidol (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptor binding studies are expressed as receptor binding constants $K_i(D_2)$ and $K_i(D_3)$, respectively, as herein before described, and given in table 1.

In these tests, the compounds according to the invention exhibit very good affinities for the $D_3$ receptor (<10 nM, frequently <5 nM) and bind selectively to the $D_3$ receptor.

The results of the binding tests are given in table 1.

TABLE 1

| Example | $K_i(D3)$* [nM] | $K_i(D2)$* [nM] | $K_i(D2)$*/$K_i(D3)$* |
|---|---|---|---|
| 1 | 0.47 | 12.9 | 28 |
| 3# | 0.7 | 31 | 45 |
| 4 | 5.43 | 66.6 | 12 |

TABLE 1-continued

| Example | $K_i(D3)$* [nM] | $K_i(D2)$* [nM] | $K_i(D2)$*/$K_i(D3)$* |
|---|---|---|---|
| 5 | 3.15 | 72.1 | 23 |
| 6 | 4.13 | 47.0 | 11 |
| 7 | 1.31 | 31.7 | 24 |
| 8 | 1.81 | 30.2 | 17 |
| 9 | 4.08 | 54.8 | 13 |
| 10 | 1.98 | 32.0 | 16 |
| 11 | 2.19 | 56.7 | 26 |
| 12 | 4.46 | 37.6 | 8 |
| 13 | 1.32 | 13.1 | 10 |
| 14 | 59.7 | 469 | 8 |
| 16 | 5.3 | 207.6 | 39 |

*Receptor binding constants obtained according to the assays described herein before
para compound

We claim:
1. A compound of the formula (I)

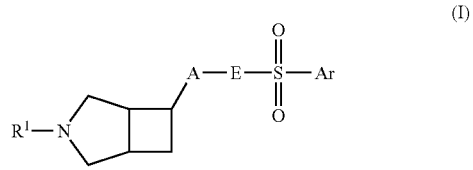

wherein,
$R^1$ is H, $C_1$-$C_6$-alkyl which may be substituted by $C_3$-$C_6$-cycloalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl;
A is phenylene, pyridylene, pyrimidylene, pyrazinylene, pyridazinylene or thiophenylene, which can be substituted by one or more substituents selected from halogen, methyl, methoxy and $CF_3$;
E is $NR^5$ or $CH_2$, wherein $R^5$ is H or $C_1$-$C_3$-alkyl;
Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$ where $R^8$ is H, $C_1$-$C_4$-alkyl, fluorinated $C_1$-$C_4$-alkyl, $C_1$-$C_4$-alkylcarbonyl or fluorinated $C_1$-$C_4$ alkylcarbonyl, and where the cyclic radical Ar may carry 1, 2 or 3 substituents $R^a$;
$R^a$ is halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, NH—C(O)—$NR^6R^7$, $NR^6R^7$, $NR^6R^7$-$C_1$-$C_6$-alkylene, O—$NR^6R^7$ where $R^6$ and $R^7$ are, independently of each other, H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring, phenylsulfonyl, benzyloxy, phenoxy, phenyl, or a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the 5 last-mentioned radicals may carry 1, 2, 3 or 4 substituents selected from hydroxy and the radicals $R^a$;

and physiologically tolerated acid addition salts thereof.

2. A compound as claimed in claim 1, wherein

Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S, and where the cyclic radical may carry 1, 2 or 3 substituents $R^a$ selected from the group consisting of halogen, $C_1$-$C_6$-alkyl, fluorinated $C_1$-$C_6$-alkyl, $C_2$,—$C_6$-alkenyl, fluorinated $C_1$-$C_6$-alkenyl, $C_3$-$C_6$-cycloalkyl, fluorinated $C_3$-$C_6$-cycloalkyl, $C_1$-$C_6$-alkoxy, fluorinated $C_1$-$C_6$-alkoxy, CN, acetyl, carboxy, $NR^6R^7$, $NR^6R^7$-$C_1$-$C_6$-alkylene, where $R^6$ and $R^7$ are, independently of each other, H, $C_1$-$C_4$-alkyl or fluorinated $C_1$-$C_4$-alkyl or may form, together with N, a 4-, 5- or 6-membered saturated or unsaturated ring, and a saturated or unsaturated 3-, 4-, 5- or 6-membered heterocyclic ring comprising as ring members 1, 2 or 3 heteroatoms selected from N, O and S.

3. The compound as claimed in claim 1, wherein $R^1$ is n-propyl or allyl.

4. The compound as claimed in claim 1, wherein A is phenylene, pyridylene or pyrimidylene.

5. The compound as claimed in claim 1, wherein E is NH.

6. The compound as claimed in claim 1, wherein Ar is phenyl, thienyl, pyridyl, pyrimidyl, imidazolyl, isoxazolyl, thiazolyl, triazolyl, thiadiazolyl, quinolinyl, isoquinolinyl, tetrahydroisoquinolinyl, benzofuranyl, benzothiophenyl, benzoxazinyl, benzothiazolyl, benzoxadiazolyl, benzothiadiazolyl or indanyl, which may be substituted as defined in claim 1.

7. The compound as claimed in claim 6, wherein Ar is phenyl, thienyl, pyridyl, benzofuranyl or indanyl, which may be substituted.

8. The compound as claimed in claim 1, wherein Ar carries one radical $R^a$ of the formula to a subject having a medical disorder selected from the group consisting of Parkinson's disease, schizophrenia, a cognitive disturbance, depression, anxiety, addiction, a kidney function disturbance, an eating disturbance, psychosis, and a behavioral disturbance,

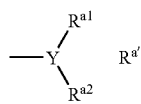

wherein

Y is N, CH or CF, $R^{a1}$ and $R^{a2}$ are independently of each other selected from $C_1$-$C_2$-alkyl, fluorinated $C_1$-$C_2$-alkyl, provided for Y being CH or CF one of the radicals $R^{a1}$ or $R^{a2}$ may also be hydrogen or fluorine, or $R^{a1}$ and $R^{a2}$ together form a radical $(CH_2)_m$, wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6.

9. The compound as claimed in claim 8, wherein the radical $R^{a'}$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2difluoroethyl, cyclopropyl, cyclobutyl, 1-fluorocyclopropyl, 2-fluorocyclopropyl, (S)- and (R)-difluorocyclopropyl.

10. The compound as claimed in claim 8, wherein the radical $R^{a'}$ is selected from 4-morpholinyl, 4-thiomorpholinyl, 4-(1,1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-methoxymethylpyrrolidin-1-yl, (R)-2-methoxymethylpyrrolidin-1-yl, (S)-2-methoxymethylpyrrolidin-1-yl, 2-oxopyrrolidin-1-yl, 2-oxooxazolidin-3-yl, piperidin-1-yl, 2-methylpiperidin-1-yl, (S)-2-methylpiperidin-1-yl and (R)-2-methylpiperidin-1-yl.

11. The compound as claimed in claim 8, wherein the radical $R^{a'}$ carries 1, 2, 3 or 4 fluorine atoms.

12. The compound as claimed in claim 1, where $R^a$ is selected from fluorinated methyl, $C_1$-$C_4$-alkoxy, fluorinated $C_1$-$C_4$-alkoxy, $C_1$-$C_4$-alkylthio and fluorinated $C_1$-$C_4$-alkylthio.

13. The compound as claimed in claim 1, wherein Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

14. The compound as claimed in claim 13, wherein Ar carries one heteroaromatic radical $R^a$, which is selected from furanyl, thienyl, pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents selected from halogen, $C_1$-$C_4$-alkyl, $C_1$-$C_4$-alkoxy, fluorinated $C_1$-$C_4$-alkyl and fluorinated $C_1$-$C_4$-alkoxy.

15. The compound as claimed in claim 1, wherein Ar is phenyl.

16. The compound as claimed in claim 15, wherein Ar is phenyl which carries 1, 2 or 3 substituents selected from the group consisting of halogen, $C_1$-$C_4$-alkyl, fluorinated $C_1$-$C_4$-alkyl, $C_1$-$C_4$-alkoxy, fluorinated $C_1$-$C_4$-alkoxy, 1-azetidinyl, 1-pyrrolidinyl, 2-furanyl and 2-thienyl, where the 4 last-mentioned radicals may be substituted by 1 or 2 substituents selected halogen, $C_1$-$C_4$-alkyl, fluorinated $C_1$-$C_4$-alkyl, $C_1$-$C_4$-alkoxy, fluorinated $C_1$-$C_4$-alkoxy and $C_1$-$C_4$-alkoxy-$C_1$-$C_4$-alkyl.

17. The compound as claimed in claim 1, wherein Ar is phenyl that carries a radical $R^a$ in the 4-position of the phenyl ring.

18. A pharmaceutical composition comprising at least one compound as claimed in claim 1, optionally together with at least one physiologically acceptable carrier or auxiliary substance.

19. A method for treating a medical disorder selected from the group consisting of Parkinson's disease, schizophrenia, a cognitive disturbance, depression, anxiety, addiction, a kidney function disturbance, an eating disturbance, psychosis, and a behavioral disturbance, said method comprising administering an effective amount of at least one compound as claimed in claim 1 to a subject having a medical disorder selected from the group consisting of Parkinson's disease, schizophrenia, a cognitive disturbance, depression, anxiety, addiction, a kidney function disturbance, an eating disturbance, psychosis, and a behavioral disturbance.

* * * * *